(12) United States Patent
Goodman et al.

(10) Patent No.: US 11,013,533 B2
(45) Date of Patent: May 25, 2021

(54) IMPLANT DELIVERY AND RETRIEVAL SYSTEMS AND METHODS

(71) Applicant: Pacesetter, Inc., Sylmar, CA (US)

(72) Inventors: Daniel Goodman, Minnetonka, MN (US); John Pocrnich, Roseville, MN (US)

(73) Assignee: PACESETTER, INC., Sylmar, CA (US)

( * ) Notice: Subject to any disclaimer, the term of this patent is extended or adjusted under 35 U.S.C. 154(b) by 137 days.

(21) Appl. No.: 16/214,819

(22) Filed: Dec. 10, 2018

(65) Prior Publication Data

US 2019/0175219 A1 Jun. 13, 2019

Related U.S. Application Data

(60) Provisional application No. 62/596,968, filed on Dec. 11, 2017.

(51) Int. Cl.
*A61B 17/34* (2006.01)
*A61N 1/372* (2006.01)
(Continued)

(52) U.S. Cl.
CPC .......... *A61B 17/3468* (2013.01); *A61N 1/372* (2013.01); *A61B 2017/00292* (2013.01);
(Continued)

(58) Field of Classification Search
CPC .. A61N 1/3756; A61N 1/372; A61N 1/37518; A61N 1/362; A61N 1/37512;
(Continued)

(56) References Cited

U.S. PATENT DOCUMENTS 5,906,622 A * 5/1999 Lippitt ................. A61B 17/221
606/113
6,626,915 B2 9/2003 Leveillee
(Continued)

FOREIGN PATENT DOCUMENTS

DE 8707515 U1 9/1987

OTHER PUBLICATIONS

PCT International Search Report for PCT Counterpart Application No. PCT/US2018/031042 Containing International Search Report, 3 pp. (dated Aug. 31, 2018).
(Continued)

*Primary Examiner* — Richard G Louis
(74) *Attorney, Agent, or Firm* — Womble Bond Dickinson (US) LLP

(57) ABSTRACT

Systems and methods for delivering and retrieving a leadless pacemaker are described. A leadless pacemaker retrieval system includes a catheter system having a snare assembly to capture the leadless pacemaker. The catheter system includes sheaths extending distally from a shaft, and the snare assembly includes several snare legs, such as segments of snare loops, that extend from one sheath to connect to another sheath. The snare loops can have bights that connect to opposing sheaths to form a docking space between the legs of the snare loops and radially between the sheaths. The snare assembly is movable between an engaged position and a disengaged position by translating the snare legs within lumens of the corresponding sheaths. In the engaged position, the snare assembly tightens around the leadless pacemaker to allow the leadless pacemaker to be retrieved. Other embodiments are also described and claimed.

20 Claims, 53 Drawing Sheets

(51) Int. Cl.
  *A61B 17/00* (2006.01)
  *A61B 17/221* (2006.01)
  *A61N 1/375* (2006.01)
  *A61N 1/362* (2006.01)
  *A61B 17/22* (2006.01)

(52) U.S. Cl.
  CPC .............. *A61B 2017/00358* (2013.01); *A61B 2017/2212* (2013.01); *A61B 2017/2215* (2013.01); *A61B 2017/22035* (2013.01); *A61N 1/362* (2013.01); *A61N 1/3756* (2013.01); *A61N 1/37518* (2017.08)

(58) Field of Classification Search
  CPC .............. A61B 17/221; A61B 17/3468; A61B 2017/2215; A61B 2017/00358; A61B 2017/22035; A61B 2017/00292
  See application file for complete search history.

(56) References Cited

U.S. PATENT DOCUMENTS

| | | |
|---|---|---|
| 7,775,989 B2 | 8/2010 | Nakao |
| 8,974,470 B2 | 3/2015 | Lampropoulos et al. |
| 9,039,713 B2 | 5/2015 | Segermark |
| 9,492,674 B2 | 11/2016 | Schmidt et al. |
| 9,539,016 B2 | 1/2017 | Lampropoulos et al. |
| 9,566,673 B2 | 2/2017 | Pham et al. |
| 2002/0107526 A1* | 8/2002 | Greenberg .......... A61B 17/221 606/108 |
| 2005/0209609 A1 | 9/2005 | Wallace |
| 2007/0156197 A1 | 7/2007 | Root et al. |
| 2011/0270339 A1 | 11/2011 | Murray, III et al. |
| 2012/0239077 A1 | 9/2012 | Zaver et al. |
| 2013/0144311 A1* | 6/2013 | Fung ................ A61B 17/12013 606/139 |
| 2014/0243848 A1 | 8/2014 | Auricchio et al. |
| 2014/0276908 A1 | 9/2014 | Raybin et al. |
| 2015/0051609 A1 | 2/2015 | Schmidt |
| 2015/0051612 A1 | 2/2015 | Schmidt |
| 2015/0051682 A1 | 2/2015 | Schmidt et al. |
| 2015/0066047 A1* | 3/2015 | Chu .................... A61B 17/50 606/113 |
| 2015/0201848 A1 | 7/2015 | Stalker et al. |
| 2015/0335884 A1 | 11/2015 | Khairkhahan et al. |
| 2016/0228712 A1 | 8/2016 | Koop |
| 2016/0310747 A1 | 10/2016 | Grubac et al. |
| 2016/0346002 A1 | 12/2016 | Avneri |
| 2018/0280058 A1 | 10/2018 | Meade et al. |

OTHER PUBLICATIONS

PCT Written Opinion for PCT Counterpart Application No. PCT/US2018/031042, 12 pp (dated Aug. 31, 2018).

PCT International Preliminary Report on Patentability for PCT Application No. PCT/US2018/031042, 14 pp. (dated Nov. 14, 2019).

* cited by examiner

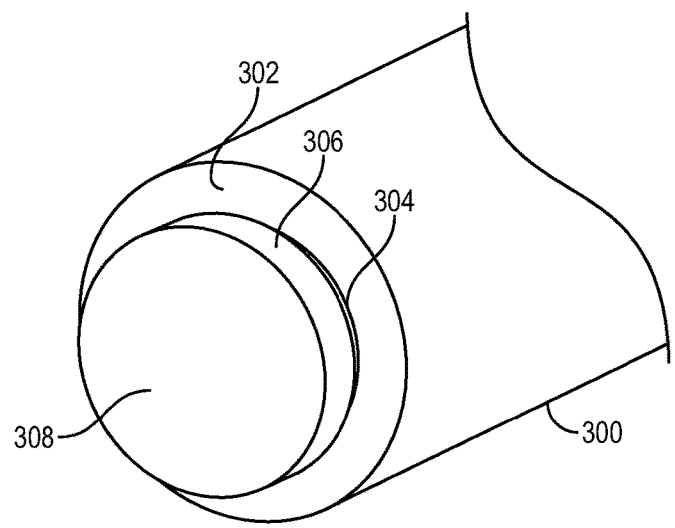
FIG. 15A
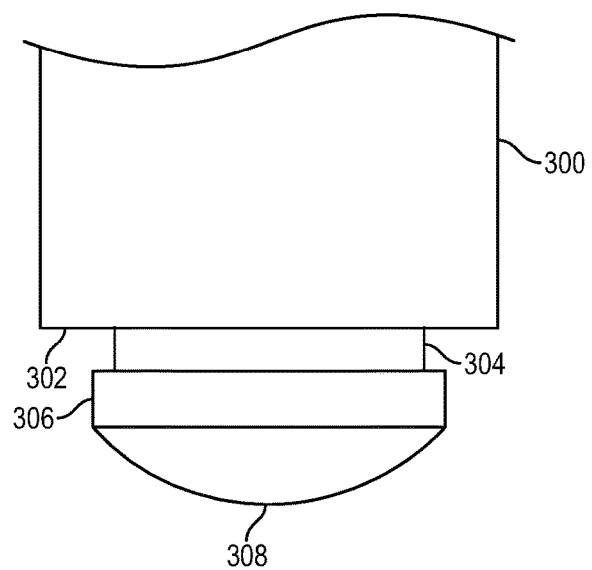 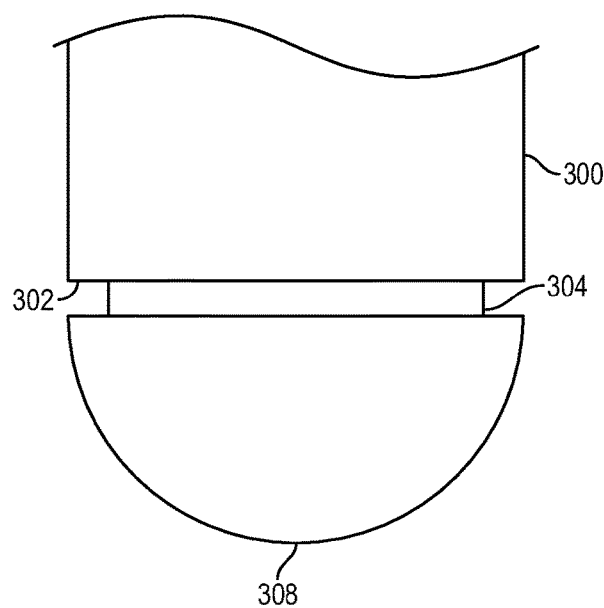
FIG. 15B     FIG. 15C

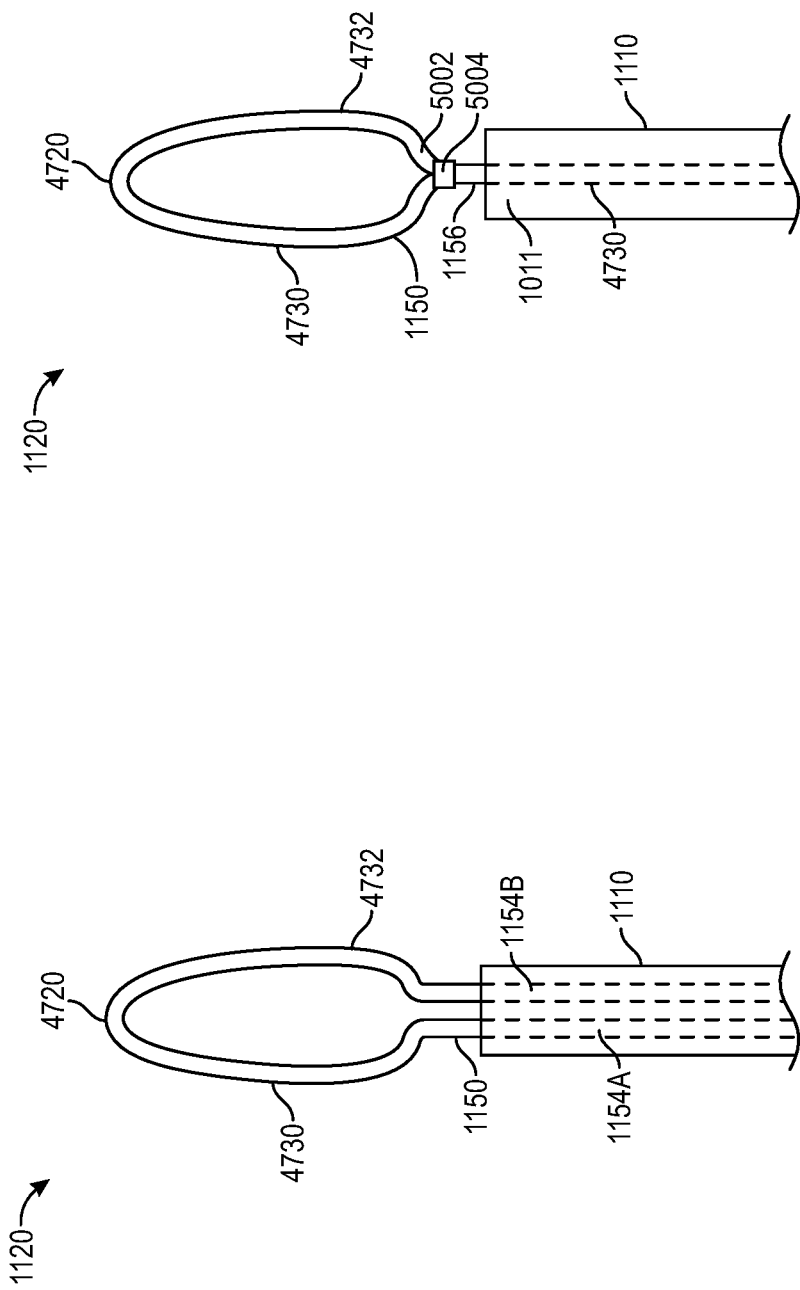

IMPLANT DELIVERY AND RETRIEVAL SYSTEMS AND METHODS

This application claims the benefit of priority of U.S. Provisional Patent Application No. 62/596,968, filed on Dec. 11, 2017, which is incorporated herein by reference in its entirety to provide continuity of disclosure.

BACKGROUND

Field

The present disclosure relates to leadless pacemakers and related delivery and retrieval systems and methods. More particularly, the present disclosure relates to systems and methods for loading a leadless pacemaker onto a catheter system for delivery to or retrieval from an implant site.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist. For example, a pulse generator, when located subcutaneously, presents a bulge in the skin that patients can find unsightly, unpleasant, or irritating, and which patients can subconsciously or obsessively manipulate. Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker.

Similar to active fixation implantable leads used with conventional pulse generators, leadless pacemakers are typically fixed to an intracardial implant site by an actively engaging mechanism such as a screw or helical member that threads into the myocardium. Leadless pacemakers are often delivered to an intracardial implant site via a delivery system including a delivery catheter. Conventional delivery catheter systems are typically long (e.g., approximately 42 mm or longer), making navigation of the patient anatomy difficult and increasing a footprint of the system at the implant site.

Some conventional delivery systems are tether based in which attachment of the leadless pacemaker to the delivery catheter is dependent on the tether alignment. Once the tether alignment is lost, which may occur due to system tolerances or anatomical interferences, among other factors, the leadless pacemaker may spontaneously release from the delivery catheter. Such a spontaneous release may cause embolism, a need to retrieve the leadless pacemaker, and/or other patient risks. Retrieval may be performed by removing the delivery catheter and introducing a retrieval catheter to remove the leadless pacemaker. The delivery catheter system is generally different in structure and operation from the retrieval catheter system, which increases procedure time, complexity, and cost. If retrieval cannot be performed using a retrieval catheter system, the leadless pacemaker is typically retrieved through surgery, further complicating the procedure. Moreover, implanting a second leadless pacemaker into a patient often requires the use of a second catheter delivery system, as many conventional catheter systems fail to accommodate bed-side loading of leadless pacemakers onto a previously used catheter system. Instead, many conventional catheter systems are preloaded during manufacturing. It is with these observations in mind, among others, that the presently disclosed technology was conceived and developed.

SUMMARY

Implementations described and claimed herein address the foregoing observations by providing systems and methods for delivering and retrieving a leadless pacemaker. In an implementation, a catheter system includes a shaft, and several sheaths extending from the shaft to respective ends. The catheter system includes a snare assembly having a several snare legs that extend between the sheaths. For example, several first snare legs extend from a first end of a first sheath to respective first leg ends connected to a second sheath. Similarly, several second snare legs extend from a second end of a second sheath to respective second leg ends coupled to the first sheath. A docking space is formed between the snare legs to receive the leadless pacemaker.

In an implementation, the snare legs are segments of respective snare loops. For example, a snare wire can be looped on itself to form the first snare legs joined at a first bight. Similarly, a snare wire can be looped on itself to form the second snare legs joined at a second bight. The first snare legs can be segments of a first snare loop and the second snare legs can be segments of a second snare loop. The snare loops can extend from respective sheaths and the bights of the snare loops can be coupled to respective opposite sheaths. For example, the first snare loop can extend from a lumen of a first sheath to the first bight that is attached to a second sheath, and the second snare loop can extend from a lumen of the second sheath to the second bight that is attached to the first sheath. Each bight can be held by a sidewall of the opposite sheath, e.g., by passing the loop through the sidewall, or the bights can be bonded to the sheaths by an adhesive joint, a mechanical bond, etc.

In an implementation, a leadless pacemaker retrieval system includes one or more handle portions coupled to the snare assembly. Movement of the handle portion(s) causes a distance between the sheaths to reduce. For example, a first handle portion can be coupled to the first snare loop, and movement of the first handle portion can cause a length of the snare legs between the first sheath and the second sheath to reduce. Similarly, a second handle portion can be coupled to the second snare loop, and movement of the second handle portion can cause a length of the snare legs between the second sheath and the first sheath to reduce. Accordingly, actuation of the handle portion(s) can reduce the docking space by retracting the snare legs into the respective sheaths such that the snare assembly tightens around the leadless pacemaker. The sheaths can then be retracted to retrieve the leadless pacemaker.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIGS. 15A-15C show examples of the docking projection with a round surface.

FIGS. 50A and 50B are schematic illustrations of snare loops for use in snare assemblies according to the present disclosure.

DETAILED DESCRIPTION

Aspects of the present disclosure involve systems and methods for delivering and retrieving a leadless biostimulator, such as a leadless pacemaker. Generally, the leadless pacemaker is delivered and retrieved from an implant location in a patient using a catheter system. The presently disclosed systems and methods thus facilitate repeated implantation and/or retrieval of leadless pacemakers via a single catheter delivery and retrieval system, thereby reducing waste and the costs associated therewith. Additionally, the systems and methods described herein permit a single catheter system to deliver and retrieve different leadless pacemakers having varying configurations further reducing the operation burden of stocking multiple systems applicable to the various configurations.

In one aspect, the catheter system includes a retriever in the form of a grasper, a snare, and/or the like, releasably engagable to a docking end of the leadless pacemaker to provide torque transmission to the leadless pacemaker during deployment, as well as providing the engagement, delivery, detachment, and/or retrieval of the leadless pacemaker. The retriever reduces the risk of spontaneous or otherwise undesired release of the leadless pacemaker from the catheter during delivery or retrieval. Moreover, the retriever provides reliable detachment independent of a relative position of a dual-tether system and isolates rotation forces of the leadless pacemaker from the catheter system, which may otherwise cause binding and/or torque-wind in a dual-tether system. Tool-less, bed-side loading is facilitated with the presently disclosed technology, permitting the deployment of multiple leadless pacemakers into the patient anatomy with reduced tissue trauma to the patient anatomy during deployment due to the radial opening of the retriever.

The systems and methods described herein generally relate to a loading tool having a retriever for releasably engaging a docking projection of a medical implant, as well as to methods of delivering and retrieving the same. While the present disclosure is discussed with reference to leadless cardiac pacemakers and torque as a loading technique, it will be appreciated that the presently disclosed technology is applicable to other biostimulators and/or medical implant systems and methods as well as loading techniques.

Figure 1:
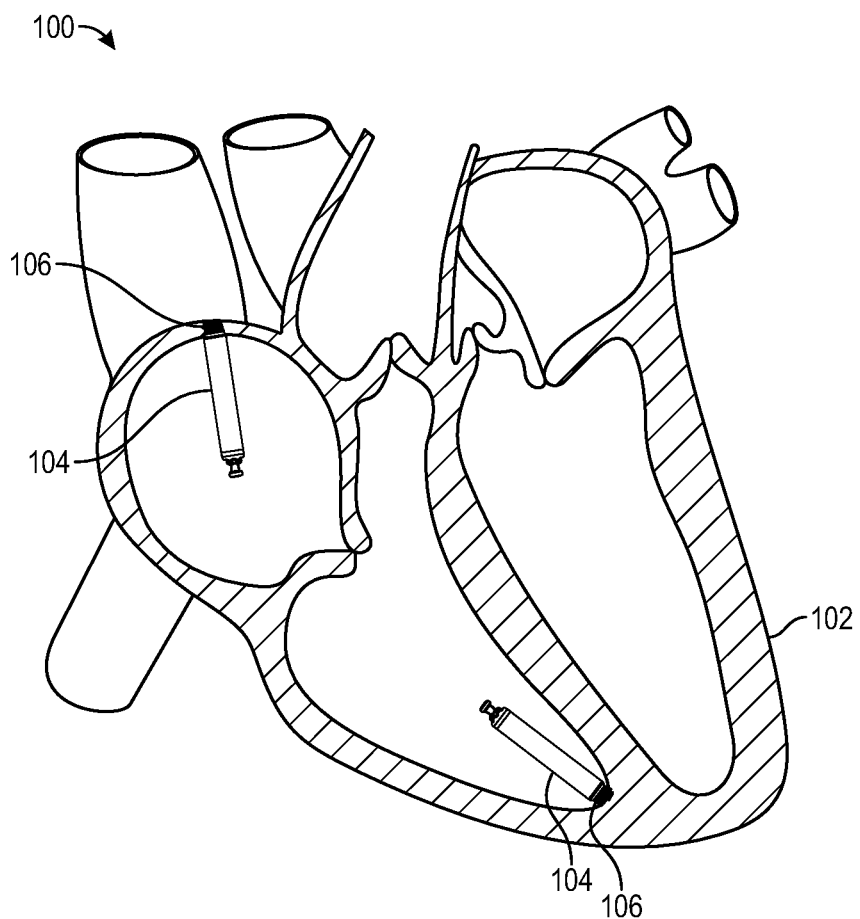
FIG. 1 is a diagrammatic medial-lateral cross-section of a patient heart illustrating an example cardiac pacing system having one or more leadless pacemakers.

To begin a detailed description of an example cardiac pacing system 100 having one or more leadless pacemakers 104, reference is made to FIG. 1. The leadless pacemakers 104 may each be configured for temporary leadless pacing of a patient heart 102. In one implementation, each of the leadless pacemakers 104 are configured for placement on or attachment to the inside or outside of a cardiac chamber, such as the right atrium and/or right ventricle, of the patient heart 102. The leadless pacemakers 104 may be attached to cardiac tissue of the patient heart 102, for example, via a helical anchor 106 that is threaded through the myocardium. It will be appreciated, however, that other primary fixation mechanisms, as well as secondary fixation mechanisms in some cases, may be used to attach the leadless pacemaker 104 to tissue or otherwise restrict movement of the leadless pacemaker 104 during implantation.

Figure 2:
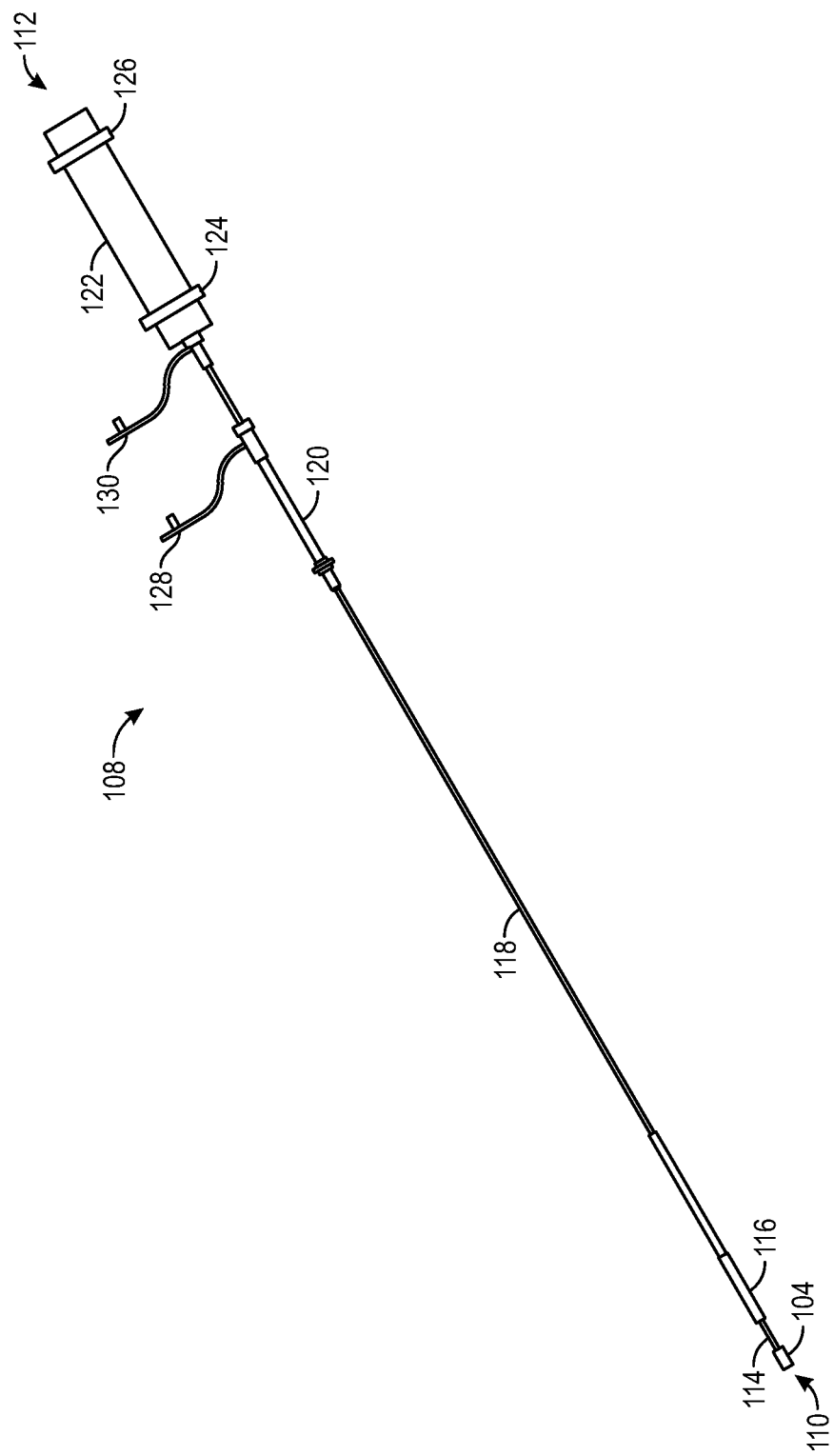
FIG. 2 shows an example catheter system for delivering and/or retrieving a leadless pacemaker.

The leadless pacemakers 104 are delivered to and/or retrieved from the patient heart 102 using a catheter system 108, as shown in FIG. 2. Generally, the catheter system 108 releasably engages the leadless pacemaker 104 for intravenous advancement into the patient heart 102. The catheter system 108 engages the leadless pacemaker 104 in such a manner as to facilitate fixation to cardiac tissue, for example, using the helical anchor 106. As described herein, where the fixation mechanism engages the cardiac tissue through rotation, such as with the helical anchor 106, the catheter system 108 is adapted to provide torque transmission to the leadless pacemaker 104. Stated differently, the catheter system 108 engages features of the leadless pacemaker 104 to apply torque to the leadless pacemaker 104 to screw the helical anchor 106 into cardiac tissue.

The catheter system 108 engages the leadless pacemaker 104 at a distal end 110 and includes a handle at a proximal end 112 for directing the delivery and/or retrieval of the leadless pacemaker 104. In one implementation, the catheter system 108 includes a torque shaft 114, a sleeve 116, and an introducer sheath 120. The catheter system 108 may also include a steerable catheter 116 for deflecting the catheter system 108 and/or one or more flush ports 128 and 130 for flushing saline or other fluids through the catheter system 118.

The torque shaft 114 provides torque transmission to the leadless pacemaker 104 from the steerable catheter 118 and otherwise directs movement of the leadless pacemaker 104 as controlled by one or more steering knobs (e.g., a first steering knob 124 and a second steering knob 126) disposed on a handle body 122. The introducer sheath 120 can be advanced distally over the steerable catheter 118 to provide additional steering and support for the steerable catheter 118 during delivery and/or retrieval and to surround the leadless pacemaker 104 as it is introduced through a trocar or introducer into the patient anatomy. Similarly, the sleeve 116 is movable along the steerable catheter 118 and may be displaced distally over the leadless pacemaker 104 to cover the torque shaft 114, the leadless pacemaker 104, and the helical anchor 106 to protect patient tissue and anatomy during delivery and/or retrieval.

Figure 3:
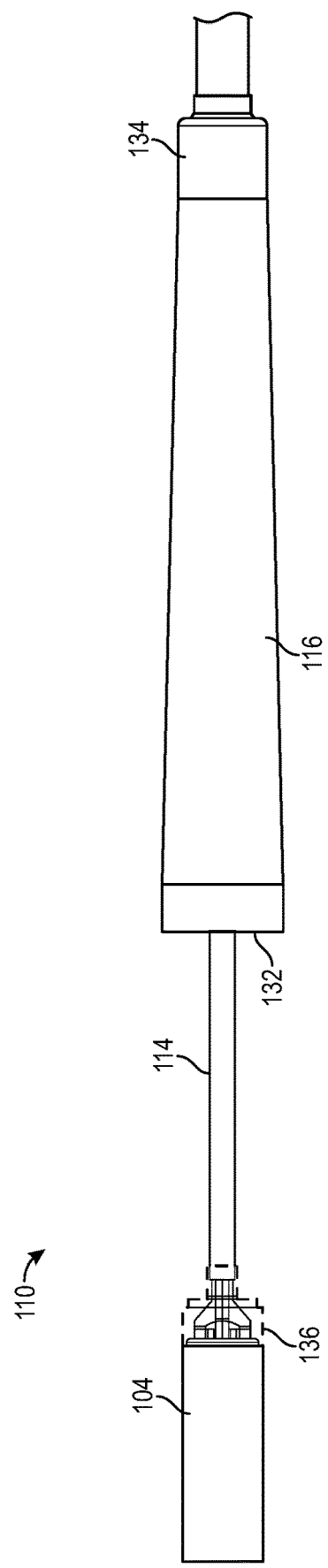
FIG. 3 is a detailed view of a distal end of the catheter system.

Turning to FIG. 3, a detailed view of the distal end 110 of the catheter system 118 is shown. In one implementation, the steerable catheter 118 extends through a sleeve cap 134 into the sleeve 116 where it is engaged to the torque shaft 114. The sleeve 116 may be displaceable over the torque shaft 114 and leadless pacemaker 104 such that the leadless pacemaker 104 is within the sleeve 116 proximal to a distal edge 132 of the sleeve 116. The sleeve 116 may also be steerable.

Figure 4A:
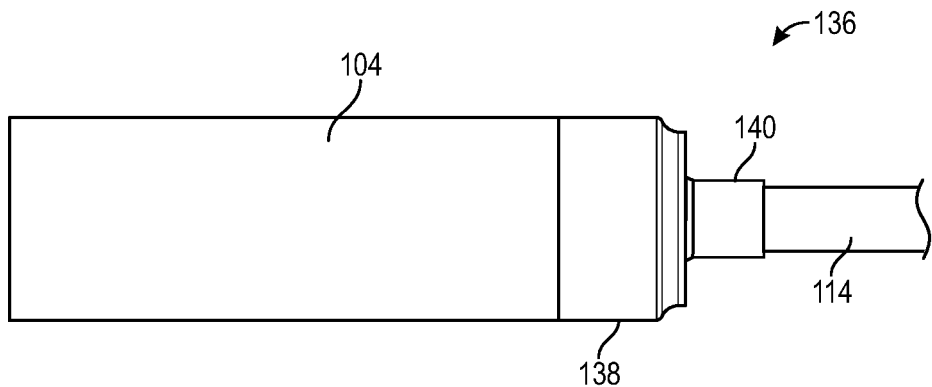
FIGS. 4A-4C each show a retriever in a docked position with a leadless pacemaker with FIGS. 4B and 4C being side and top views, respectively, and showing a docking cap transparent.
Figure 4B:
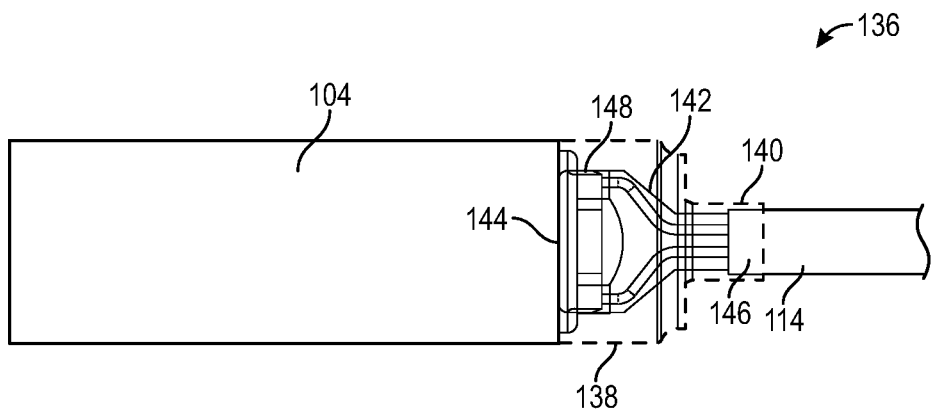
Figure 4C:
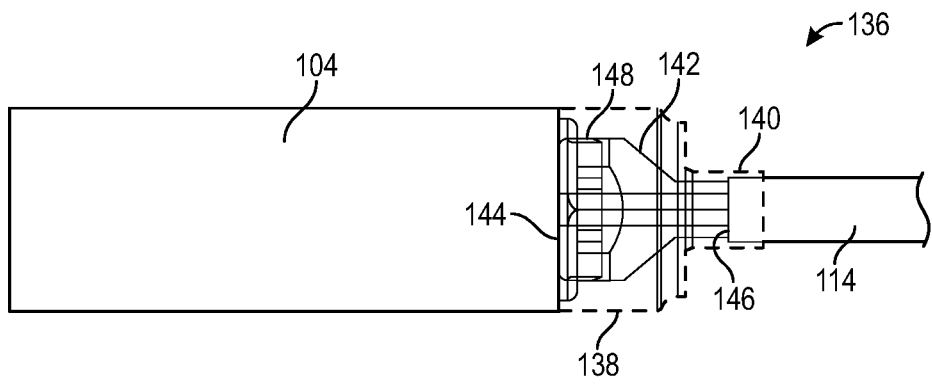

In one implementation, a distal end of the torque shaft 114 is engaged to a docking cap 136, which is configured to releasably engage the leadless pacemaker 104. The torque shaft 114 and the docking cap 136 each deliver torque to the leadless pacemaker 104 during delivery and/or retrieval. FIGS. 4A-4C illustrate the catheter system 108 in a docked or engaged position with the docking cap 136 sheathed over a docking end of the leadless pacemaker 104. In one implementation, the docking cap 136 includes a body 138 and a receiving portion 140 configured to engage a distal end 146 of the torque shaft 114. The distal end 146 of the torque shaft 114 may remain rigidly attached to the receiving portion 140 during use.

The body 138 of the docking cap 136 defines a chamber 142. As can be understood from FIGS. 4B-4C, a docking projection 148 extending from the docking end of the leadless pacemaker 104 is disposed within the chamber 142 in the docked position. A retriever 144 is displaceable within a lumen of the torque shaft 114 and configured to releasably engage the docking projection 148. More particularly, the retriever 144 is extendable through the body 138 of the docking cap 136 for placement relative to the docking projection 148, and the body 138 of the docking cap 136 is sheathed over the docking projection 148 causing the retriever 144 to capture the docking projection 148 within the chamber 142.

Figure 5:
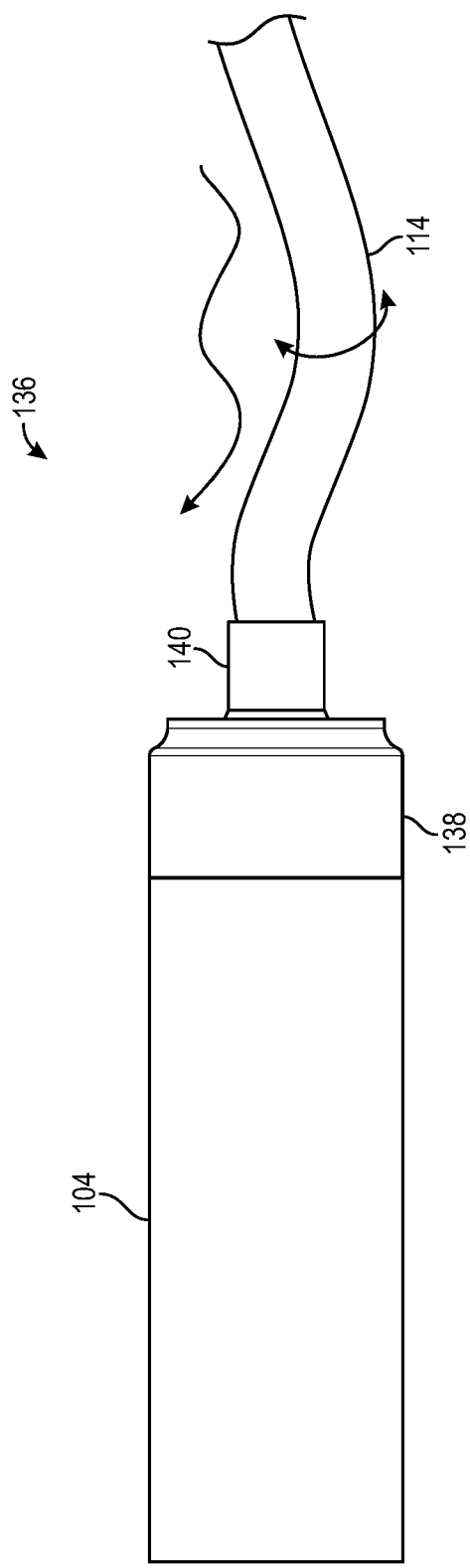
FIG. 5 depicts example movement of a flexible element, such as a torque shaft or a catheter.

In the docked position, the catheter system 108 provides torque transmission to the leadless pacemaker 104. FIG. 5 illustrates that during a test mode or to reposition or otherwise manipulate the leadless pacemaker 104 during deployment, the torque shaft 114 is torqueable and adjustable with a freedom of movement in a plurality of directions. The torque shaft 114 may be flexible and/or made from a variety of materials. For example, the torque shaft 114 may be made from a polymer, metal, and/or the like. The torque shaft 114 may be made with a catheter lamination construction, formed as a hollow helical cable, and/or in other configurations for torque transmission and steering. In one implementation, the torque shaft 114 and/or the steerable catheter 118 is a hypo tube. In other implementations, the torque shaft 114 and/or the steerable catheter 118 includes a cable tube, a laser cut tube, an extrusion, a wire, a wire cable, and/or the like for increased flexibility.

Figure 6:
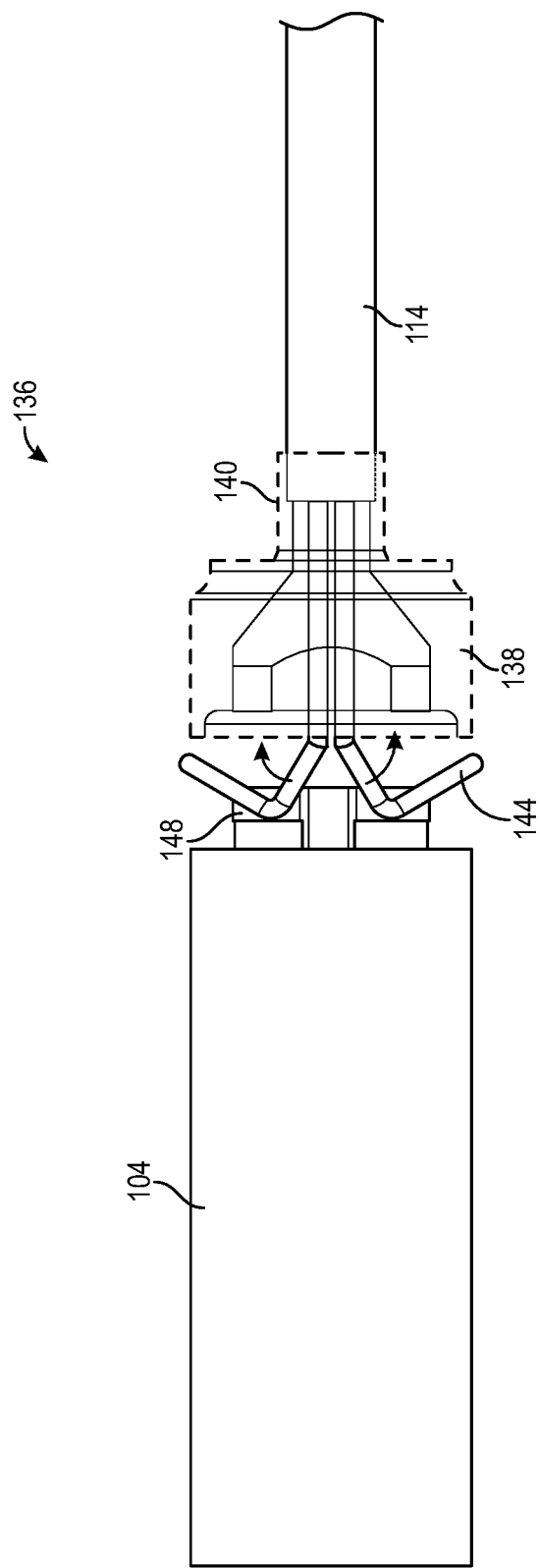
FIGS. 6 and 7 illustrate a side view and a perspective view of the retriever releasing or capturing the leadless pacemaker.
Figure 7:
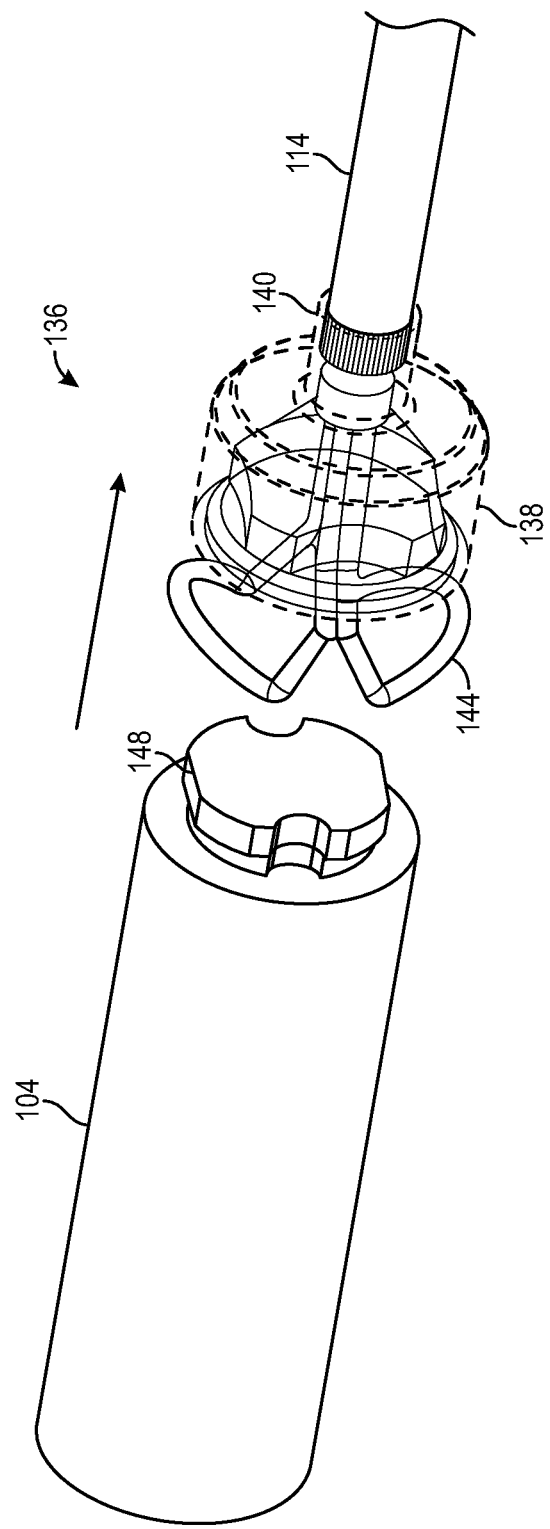

As can be understood from FIG. 6, the docking cap 136 is displaceable over the retriever 144 to cause the retriever 144 to move between an engaged position where the retriever 144 is engaged to the docking projection 148 within the chamber 142 and the catheter system 108 is docked to the leadless pacemaker 104 and a disengaged position where the retriever 144 is disposed in its natural state outside the chamber 142 and disengaged from the docking projection 148. As shown in FIGS. 6 and 7, in one implementation, the docking cap 136 is retracting proximally causing the retriever 144 to open radially to its natural state, thereby releasing the docking projection 148 and disengaging the leadless pacemaker 104. To recapture the leadless pacemaker for retrieval, repositioning, and/or the like, the retriever 144 is positioned relative to the docking projection 148 and the docking cap 136 is sheathed over the retriever 144 causing the retriever 144 to close radially over the docking projection 148 within the chamber 142.

In one implementation, the retriever 144 is a flexible grasper with a first arm disposed opposite a second arm that each form a hinge biased radially outwards from a longitudinal axis of the retriever 144. Stated differently, the retriever 144 is biased open in its natural state in free space, as shown in FIGS. 6 and 7. In one implementation, the natural state of the retriever 144 provides an opening defined by the arms with an inner diameter that is larger than a diameter of the docking projection 148 and in some examples a body of the leadless pacemaker 104. The retriever 144 in the form of a flexible grasper may be made from a variety of elastic or otherwise flexible materials, including, but not limited to, Nitinol or other memory wire, cable, tubing, and/or the like.

As can be understood from FIGS. 4A-7, the docking cap 136 translates axially over the retriever 144 to move the catheter system 108 between the docked and released positions. In one implementation, the body 138 of the docking cap 136 includes one or more cap surfaces disposed relative to the chamber 142. The cap surfaces displace the arms of the retriever 144 radially inwards to hold the arms in compression around the docking projection 148. As such, the docking cap 136 and the docking end of the leadless pacemaker 104 are configured such that the retriever 144 remains locked on the docking projection 148 when the docking cap 136 is sheathed over the retriever 144. This docked position facilitates delivery through the patient anatomy to a target location in the patient heart 102 for implantation. Once implanted, the docking cap 136 is retracted proximally, allowing the arms of the retriever 144 to open radially outwards to the natural state and thereby releasing the docking projection 148. The catheter system 108 is then removed from the patient. The docking projection 148 may be recaptured for retrieval or repositioning by sheathing the docking cap 136 over the retriever 144. During release and capture, tugging on or trauma to patient tissue is reduced or eliminated with the radial movement of the arms of the retriever 144 between the engaged and disengaged positions.

Figure 8:
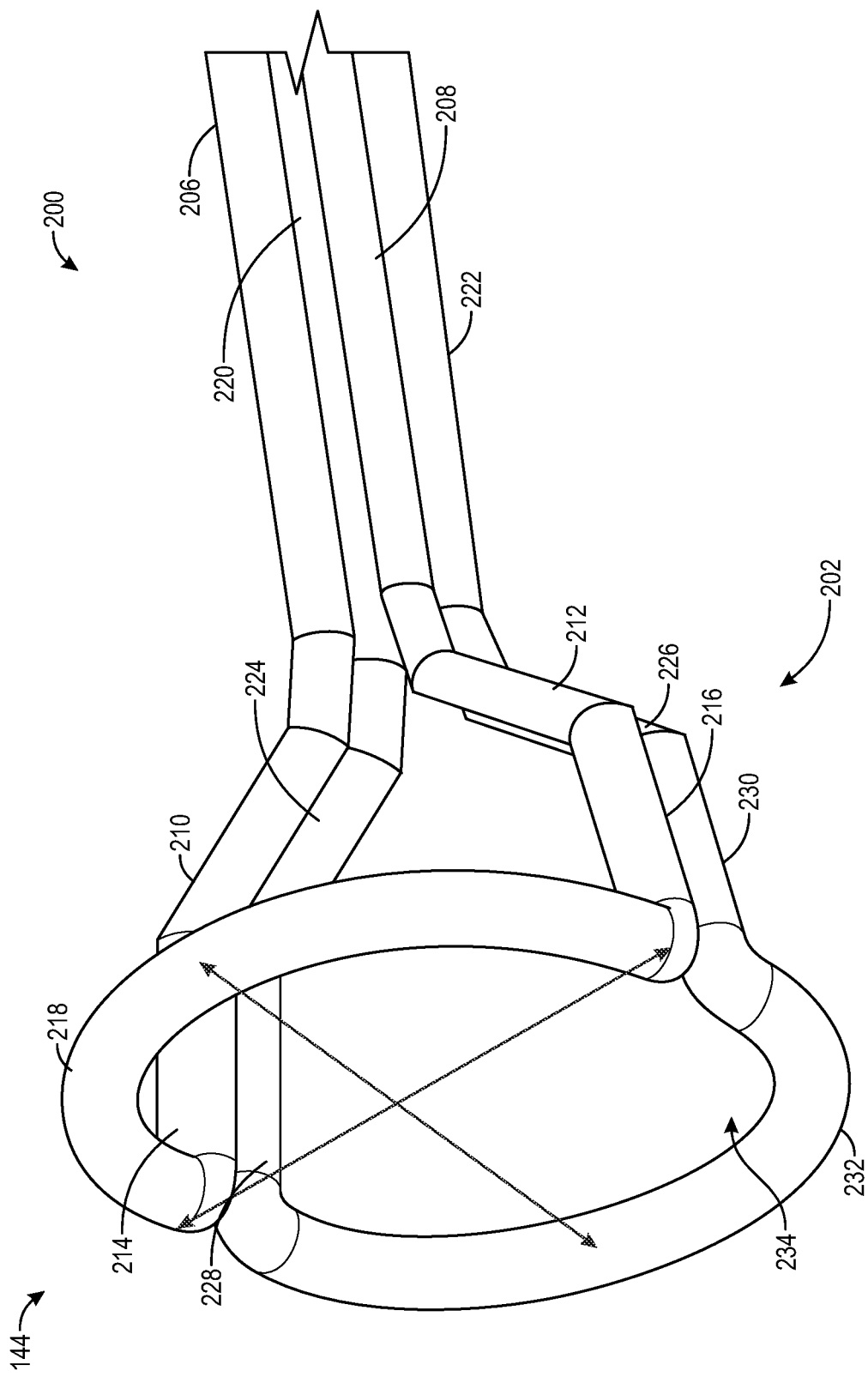
FIG. 8 shows the retriever in the form of an example of a flexible grasper adapted to open radially to release the leadless pacemaker.
Figure 9:
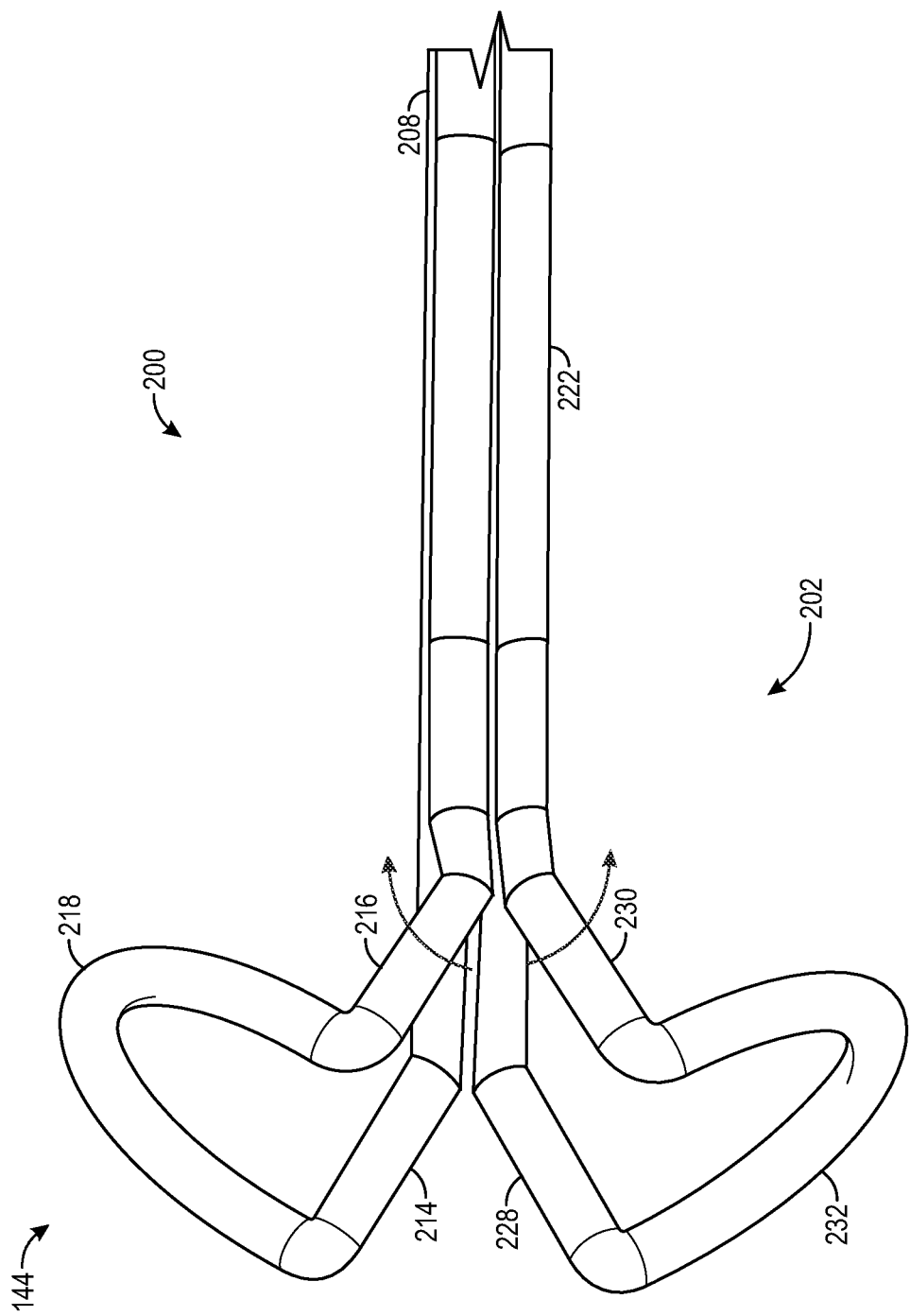
FIG. 9 shows the retriever in the form of another example of a flexible grasper adapted to hinge laterally to release the leadless pacemaker.

FIGS. 8 and 9 show examples of the retriever 144 in the form of a flexible grasper with a first arm 200 and a second arm 202 each forming a flexible loop attached to one or more mandrels extending through a lumen of the torque shaft 114. In one implementation, the first arm 200 includes one or more elongated bodies (e.g., a first elongated body 206 and a second elongated body 208). The first elongated body 206 may extend parallel to the second elongated body 208 within a first plane with a gap formed therebetween. A set of tapering portions connect the one or more elongated bodies to a set of grasping portions. In one implementation, a first grasping portion 214 is connected to the first elongated body 206 with a first tapering portion 210 on the first plane, and a second grasping portion 216 is connected to the second elongated body 208 with a second tapering portion 212 on the first plane. The first grasping portion 214 is generally parallel to the second grasping portion 216 and the first and second elongated bodies 206 and 208. A distance between the first and second grasping portions 214 and 216 is larger than a distance between the first and second elongated bodies 206 and 208, such that the first and second tapering portions 210 and 212 extend inwardly from the first and second grasping portions 214 and 216 to the first and second elongated bodies 206 and 208. The flexible loop of the first arm 200 is formed by a first looped portion 218 extending along a curve between the first and second grasping portions 214 and 216.

The second arm 202 may mirror the first arm 200. In one implementation, the second arm 202 includes one or more elongated bodies (e.g., a third elongated body 220 and a fourth elongated body 222). The third elongated body 220 may extend parallel to the fourth elongated body 222 within a second plane with a gap formed therebetween. The second plane is parallel to the first plane. A second set of tapering portions connect the one or more elongated bodies to a second set of grasping portions. In one implementation, a third grasping portion 228 is connected to the third elongated body 220 with a third tapering portion 224 on the second plane, and a fourth grasping portion 230 is connected to the fourth elongated body 222 with a fourth tapering portion 226 on the second plane. The third grasping portion 228 is generally parallel to the fourth grasping portion 230 and the third and fourth elongated bodies 220 and 222. A distance between the third and fourth grasping portions 228 and 230 is larger than a distance between the third and fourth elongated bodies 220 and 222, such that the third and fourth tapering portions 224 and 226 extend inwardly from the third and fourth grasping portions 228 and 230 to the third and fourth elongated bodies 220 and 222. The flexible loop of the second arm 202 is formed by a second looped portion 232 extending along a curve between the third and fourth grasping portions 228 and 230.

As can be understood from FIGS. 8 and 9, which show the docked position and the natural state of the retriever 144, respectively, in one implementation, the first arm 200 and the second arm 202 each form a hinge biased radially outwards from a longitudinal axis of the retriever 144. When the retriever 144 is in the docked position, the first set of grasping portions 214 and 216 are positioned adjacent the second set of grasping portions 228 and 230 within the first and second planes. In the docked position, the first and second looped portions 218 and 232 extend in opposite directions, forming a ring defining a docking space 234 therebetween. The docking space 234 may be sized and shaped to match a size and shape of the docking projection 148 with the first arm 200 and second arm 202 adapted to matingly engage the features of the docking projection 148 as described herein.

In moving to the natural state, the first arm 200 and the second arm 202 hinge radially outward from the longitudinal axis such that the first set of grasping portions 214 and 216 are positioned at an angle relative to the second set of grasping portions 228 and 230 with each at an angle relative to the first and second planes. In one implementation, when the docking cap 136 is retracted proximally, the ring formed by the first and second looped portions 218 and 232 opens radially outwards to a larger diameter, thus releasing the docking projection 148.

Figure 10A:
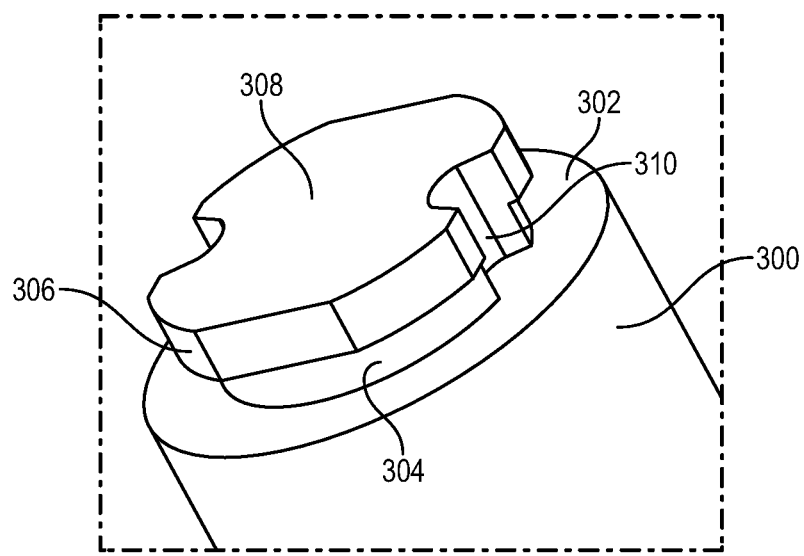
FIGS. 10A and 10B depict a perspective view and a back view, respectively, of an example docking end of a leadless pacemaker.
Figure 10B:
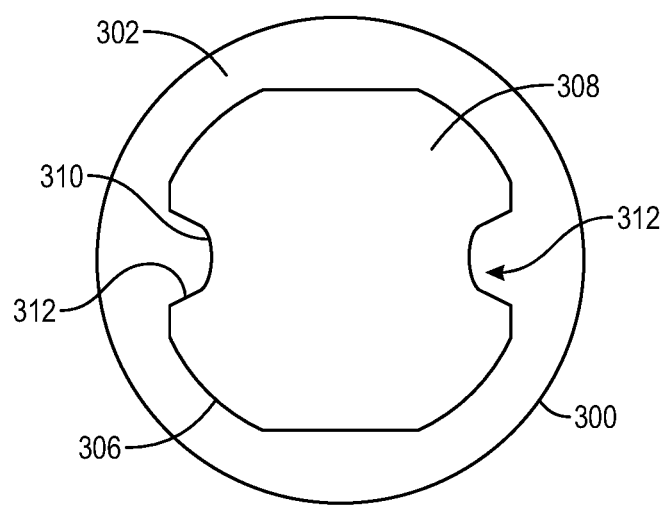

Turning to FIGS. 10A-10B, the docking projection 148 may include features adapted to matingly engage with the first arm 200 and the second arm 202 and the docking cap 136 to facilitate capture by the retriever 144 and to provide torque transmission. In one implementation, the leadless pacemaker 104 includes the docking projection 148 extending from a surface 302 at a docking end of a body 300. The docking projection 148 includes one or more docking surfaces, including edge docking surfaces 306, an end surface 308, and/or the like, configured to matingly engage corresponding cap surfaces disposed relative to the chamber 142 of the docking cap 136, thereby providing torque transmission to the leadless pacemaker 104. In one implementation, the edge docking surfaces 306 include one or more flat radial surfaces that may be radially symmetrical about the docking projection 148. The edge docking surfaces 306 may be disposed relative to the end surface 308 forming a ledge extending transverse to the end surface 308. In one implementation, the end surface 308 is flat and the surface 302 of the body 300 is flat providing additional surfaces for torque transmission.

Figure 11:
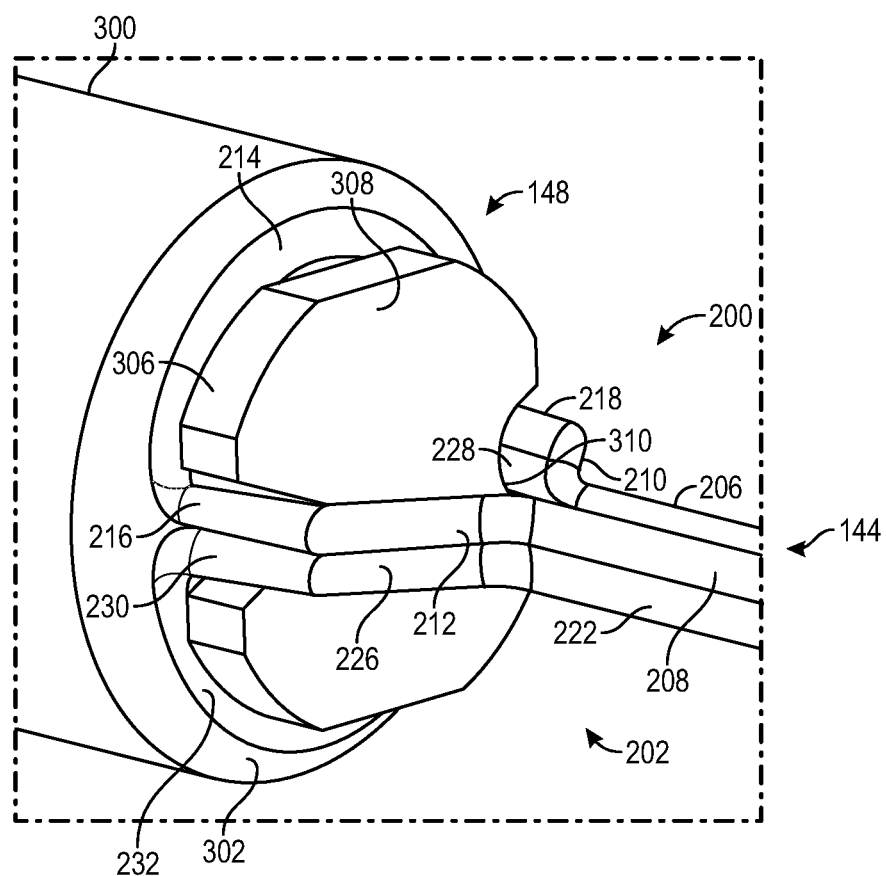
FIG. 11 illustrates an example flexible grasper engaged to a docking projection of a leadless pacemaker.

The docking surfaces may include one or more keys adapted to matingly engage corresponding features of the docking cap 136 and/or the retriever 144. The docking projection 148 and/or the surface 302 of the docking end of the body 300 may include one or more of the keys. In one implementation, the docking projection 148 includes side keys 310 extending through the docking projection 148 from the surface 302 of the body 300 to the end surface 308. The side keys 310 may be oriented relative to each other on opposite sides, such that they are radially symmetric. As shown in FIG. 11, in one implementation, the side keys 310 are adapted to matingly engage a portion of the first arm 200 and the second arm 202 of the retriever 144 in the engaged position. For example, the grasping portions 214, 216, 228, and 230 may be displaced during sheathing of the docking cap 136 into the side keys 310 where the docking cap 136 holds them in place in the engaged position. The side keys 310 may include one or more key surfaces 312 for torque transmission via the first arm 200 and the second arm 202 of the retriever 144.

Similarly, the docking projection 148 may include a neck 304 indented from the edge docking surfaces 306 and adapted to matingly engage at least a portion of the first arm 200 and the second arm 202 of the retriever 144. For example, the docking cap 136 may hinge the first and second looped portions 214 and 232 radially inwards into the neck 304, where the docking cap 136 holds the first and second looped portions 214 and 232 in compression around the docking projection 148 in the engaged position. The indentation of the neck 304 prevents the first and second arms 200 and 202 from translating longitudinally and disengaging from the docking projection 148. The geometry of the docking projection 148 facilitates a smooth capture and release by the retriever 144 when the docking cap 136 is sheathed distally or retracted proximally.

Figure 12:
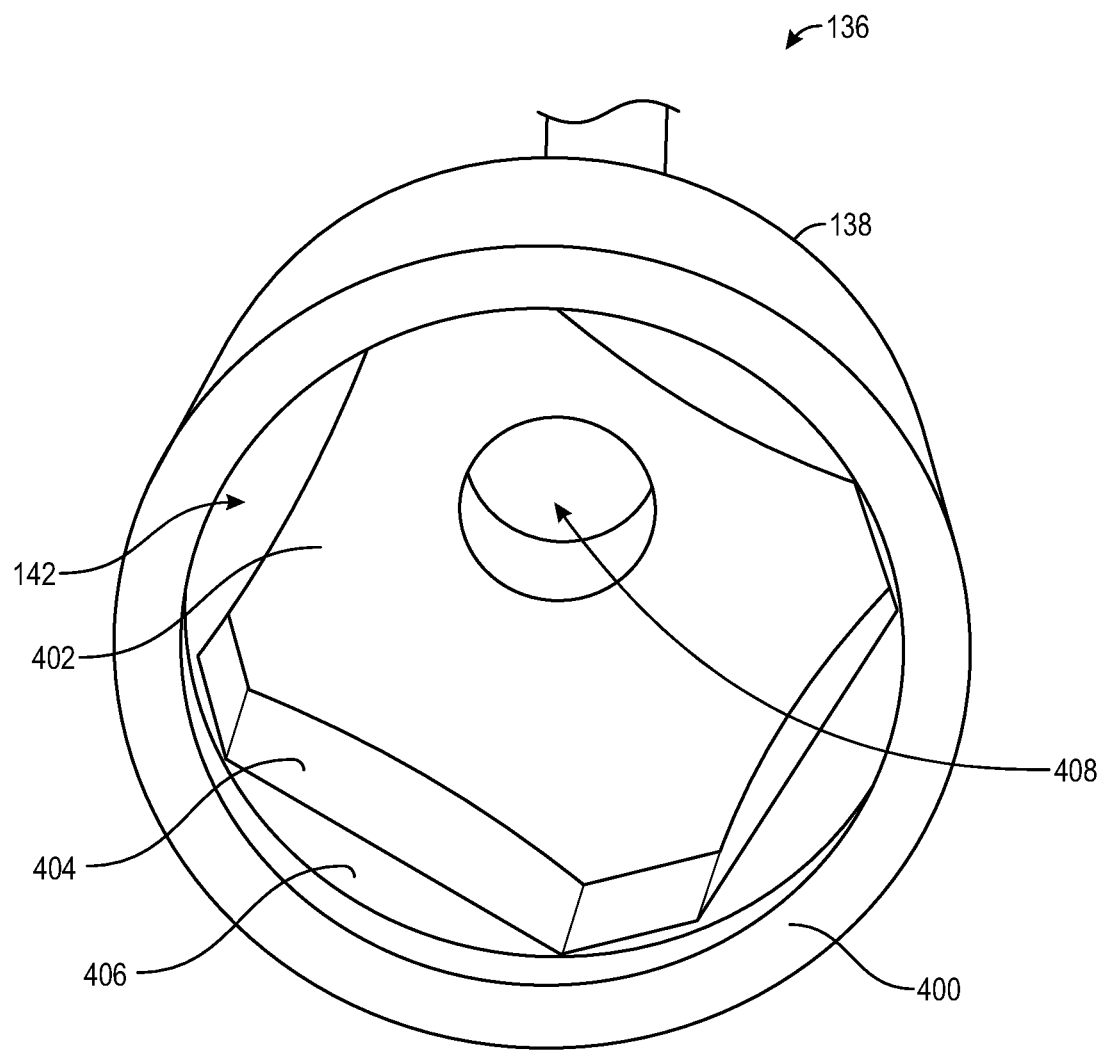
FIG. 12 shows a perspective front view of an example docking cap.

Referring to FIG. 12, the body 138 of docking cap 136 includes one or more cap surfaces disposed relative to the chamber 142 adapted to matingly engage the docking surfaces of the docking end of the leadless pacemaker 104 and/or features of the retriever 144. In one implementation, the one or more cap surfaces include a distal end surface 400, a proximal chamber surface 402, and one or more side surfaces 404 extending between the proximal chamber surface 402 and one or more ledge surfaces 406 disposed proximal to the distal end surface 400 within the chamber 142. The distal end surface 400 defines an opening into the chamber 132, and the proximal chamber surface 402 defines a proximal opening 408 into the chamber 142 extending through the receiving portion 140. The proximal opening 408 is coaxial with the longitudinal axis of a lumen of the torque shaft 114 and the retriever 144.

The ledge surfaces 406 may mirror a size and shape of the surface 302 of the docking end of the body 300 of the leadless pacemaker 104. For example, both the ledge surfaces 406 and the surface 302 may be flat. Similarly, the proximal chamber surface 402 may be sized and shaped to matingly engage the end surface 308 of the docking projection 148, and the side surfaces 404 matingly engage the edge docking surfaces 306. The mating engagement of each of the various cap surfaces with the corresponding docking surfaces provides torque transmission. When in the docking position, the engagement of the docking projection 148 with the docking cap 136 generates approximately 1.5 in-oz of torque with a mating normal force of approximately 500 g. The torque generated is thus an order of magnitude higher than the 0.125 in-oz or less of torque generally needed to implant a leadless pacemaker into human tissue.

Figure 13:
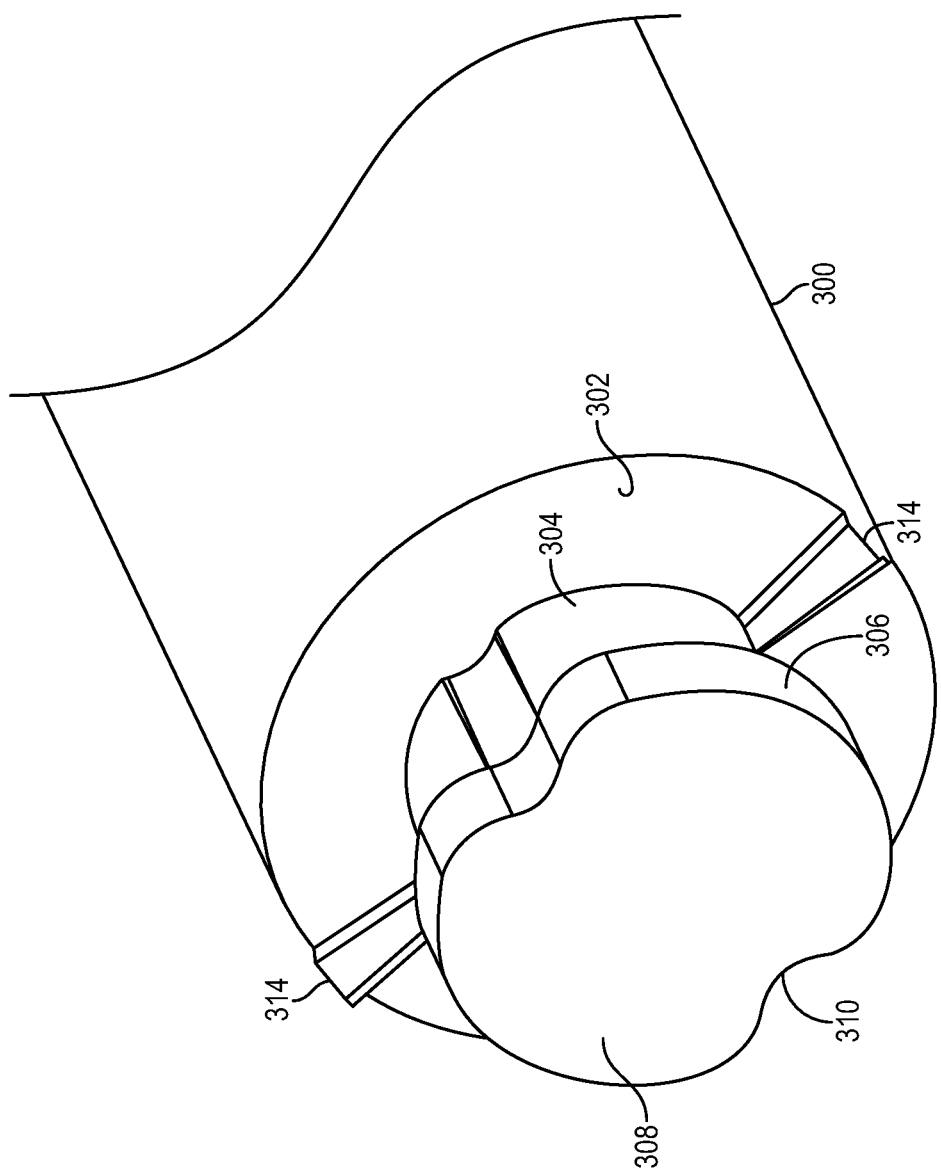
FIG. 13 shows a docking end of a leadless pacemaker with example keys defined in a surface.
Figure 14A:
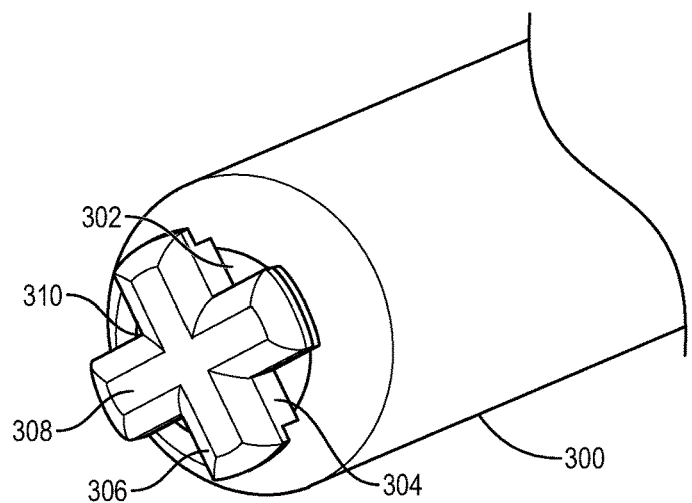
FIGS. 14A and 14B are perspective and top views, respectively, of an example docking projection having a cross shape.
Figure 14B:
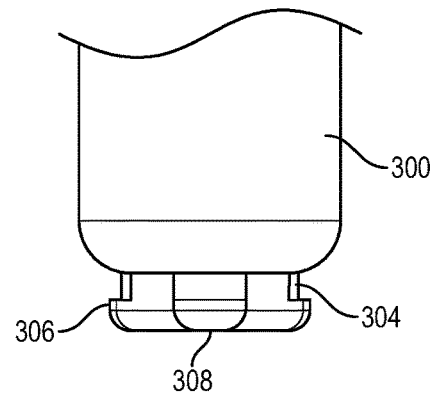
Figure 14C:
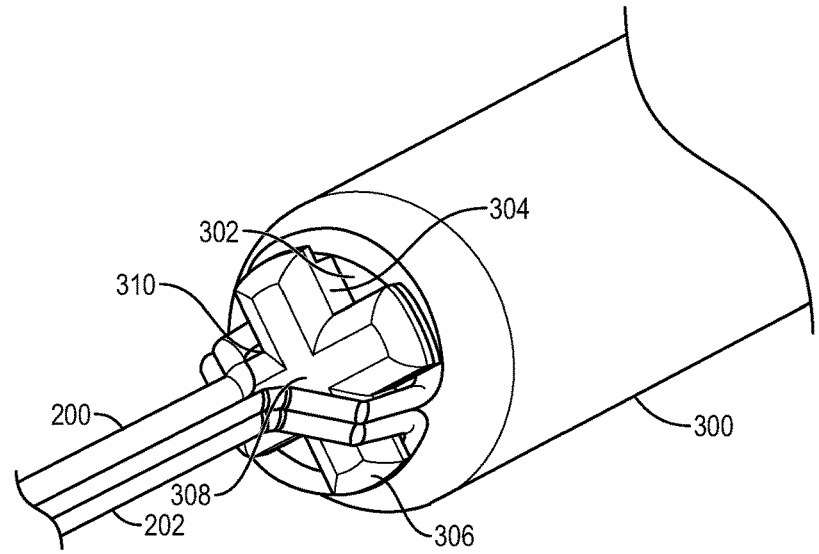
FIG. 14C illustrates a flexible grasper engaged to the docking projection of FIGS. 14A-14B.
Figure 16A:
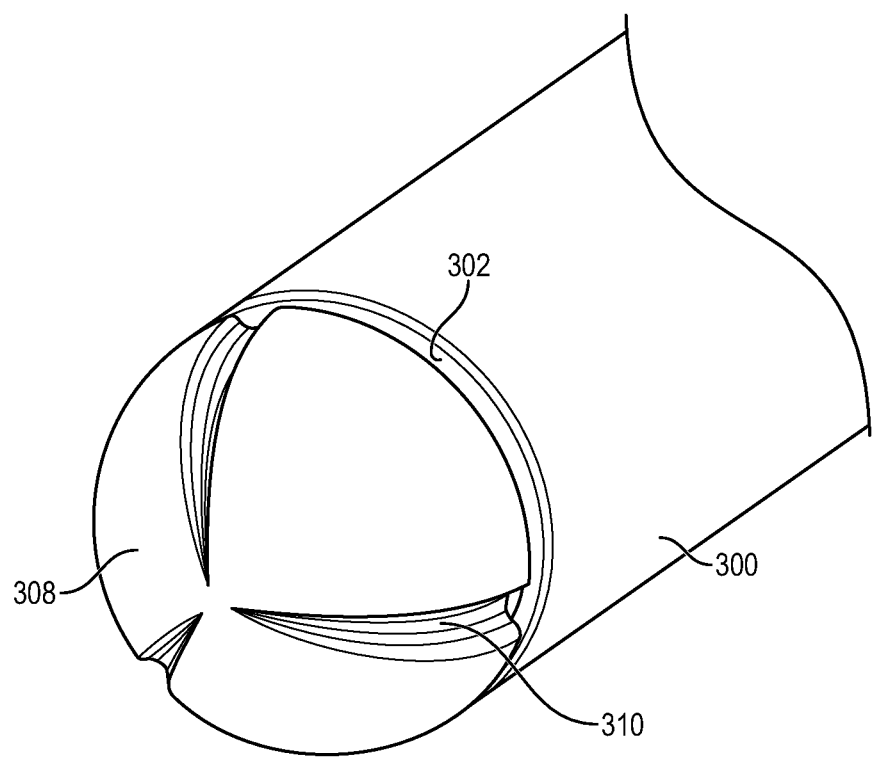
FIGS. 16A and 16B illustrate a perspective view and a top view, respectively, of an example set of keys defined in a surface of the docking projection.
Figure 16B:
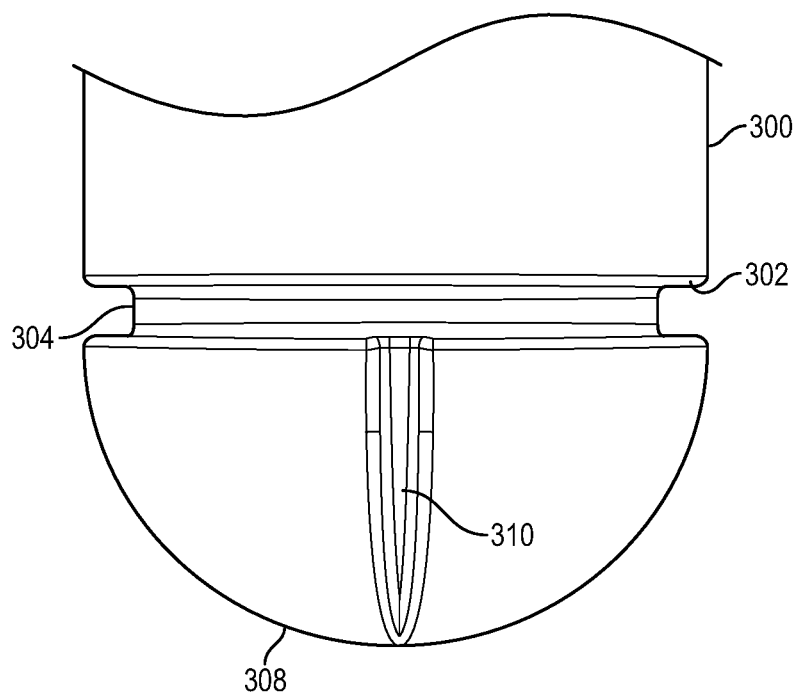

Examples of various geometries of the docking end of the leadless pacemaker 104 are shown in FIGS. 13-18. The geometries include one or more keys in the form of torque transmission keys, dimples, and/or geometric interference features that matingly engage with corresponding features on the docking cap 136. Turning first to FIG. 13, in one implementation, the surface 302 of the body 300 includes one or more undercut keys 314 defined therein. Alternatively or additionally, the docking projection 148 may have a cross-shape as shown in FIGS. 14A-14C with the side keys 310 forming angled cutouts.

In another implementation, the end surface 308 of the docking projection 148 is rounded, as shown in FIGS. 15A-18. A profile of the end surface 308 may have a variety of lengths from a lower profile curve to a higher dome shaped profile, each with the end surface 308 being a non-traumatic smooth round surface. The docking cap 136 includes corresponding cap surfaces mirroring the size and shape of the end surface 308 to hold the retriever 144 in compression against the docking projection 148 in the engaged position. Frictional contact between the cap surfaces and the end surface 308 provide torque transmission. To further facilitate torque transmission, the end surface 308 may include the keys 310 adapted to matingly engage cap keys 410, as can be understood from FIGS. 16A-18. To increase the friction of the mating surfaces, an overmolding 412 made from silicone or a similar material may be applied to the cap surfaces within the chamber 142 and/or on the docking projection 148, as shown in FIGS. 19A-19B.

Figure 17A:
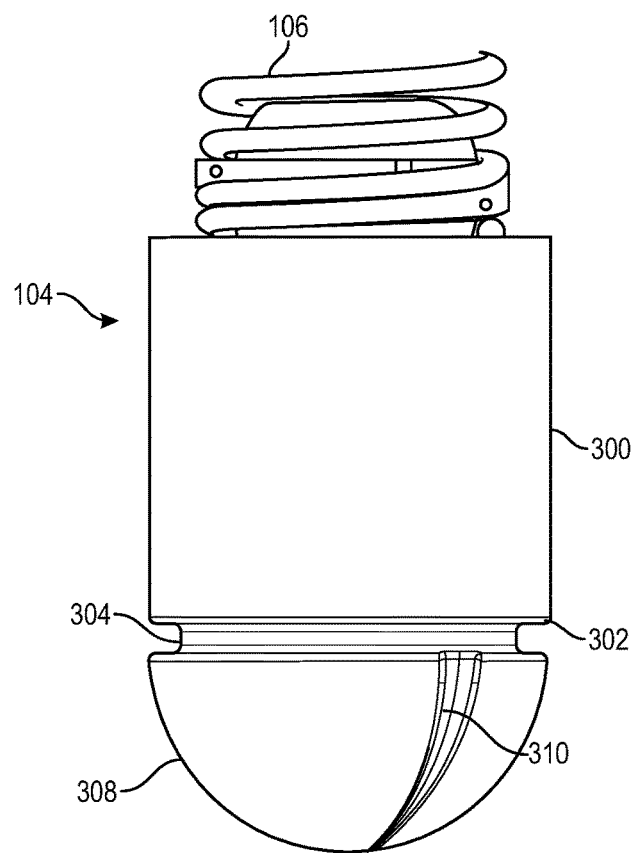
FIGS. 17A and 17B show a top view and a perspective view of an example leadless pacemaker having a round docking projection with a set of keys.
Figure 17B:
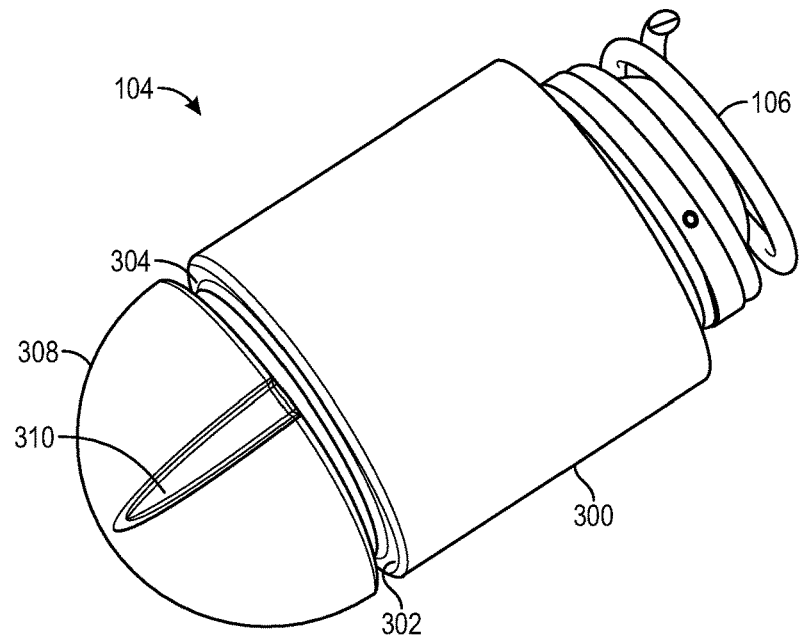
Figure 18:
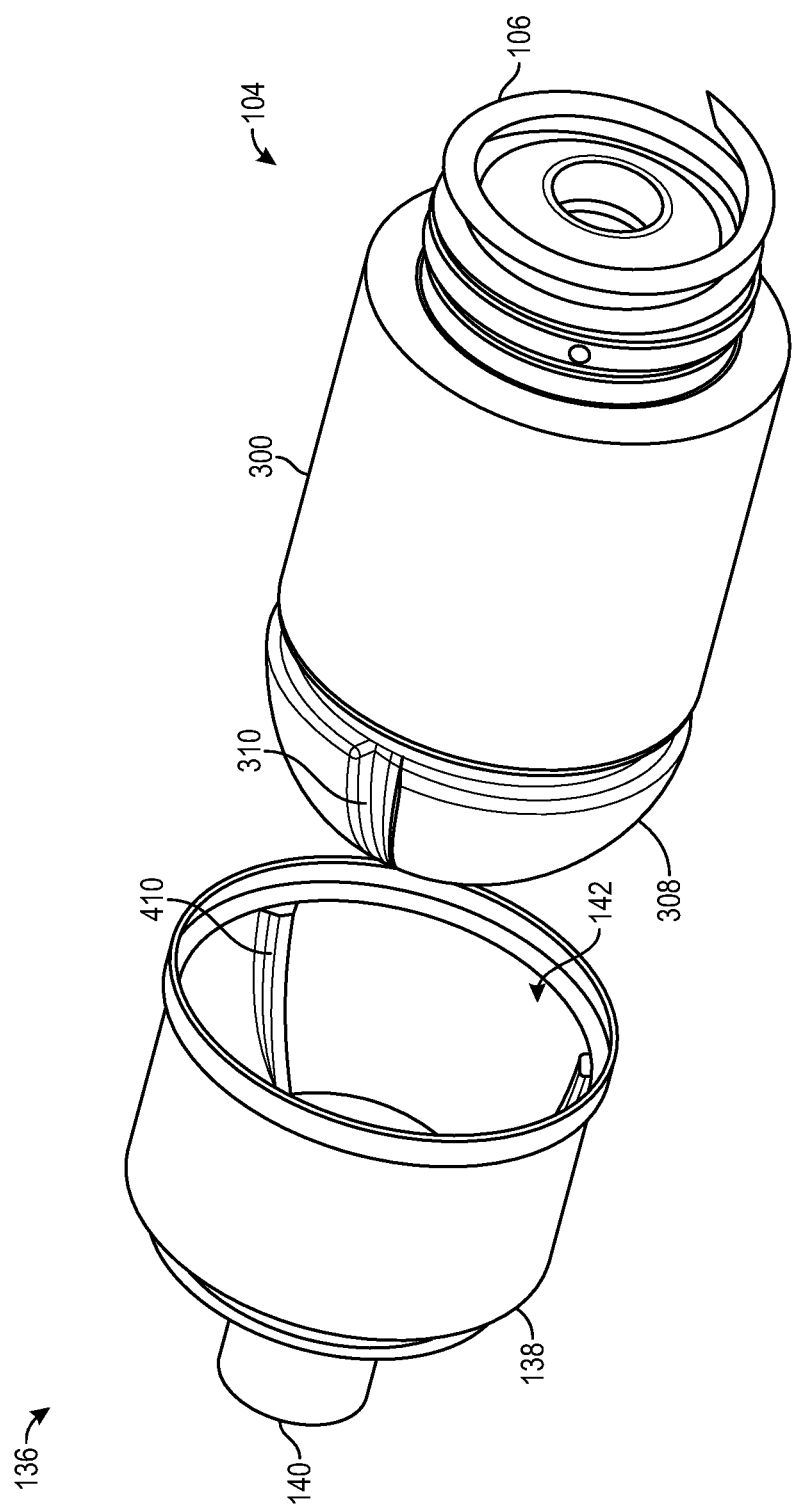
FIG. 18 depicts an example docking cap disposed relative to an example leadless pacemaker, the docking cap including one or more cap surfaces configured to mating engage one or more docking surfaces of the docking projection.
Figure 19A:
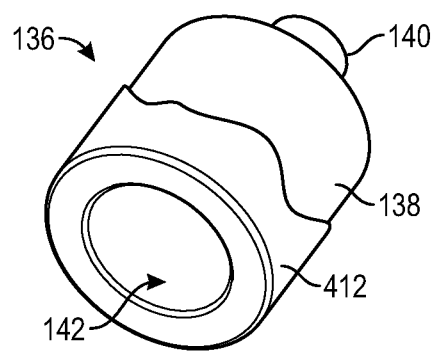
FIGS. 19A and 19B illustrating an example docking cap released from and engaged to a leadless pacemaker, respectively, the docking cap having an overmolding configured to transfer torque via increased friction between the docking cap and the leadless pacemaker.
Figure 19B:
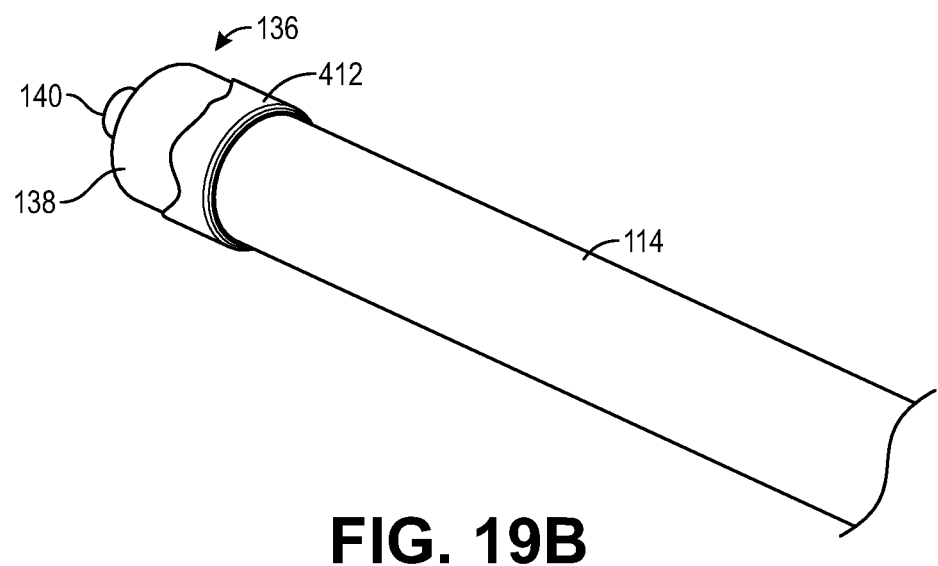

Referring to FIGS. 17A-18, the helical anchor 106 is disposed on a fixing end of the leadless pacemaker 104 opposite the docking end. In one implementation, the fixing end is at the distal end of the leadless pacemaker 104, and the docking end is at the proximal end. It will be appreciated that some or all of these features may be reversed (stand-proud of their surface) depending on size restraints of the leadless pacemaker 104.

Figure 20:
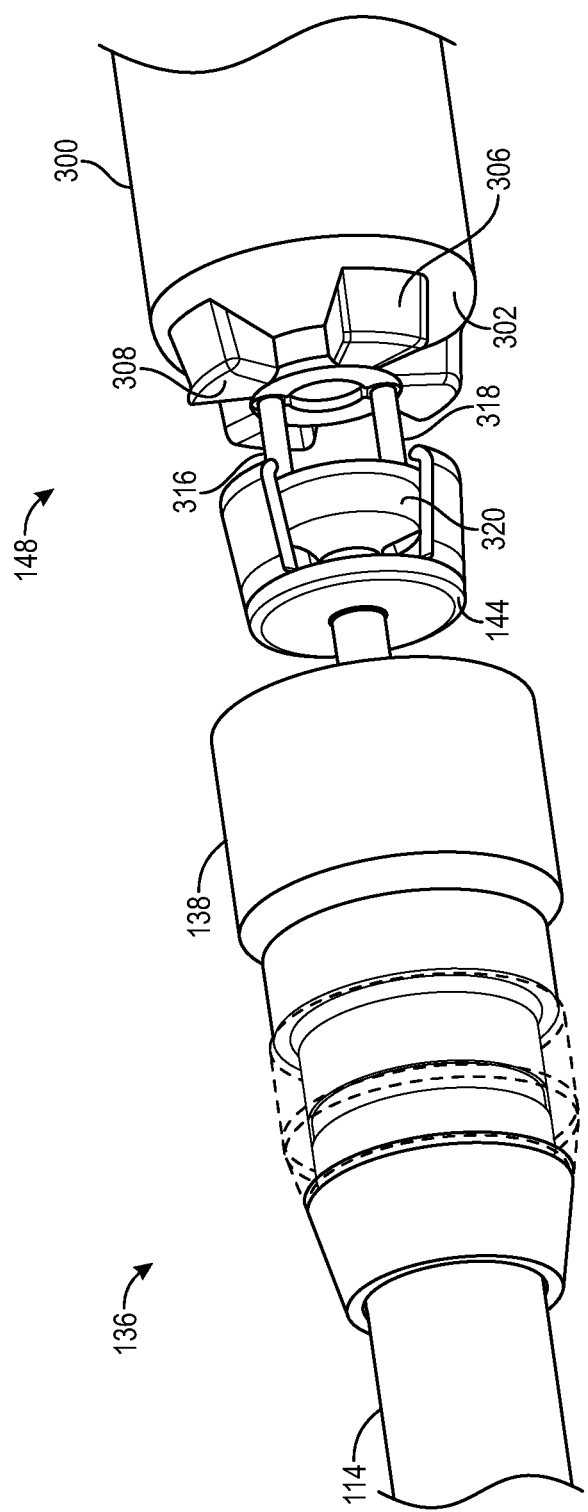
FIG. 20 illustrates another example retriever in the form of a flexible grasper engagable to a docking button.

For a detailed description of another example of the retriever 144 in the form of a flexible grasper and a corresponding example of the docking projection 148, reference is made to FIGS. 20-26C. Turning first to FIG. 20, in one implementation, the docking projection 148 includes a docking button 320 mounted to the end surface 308 with one or more posts (e.g., first and second posts 316 and 318). As can be understood from FIG. 21, the docking button 320 may be integral with the posts 316 and 318 and be a rounded surface extending between a first end 322 and a second end 324.

Figure 21:
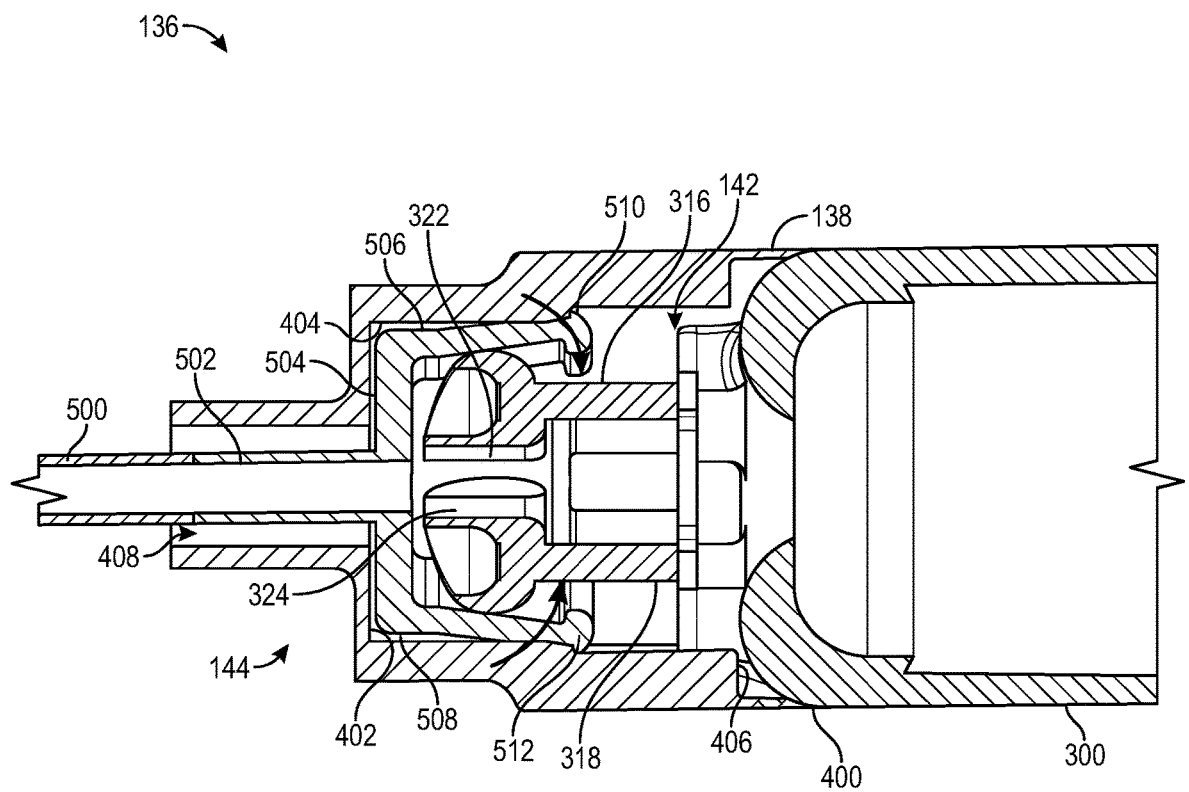
FIG. 21 is a cross-section of a docking cap holding arms of a flexible grasper in compression around a docking button within a chamber.
Figure 22:
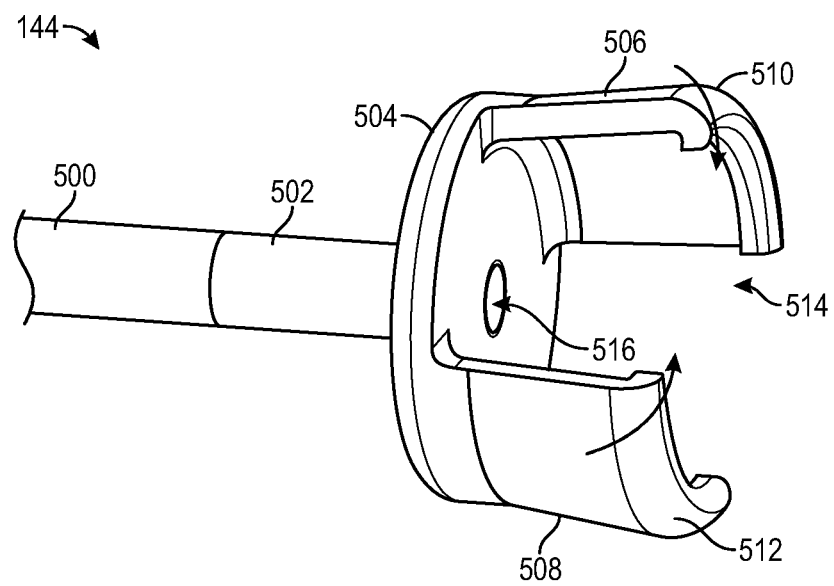
FIG. 22 is a detailed view of an example flexible grasper.

As shown in FIGS. 21 and 22, the retriever 144 includes a mandrel 500 connected to a base 504. The mandrel 500 may be connected directly to the base 504 or indirectly via a retriever shaft 502. The mandrel 500 extends through the proximal opening 408 and into the lumen of the torque shaft 114. The retriever 144 may be made from a variety of elastic or otherwise flexible materials, including, but not limited to, a polymer (e.g., polyether ether ketone (PEEK)), Nitinol or other memory wire, cable, tubing, and/or the like.

The retriever 144 includes a first arm 506 and a second arm 508 extending from the base 504 and defining a docking space 514 therebetween. In one implementation, the first and second arms 506 and 508 form a jaw with hinges adapted to grasp at least a portion of the docking projection 148, such as the docking button 320, in the docking space 514 when the docking cap 136 is sheathed over retriever 144 into the docked position. In another implementation, one or more hinges are disposed at the connection points between the arms 506 and 508 and the base 504. The first arm 506 may include a first lip 510, and the second arm 508 may include a second lip 512. Each of the lips 510 and 512 extends inwardly towards a longitudinal axis of a lumen 516 of the retriever 144.

Figure 23:
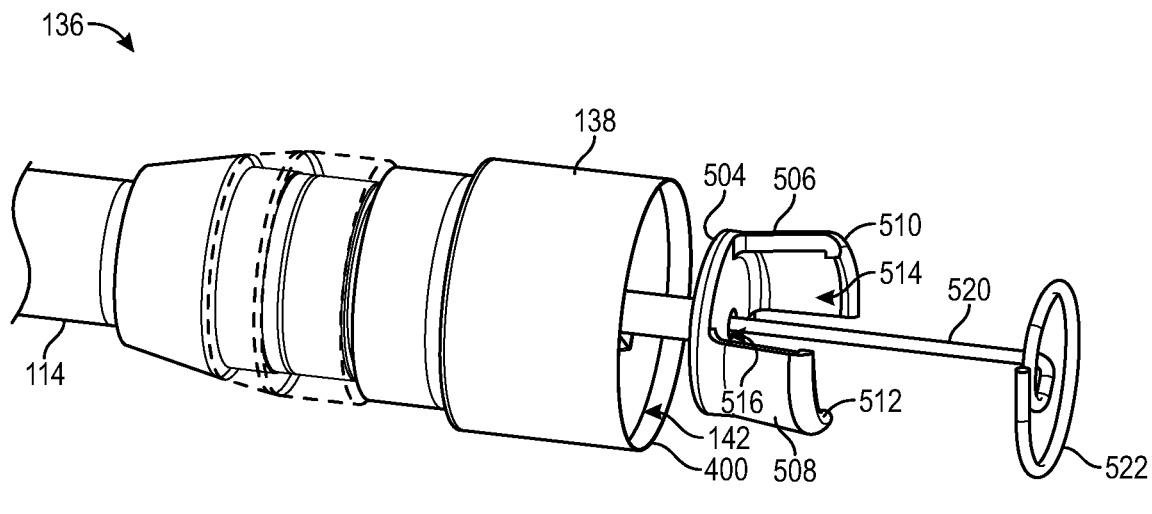
FIG. 23 shows a tether extending through a lumen of an example flexible grasper.

As illustrated in FIG. 23, in one implementation, a tether 518 may be introduced during a tether mode or test mode to check for thresholds, among other reasons. The tether 518 may be, without limitation, a snare, a flexible shaft, and/or the like. For example, the tether 518 may include an elongated body 520 extending distally through the lumen 516 of the retriever 144 to a distal loop 522.

Figure 24:
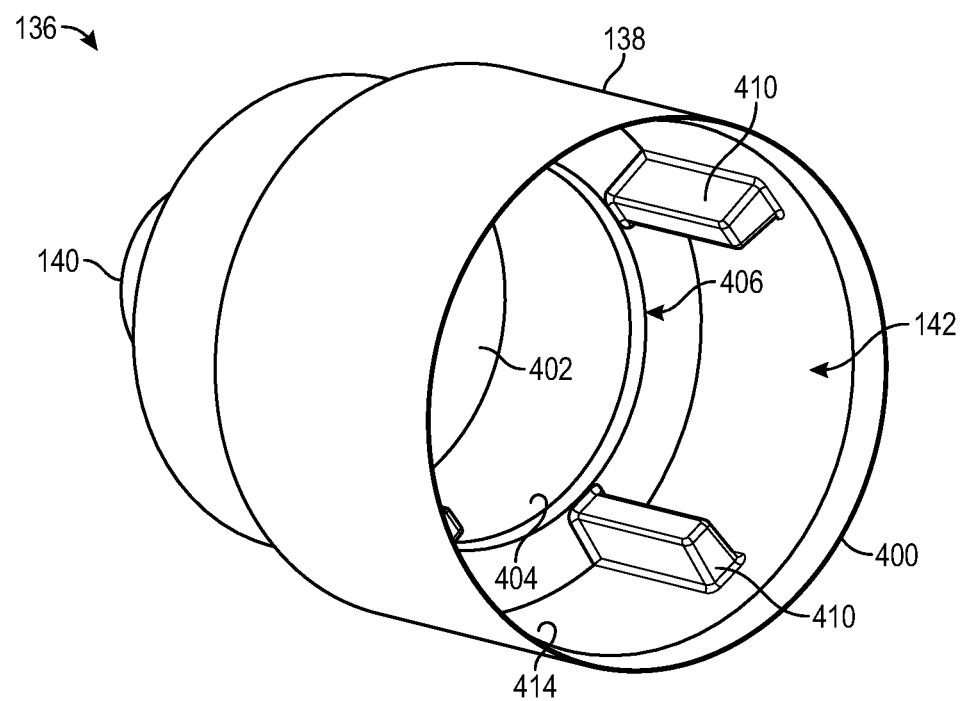
FIG. 24 depicts an example docking cap.

Turning to FIG. 24, another example of the docking cap 136 is shown. The body 138 of the docking cap 136 includes one or more cap surfaces, as described herein, adapted to provide torque to the leadless pacemaker 104 via the docking surfaces of the docking end of the leadless pacemaker 104, as well as to move the first arm 506 and the second arm 508 to the engaged position around the docking projection 148. In one implementation, the one or more cap surfaces are disposed relative to the chamber 142 and are adapted to matingly engage the docking surfaces and/or features of the retriever 144. The one or more cap surfaces may include the distal end surface 400, the proximal chamber surface 402, and the side surface 404 extending between the proximal chamber surface 402 and the ledge surface 406, which is disposed proximal to the distal end surface 400 within the chamber 142. The distal end surface 400 defines an opening into the chamber 132, and the proximal chamber surface 402 defines the proximal opening 408 into the chamber 142 extending through the receiving portion 140. The proximal opening 408 is coaxial with the longitudinal axis of a lumen of the torque shaft 114 and/or the steerable catheter 118 and the lumen 516 of the retriever 144.

The ledge surface 406 may mirror a size and shape of the surface 302 of the docking end of the body 300 of the leadless pacemaker 104. For example, both the ledge surface 406 and the surface 302 may be flat. The mating engagement of each of the various cap surfaces with the corresponding docking surfaces provides torque transmission. To further facilitate torque transmission, one or more of the cap surfaces may include the cap keys 410. In one implementation, the cap keys 410 are disposed radially around a distal side surface 414 extending from the ledge surface 406 towards the distal end surface 400. The cap keys 410 may be adapted to matingly engage corresponding side keys 310 defined in the docking projection 148 for torque transmission.

Figure 25A:
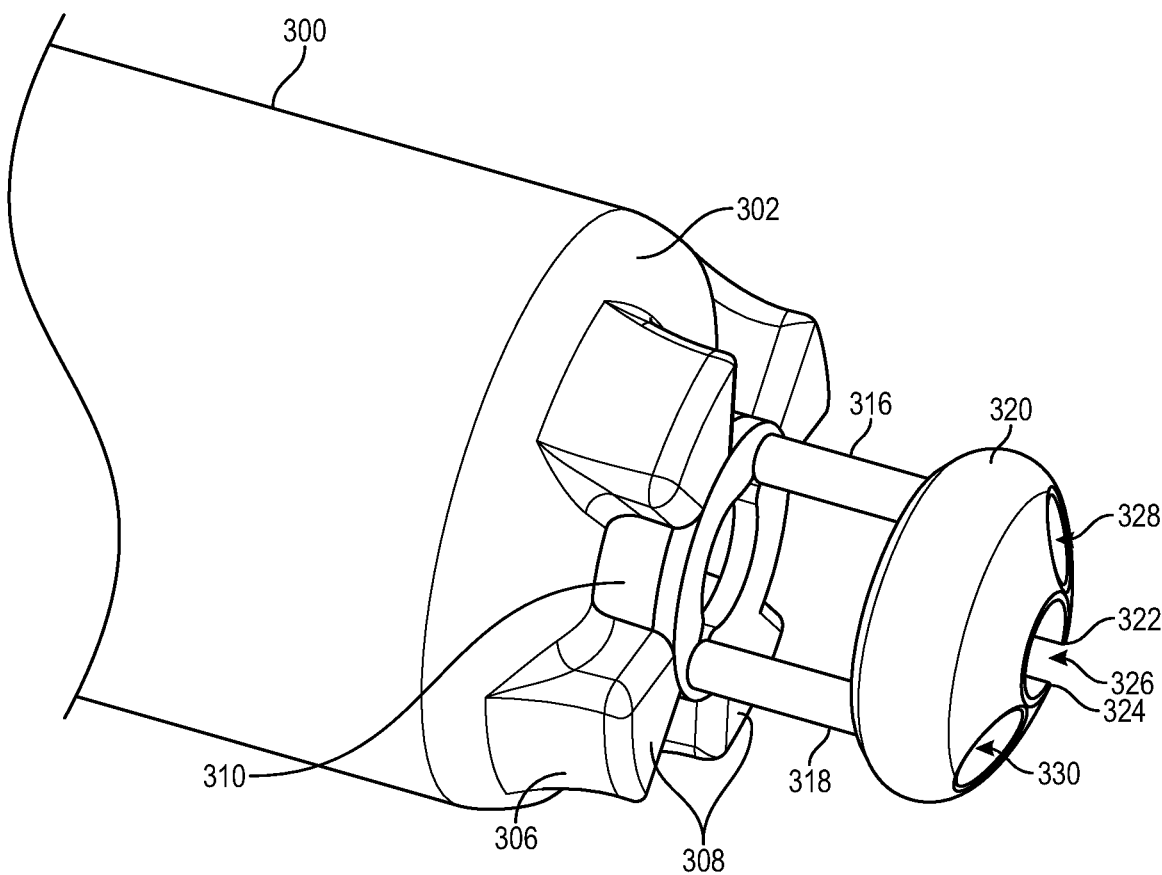
FIGS. 25A and 25B illustrate a rigid docking button and a flexible docking button, respectively.
Figure 25B:
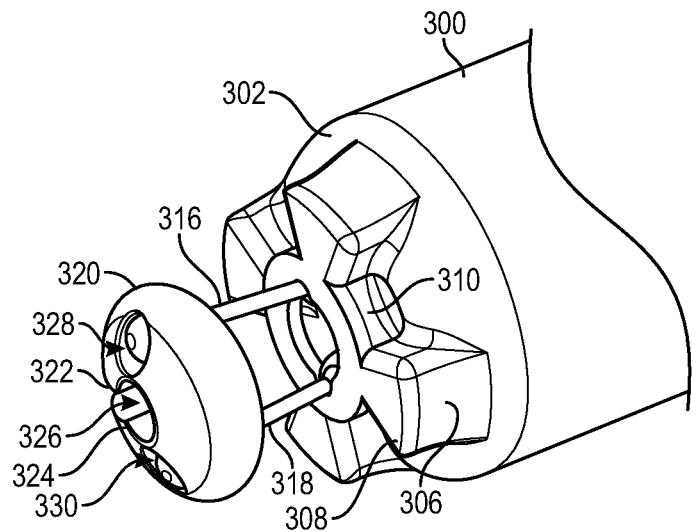

Additional examples of the docking projection 148 are shown in FIGS. 25A-25B. In one implementation, the side keys 310 are defined in the edge docking surfaces 306 of the docking projection 148 extending from the surface 302 of the body 300 to the end surface 308. The side keys 310 may be oriented relative to each other on opposite sides, such that they are radially symmetric. In one implementation, the cap 136 is adapted to matingly engage the docking projection 148 with the edge docking surfaces 306 disposed along the distal side surface 414 and the cap keys 410 disposed within the side keys 310.

The ledge surface 406 may be adapted to displace the first arm 506 and the second arm 508 radially inward from their natural state in which they are biased radially outwards. In one implementation, the ledge surface 406 displaces the first and second arms 506 and 508 until they close around the docking button 320 in the engaged position shown in FIG. 21. The side surface 404 holds the first and second arms 506 and 508 around the docking button 320 with the first and second lips 510 and 512 extending inwardly past an outer edge of the docking button 320, preventing the docking button 320 from translating distally out of the docking space 514 and thus releasing from the retriever 144.

The docking button 320 may be mounted to the end surface 308 with the first and second posts 316 and 318. As can be understood from FIG. 25A-25B, the docking button 320 may be integral with, connected rigidly to, and/or connected flexibly to the posts 316 and 318. In one implementation, the docking button 320 is a rounded surface extending between the first end 322 and the second end 324, which are separated by a gap opening into a button lumen 326. The docking button 320 includes a first slot 328 and a second slot 330 adapted to receive and engage the first and second posts 316 and 318, respectively.

Figure 26A:
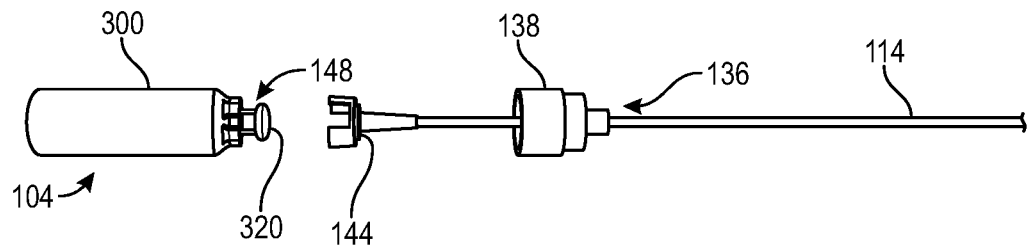
FIG. 26A shows a flexible grasper disposed relative to a docking button of a leadless pacemaker.
Figure 26B:
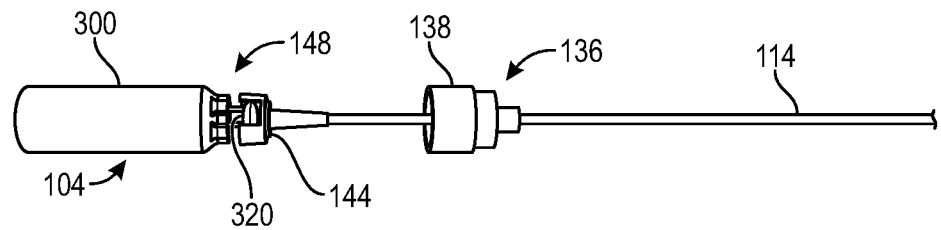
FIG. 26B illustrates the docking button positioned between a first arm and a second arm of the flexible grasper.
Figure 26C:
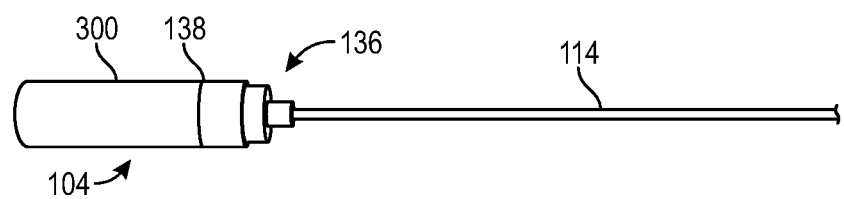
FIG. 26C shows a docking cap sheathed over the flexible grasper and holding the first arm and the second arm in compression around the docking button.

For a detailed description of docking and releasing the leadless pacemaker 104 for delivery and/or retrieval, reference is made to FIGS. 26A-26C. In one implementation, the retriever 144 is disposed relative to the docking projection 148. FIG. 26A illustrates the retriever 144 approaching the docking projection 148 for engagement. The docking projection 148 is positioned in the docking space 514 between the first and second arms 506 and 508. For example, the docking button 320 of the docking projection 148 may be positioned within the docking space 514, as shown in FIG. 26B. The body 138 of the docking cap 136 is sheathed over the retriever 144 until the docking end of the leadless pacemaker 104 including the docking projection 148 is disposed within the chamber 142. The docking cap 136 holds the retriever 144 in compression around the docking button 320 locking the leadless pacemaker 104 in the docked position shown in FIG. 26C. The leadless pacemaker 104 is thus docked to the catheter system 108 and prepared for delivery through the patient anatomy to the implant site, for example, within the patient heart 102. The engagement of the docking cap 136 with the docking end of the leadless pacemaker 104 may be strong enough to maintain the leadless pacemaker 104 in the docked position against the force of gravity.

Once disposed within the implant site, the catheter system 108 is rotated using the handle body 122. The mating engagement of the one or more cap surfaces with the one or more docking surfaces transmits the torque of this rotation to the leadless pacemaker 104 to fix the leadless pacemaker 104 to the tissue at the implant site using the helical anchor 106. In some implementations, the tether 518 is used to check for thresholds. Once the leadless pacemaker 104 is fixed in the implant site, the catheter system 108 releases the leadless pacemaker 104. In one implementation, the body 138 of the docking cap 136 is retracted proximally until the retriever 144 is outside the chamber 142, causing the first arm 506 and the second arm 508 to spring open in a direction radially outwardly, thereby releasing the docking button 320. The catheter system 108 is then retracted along the patient anatomy and removed from the body.

During retrieval, the catheter system 108 is introduced into the body and advanced through the patient anatomy to the implant site until the retriever 144 is disposed relative to the docking projection 148. The retriever 144 is advanced until the docking button 320 is positioned within the docking space 514 between the first and second arms 506 and 508. The body 138 of the docking cap 136 is sheathed over the retriever 144, locking the leadless pacemaker 104 to the catheter system 108 in the docked position, as described herein. The catheter system 108 is then rotated with the mating engagement of the docking projection 148 with the docking cap 136 transmitting the torque to the leadless pacemaker 104 to unfix the helical anchor 106 from the tissue. The retriever 144 or other features of the catheter system 108, such as a cutting edge, may be used to remove any tissue overgrowth on the leadless pacemaker 104. The leadless pacemaker 104 is maintained in the docked position and the catheter system 108 is retracted through the patient anatomy to retrieve the leadless pacemaker 104.

Figure 27:
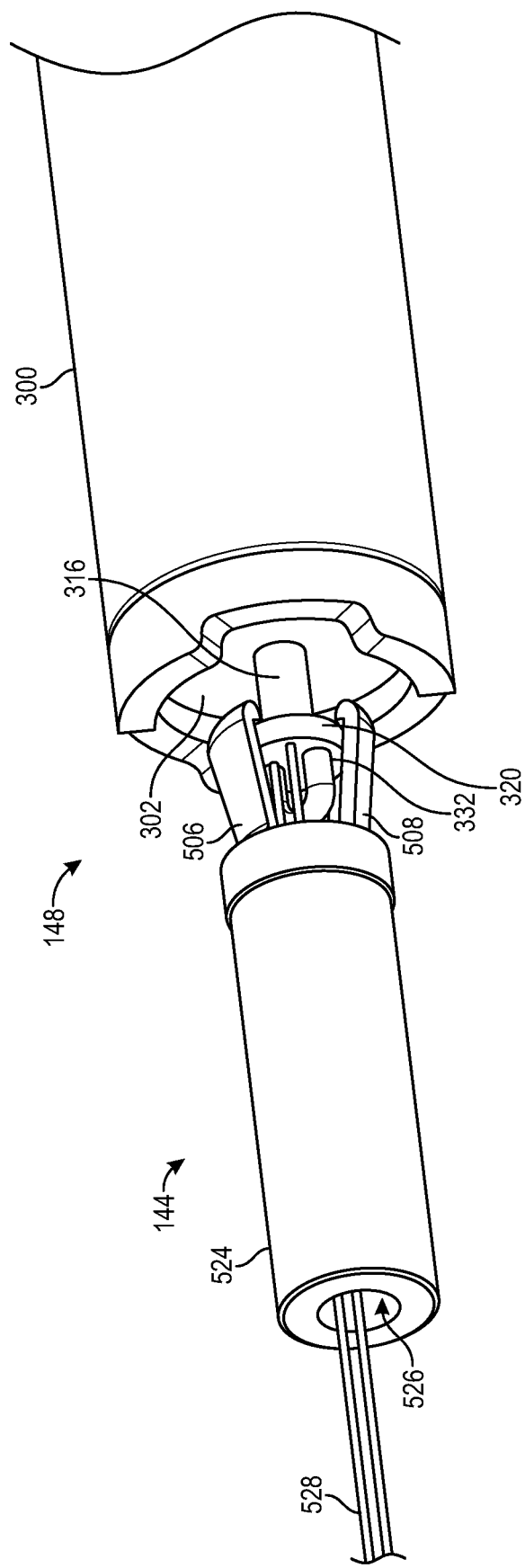
FIG. 27 illustrates an example docking projection having a loop configured to receive a tether, a snare, or a cable.

For another example of a docking cap adapted to lock the retriever 144 in the engaged position around the docking projection 148, reference is made to FIG. 27. In one implementation, the docking cap includes an elongated body 524 with a lumen 526 defined therein. A tether 528, which may be a snare, cable, or other tether, extends through the lumen 526 of the elongated body 526, as well as the lumen 516 of the retriever 144. The tether 528 may be looped through the docking projection 148 and taken back to the handle body 122 of the catheter system 108.

In one implementation, the docking projection 148 of the leadless pacemaker 104 includes the docking button 320 attached to the surface 302 of the body 300 of the leadless pacemaker 104 with the post 316. The docking button 320 includes a flat distal surface from which a hook 332 extends. The tether 528 may be looped through the hook 332.

As shown in FIG. 20, to engage the retriever 144 in the docked position with the docking projection 148, the elongated body 524 is translated distally over the first arm 506 and the second arm 508 locking the docking button 320 in the engaged position within the docking space 514, as described herein. To release the leadless pacemaker 104, the elongated body 526 is translated proximally until the first and second arm 506 and 508 spring radially outwards to the natural state, thereby disengaging the docking button 320.

Figure 28:
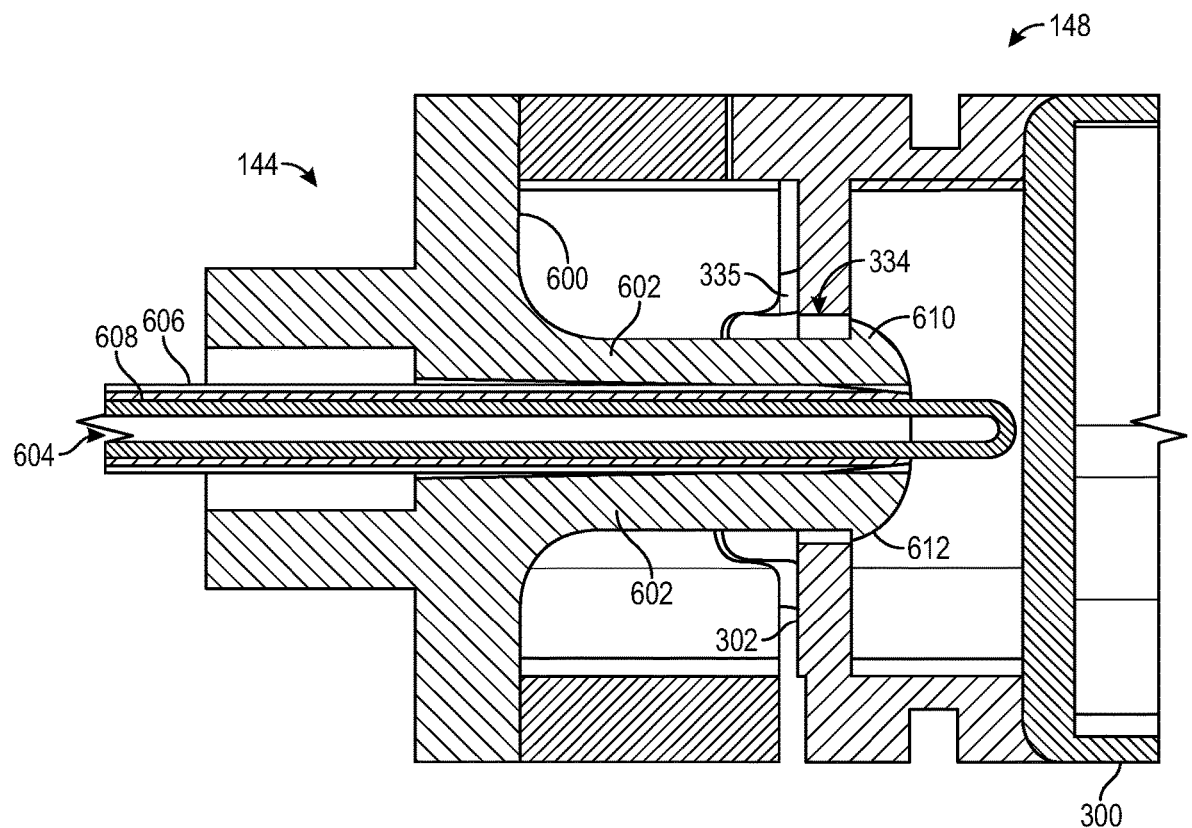
FIG. 28 is a cross-section of a retriever engaging a surface of a docking end of a leadless pacemaker within an opening in the surface.
Figure 29:
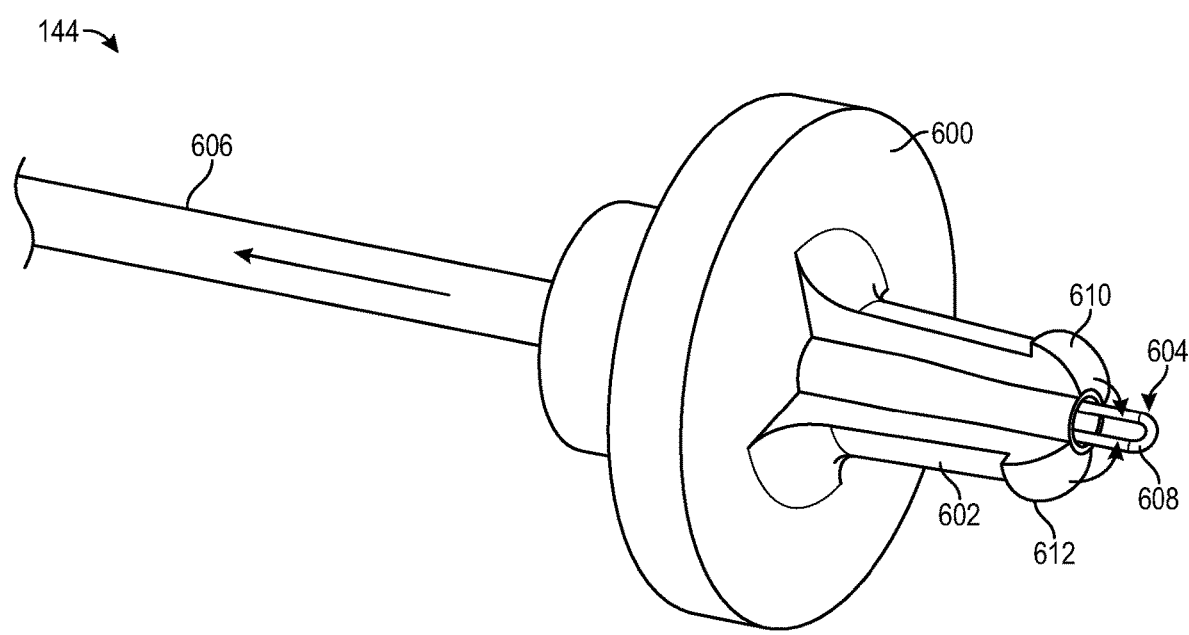
FIG. 29 shows a retriever having inwardly biased arms.

Turning to FIGS. 28 and 29, another example of the retriever 144 is shown. In one implementation, the retriever 144 includes a retriever base 600 from which a set of arms 602, including a first arm disposed opposite a second arm around a central lumen 604, extends. In one implementation, the set of arms 602 are disposed on and/or integral with a retriever shaft 606 extending through the retriever base 600. The central lumen 604 extends through the retriever shaft 606, the retriever base 600, and through the set of arms 602.

The set of arms 602 are biased radially inwards towards the central lumen 604 in a natural state. In one implementation, a mandrel 608 is translated within the central lumen 604 to move the set of arms 602 between an engaged and disengaged position with the docking projection 148. More particularly, the docking projection 148 may include a docking surface opening 334 defined within a docking surface 335 extending from or otherwise part of the surface 302 of docking end of the body 300 of the leadless pacemaker 104. The set of arms 602 include a first tab 610 and a second tab 612 each extending radially outwards from the central lumen 604. In the disengaged or natural state, the set of arms 602 are biased radially inwards, such that the set of arms 602 may be advanced through the docking surface opening 334. The mandrel 608 is advanced distally through the central lumen 604 pushing the set of arms 602 apart elastically, such that the first tab 610 and the second tab 612 are displaced radially outwards, thereby engaging the edges defining the docking surface opening 334 and locking the retriever 144 to the docking projection 148.

To disengage the retriever 144 from the docking projection 148 to release the leadless pacemaker 104, the mandrel 608 is retracted proximally within the central lumen 604, causing the set of arms 602 to spring radially inwards to the natural state. The first and second tabs 610 and 612 thus disengage the edges defining the docking surface opening 334, permitting the catheter system 108 to be retracted.

Figure 30A:
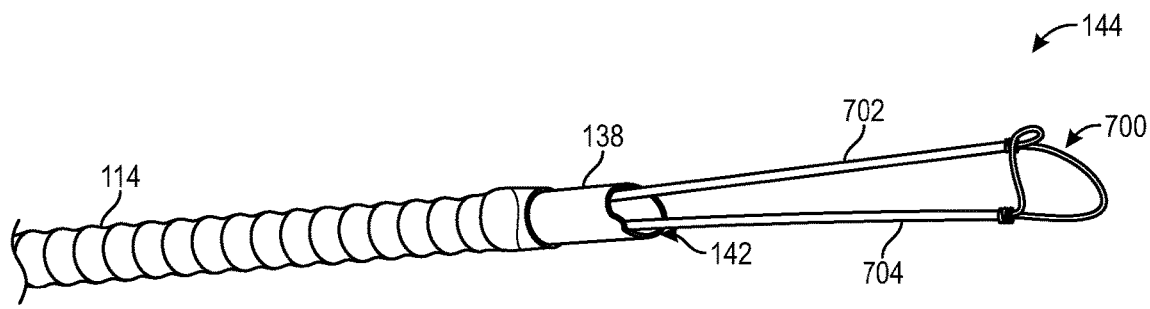
FIGS. 30A and 30B show an example retriever in the form of a snare extending from a set of sheaths.
Figure 30B:
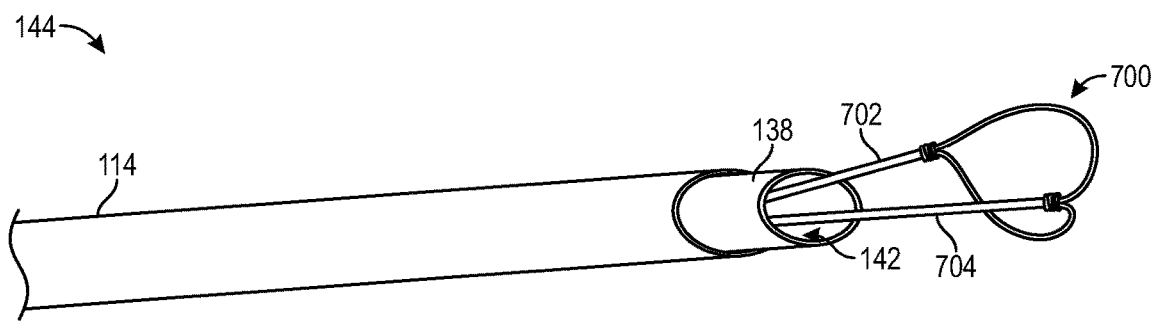

For a detailed description of examples of the retriever 144 in the form of a snare loop, reference is made to FIGS. 30A-40. Turning first to FIGS. 30A-30B, in one implementation, the body 138 of the docking cap 136 is fixed to a component of the catheter system 108, such as the torque shaft 114. The chamber 142 of the docking cap 136 is coaxial with a lumen of the catheter system 108, including, for example, a lumen of the torque shaft 114.

In one implementation, the retriever 144 includes a first sheath 702 and a second sheath 704 extending distally from the chamber 142. The first and second sheaths 702 and 704 may extend through the chamber 142 proximally into the lumen of the catheter system 108. The first and second sheaths 702 and 704 each translate longitudinally through the chamber 142 and the lumen of the torque shaft 114.

A snare 700 extends distally from and is translatable within the first and second sheaths 702 and 704. The snare 700 is configured to move between an engaged and disengaged position to releasably engage the docking projection 148. The first and second sheaths 702 and 704 may be made from a variety of materials, including, but not limited to, steel, elastic cable tubes, braided or coiled Polytetrafluoroethylene (PTFE) impregnated polyimide tubes, and/or the like. The snare 700 may be made from a variety of flexible materials, such as Nitinol or other elastic materials.

Figure 31A:
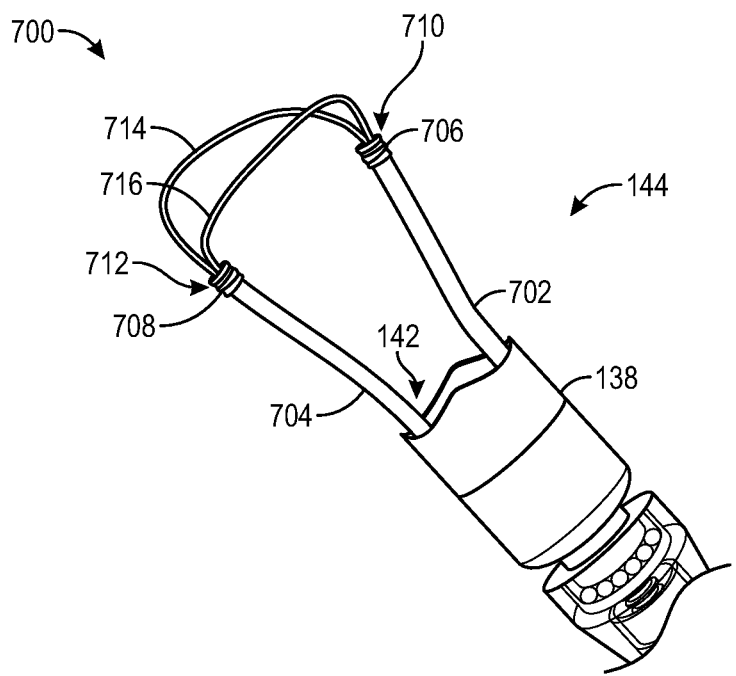
FIGS. 31A and 31B show detailed views of example snares.
Figure 31B:
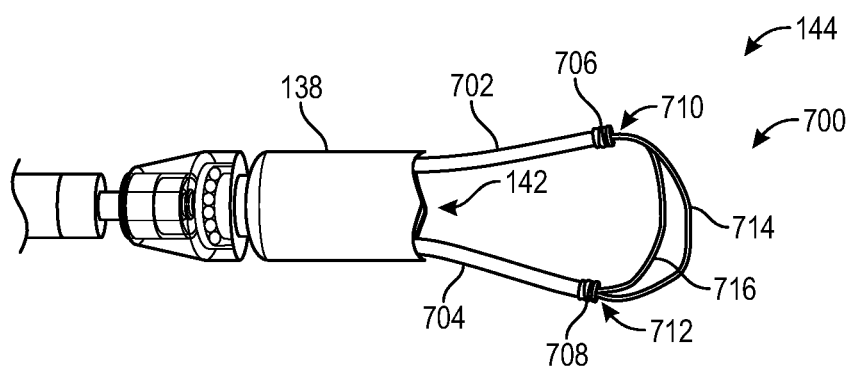

Turning to FIGS. 31A and 31B, in one implementation, the snare 700 extends from and is translatable within a first snare lumen 710 of the first sheath 702 and a second snare lumen 712 of the second sheath 704. The snare 700 moves between the engaged and disengaged positions within the first and second snare lumens 710 and 712 to capture and release the docking projection 148 of the leadless pacemaker 104. In one implementation, the first sheath 702 includes a first end coil 706, and the second sheath 704 includes a second end coil 708. Radiopacity may be obtained by making the first and second end coils 706 and 708 radiopaque. Alternatively or additionally, a NiTi DFT composite wire combining Nitinol with Titanium or Platinum in varying sheath-to-core ratios, a Tungsten or Tantalum strand in NiTi cable, and/or the like may be used for radiopacity. Further, radiopaque coils and/or marker bands may be crimped or otherwise attached to the snare 700, radiopaque coils may be wound around an NiTi core, and/or the like.

In one implementation, the snare 700 includes a first snare wire 714 and a second snare wire 716. The first snare wire 714 extends from the first snare lumen 710 into the second snare lumen 712 forming a first snare loop pointing in a first direction, and the second snare wire 716 extends from the first snare lumen 710 into the second snare lumen 712 forming a second snare loop pointing in a second direction. In one implementation, the first direction is different from the second direction, forming a docking space therebetween. The first direction may be oriented relative to the second direction such that the snare 700 forms a duckbill shape.

Figure 32:
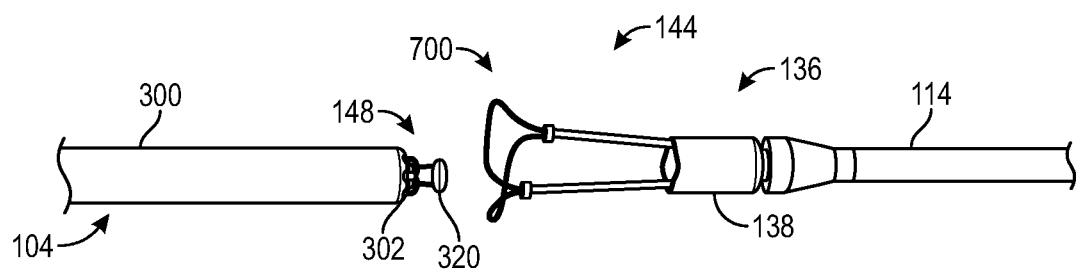
FIG. 32 illustrates an example docking space disposed relative to a docking projection of a leadless pacemaker.

As can be understood from FIGS. 32-36, to engage the docking projection 148 and lock the leadless pacemaker 104 in the docked position with the catheter system 108, the docking space formed by the snare 700 is disposed relative to at least a portion of the docking projection 148, such as the docking button 320, as shown in FIG. 32. The snare 700 is then advanced distally over the leadless pacemaker 104 until the docking projection 148 is disposed in the docking space. For example, the first snare loop and the second snare loop are advanced distally until the docking button 320 is disposed in the docking space of the snare 700, as shown in FIG. 33A. The snare 700 may be advanced by advancing the catheter system 308, the snare 700, and/or the first and second sheaths 702 and 704. The first and second sheaths 702 and 704 are translatable through the docking cap 136, and the first snare wire 714 and the second snare wire 716 are each translatable within the first snare lumen 710 and the second snare lumen 712.

Figure 33A:
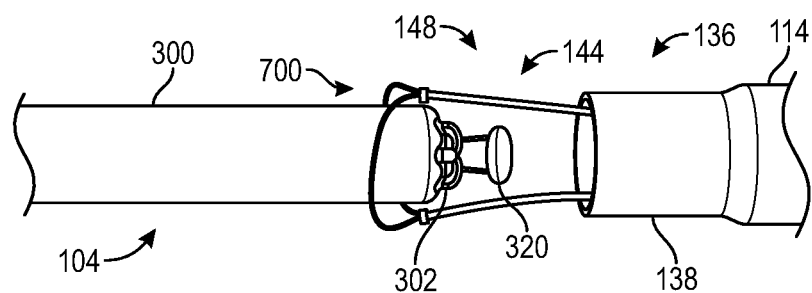
FIG. 33A shows the snare advanced over the leadless pacemaker with the docking projection disposed in the docking space.
Figure 33B:
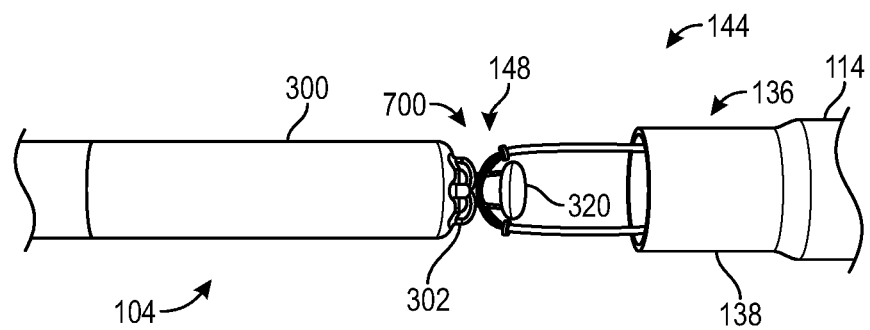
FIG. 33B illustrates the snare tightened around the docking projection in an engaged position.
Figure 34:
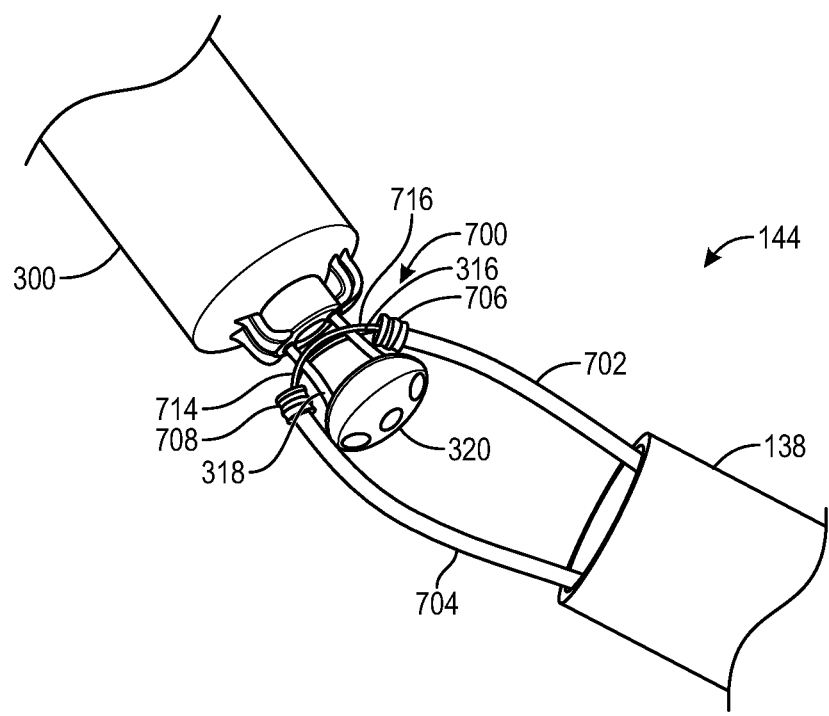
FIG. 34 is a detailed view of the snare tightened around the docking projection in the engaged position.

The snare 700 is moveable from the disengaged position to the engaged position, shown in FIGS. 33B and 34, by translating the first snare wire 714 and the second snare wire 716 proximally within the first snare lumen 710 and the second snare lumen 712. Stated differently, the first and second snare wires 714 and 716 are each retracted into the first and second snare lumens 710 and 712. The proximal translation of the first and second snare wires 714 and 716 tightens the snare 700, closing the first and second snare loops into smaller loops. Stated differently, a peak of each of the snare loops formed by the first snare wire 714 and the second snare wire 716 moves proximally towards a distal end of the first and second sheaths 702 and 704 decreasing a size of each of the snare loops. Additionally, the peaks of the snare loops formed by the first snare wire 714 and the second snare wire 716 simultaneously move towards each other and a central axis of the docking space during the proximal translation of the first and second snare wires 714 and 716. The movement of the peaks radially inwards towards each other and the central axis decreases a size of the docking space and tightens the first and second snare wires 714 and 716 around at least a portion of the docking projection 148, thereby locking the docking projection 148 in the engaged position. For example, as shown in FIGS. 33B and 34, the size of the docking space may be decreased until the first and second wires 714 and 716 close around the first and second posts 316 and 318 and/or the size of the docking space is smaller than a size of the docking button 320.

Figure 35:
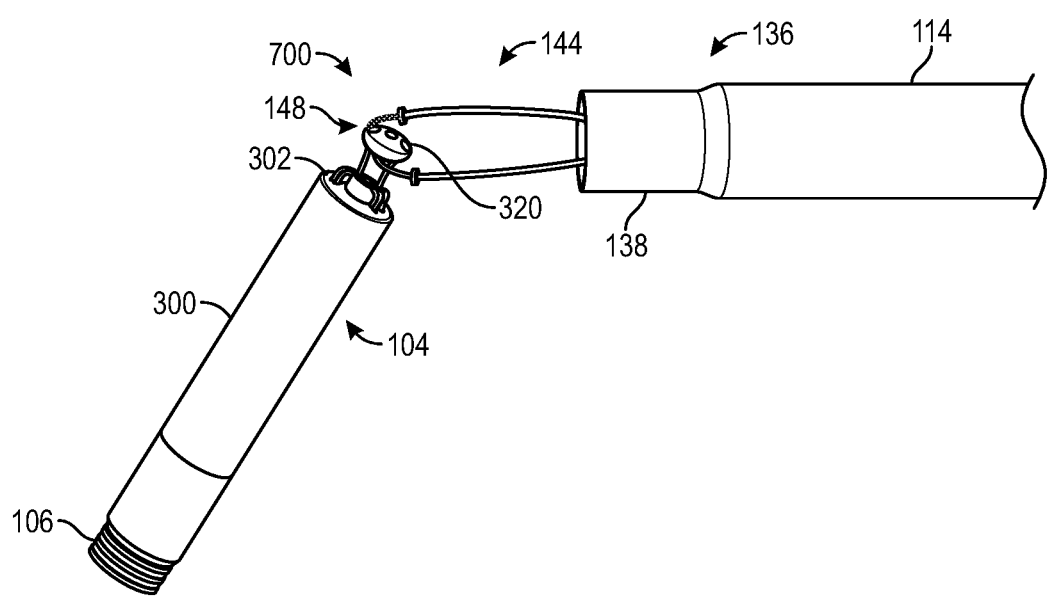
FIG. 35 illustrates movement of the leadless pacemaker relative to a longitudinal axis of the catheter in the engaged position.

The snare 700 captures and locks the docking projection 148 in the engaged position with a freedom of movement of the leadless pacemaker 104. More particularly, as shown in FIG. 35, the engagement of the snare 700 with the docking projection 148 provides a junction that permits movement of the leadless pacemaker 104 relative to a longitudinal axis of extending through the chamber 142 and/or one or more lumens of the catheter system 108. The movement may be parallel or at an angle to the longitudinal axis without releasing the leadless pacemaker 104 from the catheter system 108. For example, as shown in FIG. 35, the junction may act like a hinge allowing the repositioning of the leadless pacemaker 104 without release.

Figure 36:
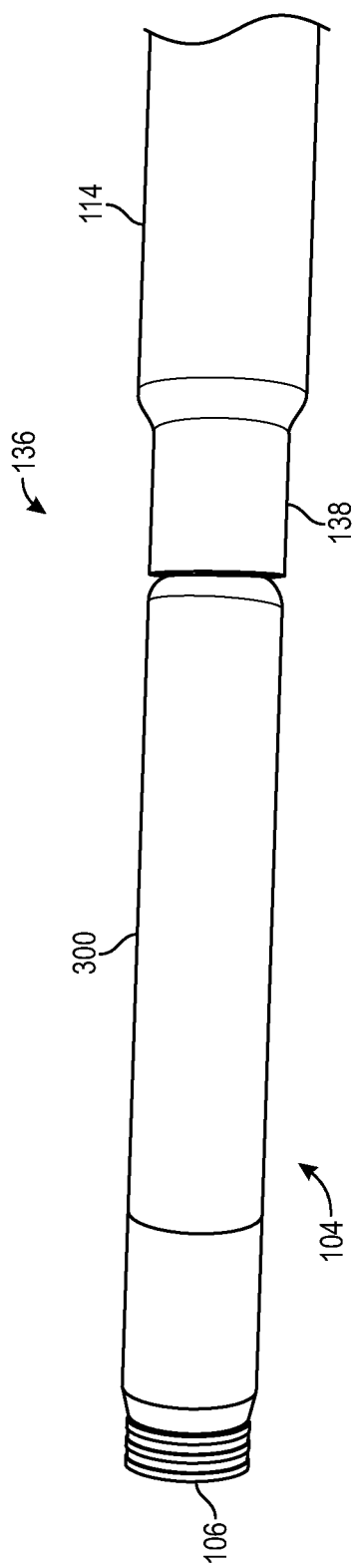
FIG. 36 shows the leadless pacemaker docked to the docking cap.
Figure 37:
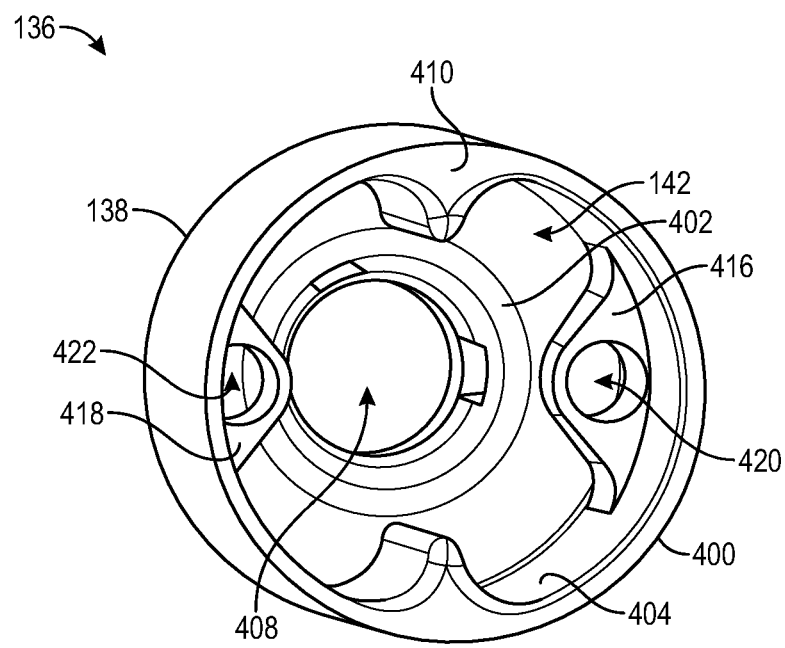
FIG. 37 illustrates an example docking cap having a first tracker and a second tracker.

Once the snare 700 is in the engaged position with the docking projection 148, to move the leadless pacemaker 104 to the docked position with the catheter 108, as shown in FIG. 36, the first sheath 702 and the second sheath 704 are retracted proximally until the docking projection 148 is disposed within the chamber 142 of the docking cap 136. In the docked position, the leadless pacemaker 104 may be moved through the patient anatomy to and/or from the implant site. During retrieval, the snare 700 and/or other features of the retriever 144 may include a cutting edge or similar mechanism for removing tissue overgrowth on the leadless pacemaker 104. Further, the retriever 144 may be used in a tether and/or test mode, for example, to test for thresholds by advancing the first and second sheaths 702 and 704 along with the first and second snare wires 714 and 716, such that the docking projection 148 remains engaged with the snare 700.

For a detailed description of the interaction of the retriever 144 with the docking cap 136, reference is made to FIGS. 37-40. In one implementation, the body 138 of the docking cap 136 includes one or more cap surfaces, as described herein, adapted to provide torque to the leadless pacemaker 104 via the docking surfaces of the docking end of the leadless pacemaker 104. In one implementation, the one or more cap surfaces are disposed relative to the chamber 142 and are adapted to matingly engage the docking surfaces and/or features of the retriever 144. The one or more cap surfaces may include the distal end surface 400, the proximal chamber surface 402, and the side surface 404 extending between the proximal chamber surface 402 and the distal end surface 400. The distal end surface 400 defines an opening into the chamber 132, and the proximal chamber surface 402 defines the proximal opening 408 into the chamber 142 extending through the receiving portion 140. The proximal opening 408 may be coaxial with the longitudinal axis of a lumen of the torque shaft 114 and/or the steerable catheter 118 and the central axis of the snare 700.

The mating engagement of each of the various cap surfaces with the corresponding docking surfaces provides torque transmission. To further facilitate torque transmission, one or more of the cap surfaces may include the cap keys 410. In one implementation, the cap keys 410 are disposed radially around the side surface 404, for example, on radially opposite sides of the longitudinal axis. The cap keys 410 may be adapted to matingly engage corresponding side keys 310 defined in the docking projection 148 for torque transmission, as described herein.

In one implementation, the docking cap 136 further includes one or more trackers corresponding to the one or more sheaths of the retriever 144. For example, the docking cap 136 may include a first tracker 416 corresponding to the first sheath 702 and a second tracker 418 corresponding to the second sheath 704. In one implementation, the first and second trackers 416 and 418 maintain the first and second sheaths 702 and 704 in an orientation relative to each other and to the center axis coaxial with the longitudinal axis running through the proximal opening 408. The orientation may include, for example, the first sheath 702 maintained in a position radially opposite the second sheath 704 about the center axis. Stated differently, the first and second sheaths 702 and 704 may be disposed approximately 180 degrees apart about the center axis.

Figure 38:
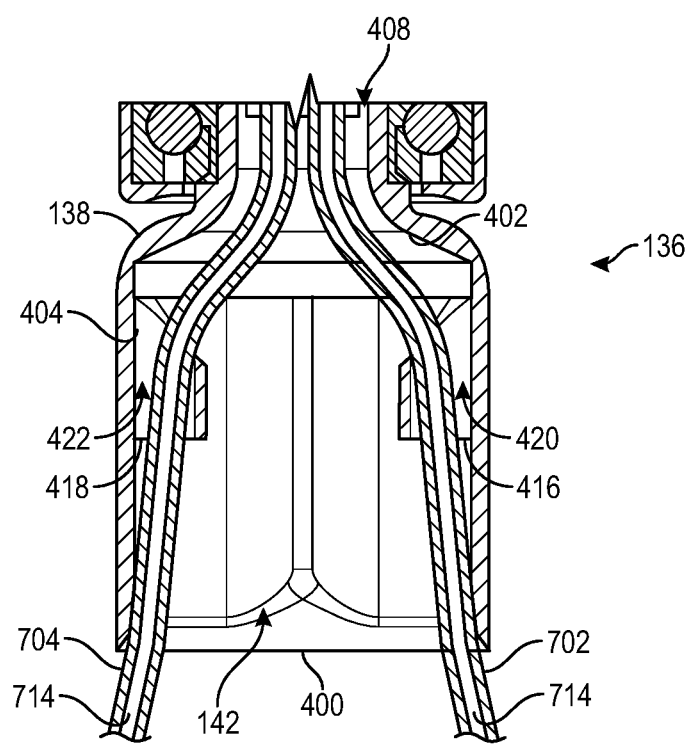
FIG. 38 is a cross-section of a retriever in the form of a snare disposed in a chamber of a docking cap.
Figure 39:
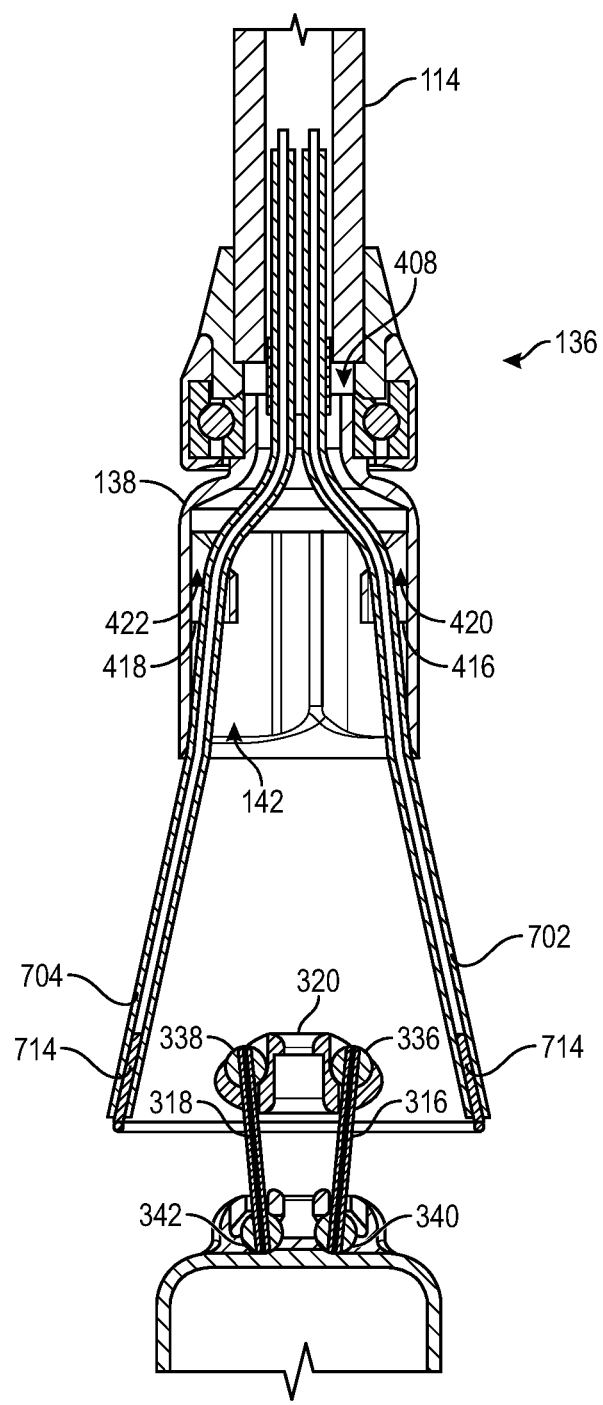
FIGS. 39 and 40 are each a cross-section of a distal end of a catheter system showing a snare engaged to a docking projection of a leadless pacemaker.
Figure 40:
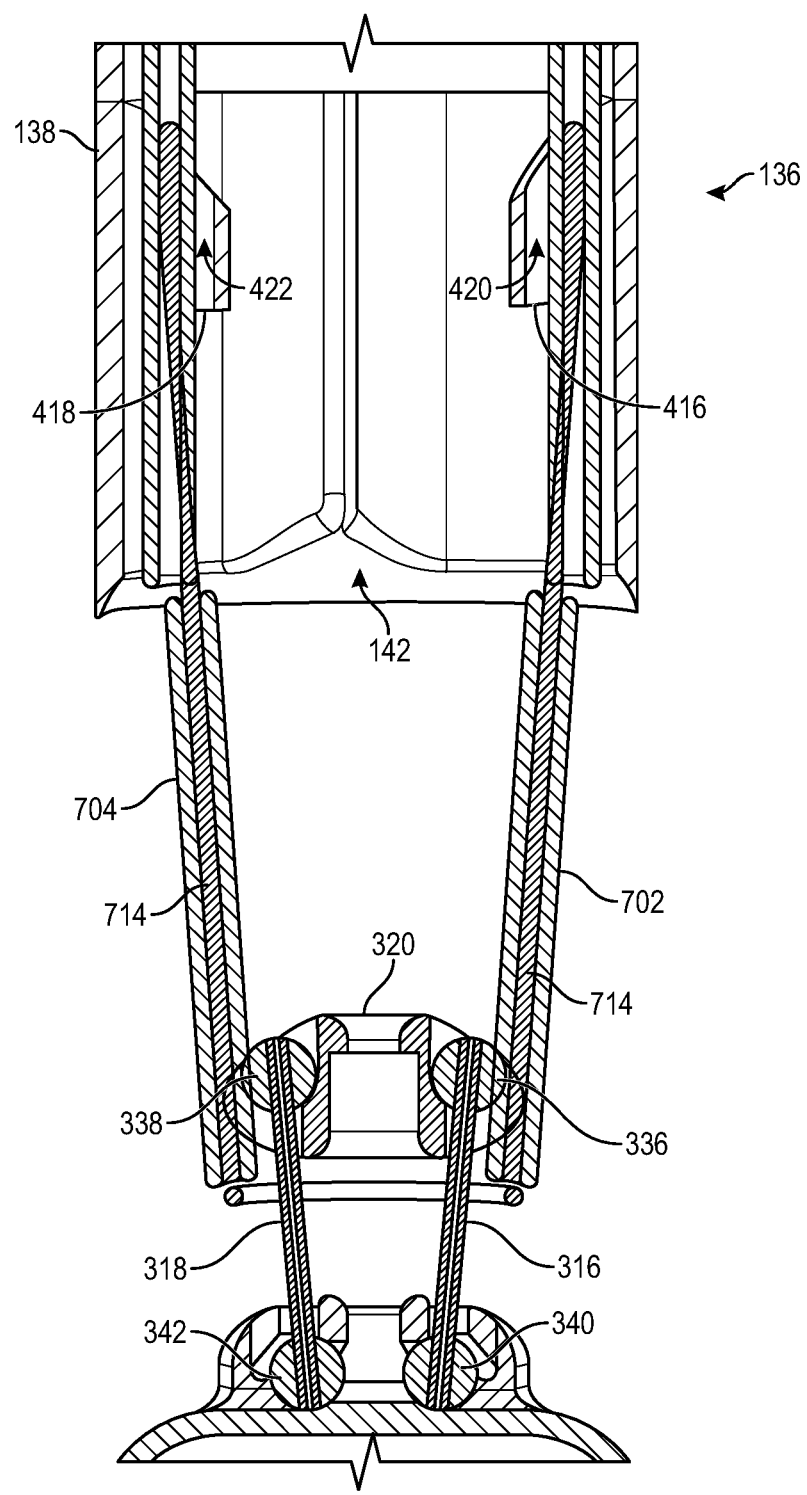

The first and second sheaths 702 and 704 are translatable within the first and second trackers 416 and 418, respectively. In one implementation, the first tracker 416 includes a first tracker lumen 420 within which the first sheath 702 is translatable, and the second tracker 418 includes a second tracker lumen 422 within which the second sheath 704 is translatable, as shown in FIGS. 38-40. The first and second trackers 416 and 418 thus maintain the first and second sheaths 702 and 704 in an orientation adapted to position the snare 700 for capturing the docking projection 148 such that it can be moved into the chamber 142 into the docking position by retracting the first and second sheaths 702 and 704 into the lumen of the torque shaft 114.

In one implementation, the docking button 320 is mounted to the docking projection 148 with a set of docking balls fixed to the first and second posts 316 and 318, as shown in FIGS. 39-40. The first post 316 may extend between a first proximal ball 336 and a first distal ball 340. The first proximal ball 336 is disposed in the first slot 328, and the first distal ball 340 extends through an opening in the end surface 308, thereby mounting the docking button 320 to the docking projection 148 with the first post 316. Similarly, the second post 318 may extend between a second proximal ball 338 and a second distal ball 342. The second proximal ball 338 is disposed in the second slot 330, and the second distal ball 342 extends through another opening in the end surface 308, thereby mounting the docking button 320 to the docking projection 148 with the second post 318. In one implementation, the first post 316 is mounted to the docking projection 148 and the docking button 320 such that it is radially symmetric with the second post 318.

It will be appreciated that the retriever 144 may be displaced to engage the docking projection 148 using the docking cap 136 as described herein. Additionally or alternatively, a push-pull actuator 826 may be used to cause the retriever 144 to engage and disengage the docking projection 148. For example, turning to FIGS. 41-46, in one implementation, the retriever 144 is in the form of a hinged grasper and displaceable between the engaged and disengaged position with a push-pull actuator 826.

Figure 41:
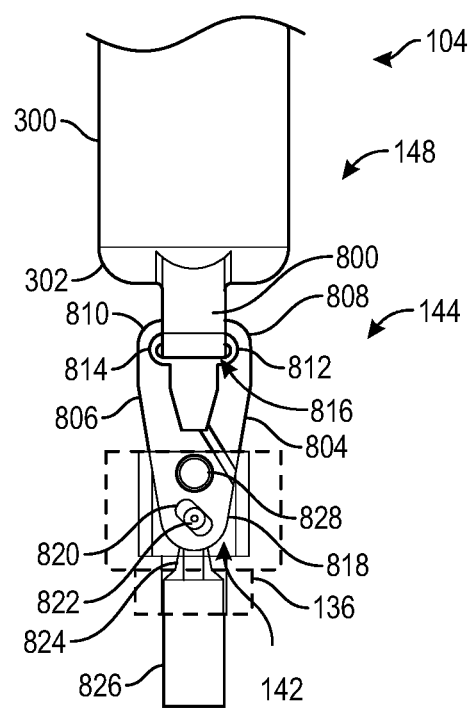
FIG. 41 shows a front view of the retriever in the form of a hinged grasper engaged to a slotted docking projection of a leadless pacemaker and displaceable with a push-pull actuator, with a docking cap shown transparent.
Figure 42:
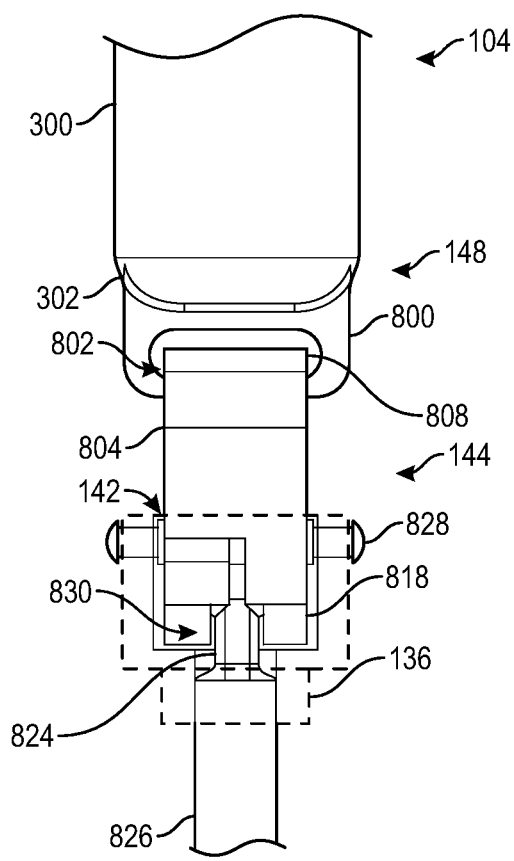
FIG. 42 shows a side view of the hinged grasper of FIG. 41.
Figure 43:
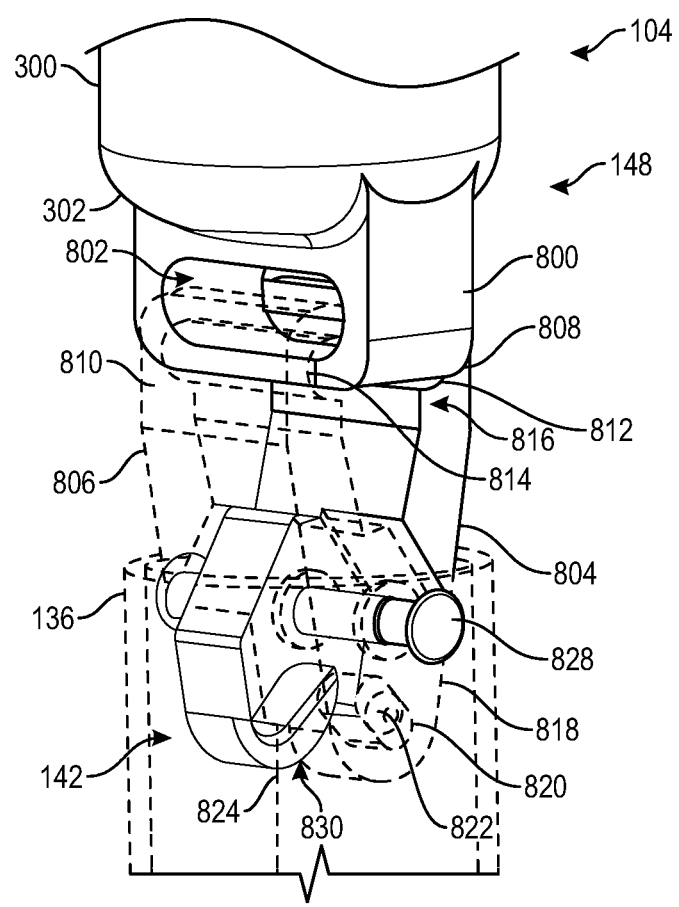
FIG. 43 is a detailed perspective view of the hinged grasper of FIG. 41 shown with the arms of the hinged grasper also transparent.

Referring first to FIGS. 41-43, in one implementation, the leadless pacemaker 104 includes the docking projection 148 extending from the surface 302 at the docking end of the body 300. The docking projection 148 includes a projection 800 defining a slot 802. In one implementation, the projection 800 has a length extending in a first direction across the surface 302, such that the length is approximately the same as a diameter of the surface 302, and the projection 800 has a narrow width extending in a second direction across the surface 302, with the width being less than the diameter of the surface 302.

The projection 800 includes one or more docking surfaces defining the slot 802 and configured to matingly engage corresponding features of the retriever 144, thereby providing torque transmission to the leadless pacemaker 104. In one implementation, the retriever 144 in the form a hinged grasper is formed with a first arm 804 and a second arm 806. A first grasping portion 808 is disposed at a distal end of the first arm 804 and includes a first cutout 812. Similarly, a second grasping portion 810 is disposed at a distal end of the second arm 806 and includes a second cutout 814.

The first cutout 812 and the second cutout 814 collectively define a docking space 816 adapted to engage the projection 800. More specifically, to engage the leadless pacemaker 104 in the engaged position, lips of the grasping portions 808 and 810 extend into the slot 802 with a proximal portion of the projection 800 disposed in the docking space 816, thereby gripping the docking projection 148 with the retriever 144. The first arm 804 and the second arm 806 move radially outwardly into the disengaged position and the grasping portions 808 and 810 release the projection 800, widening the docking space 816. In one implementation, the first arm 804 and the second arm 806 each taper in width proximally from the grasping portions 808 and 810 to a base 818.

To move the arms 804 and 806 between the engaged and disengaged positions, the push-pull 826 actuator is translated relative to the docking cap 136 within the chamber 142. The push-pull actuator 826 may extend through and be translated within a lumen of the torque shaft 114. In one implementation, the push-pull actuator 826 includes a neck 824 extending distally from a body of the push-pull actuator 826. The neck 824 includes one or more knobs 822 extending radially outwardly from a longitudinal axis of the push-pull actuator 826. The neck 824 is disposed within a gap 824 defined in each of the first arm 804 and the second arm 806, and each of the knobs engage corresponding tracks 820 in each of the arms 804 and 806. One or more hinge pins 828 extend through holes in the docking cap 136 and the arms 804 and 806 to rotationally mount the retriever 144 to the docking cap 136. Engagement of the knobs 822 with the arms 804 and 806 within the tracks 820 causes the push-pull actuator 826 to displace the arms 804 and 806 radially inwardly and outwardly relative to a rotational axis of the hinge pin(s) 828 when the body of the push-pull actuator 826 is translated distally and proximally.

Figure 44:
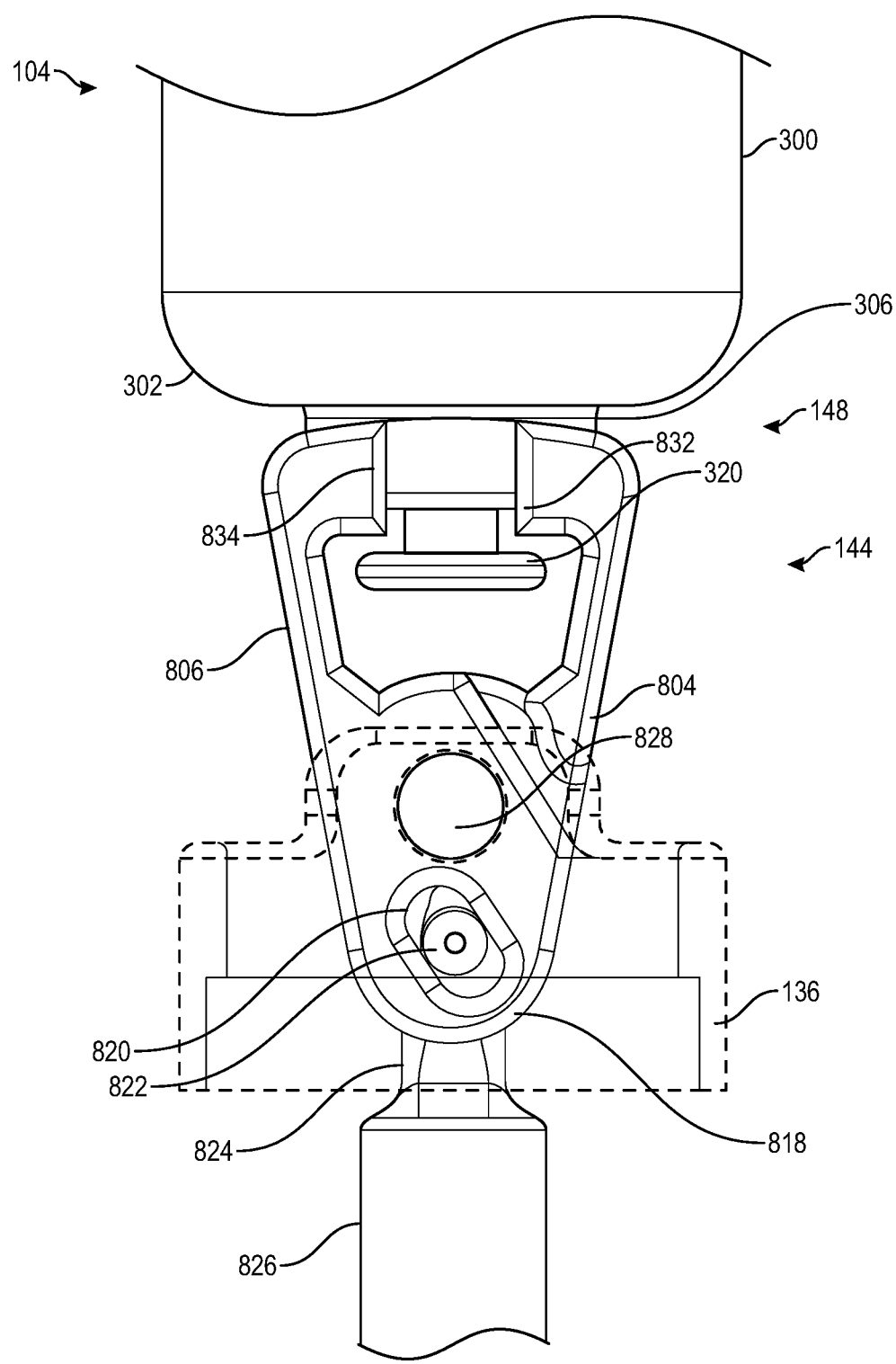
FIG. 44 shows a front view of the retriever in the form of another hinged grasper engaged to a polygonal docking projection of a leadless pacemaker and displaceable with a push-pull actuator, with a docking cap shown transparent.
Figure 45:
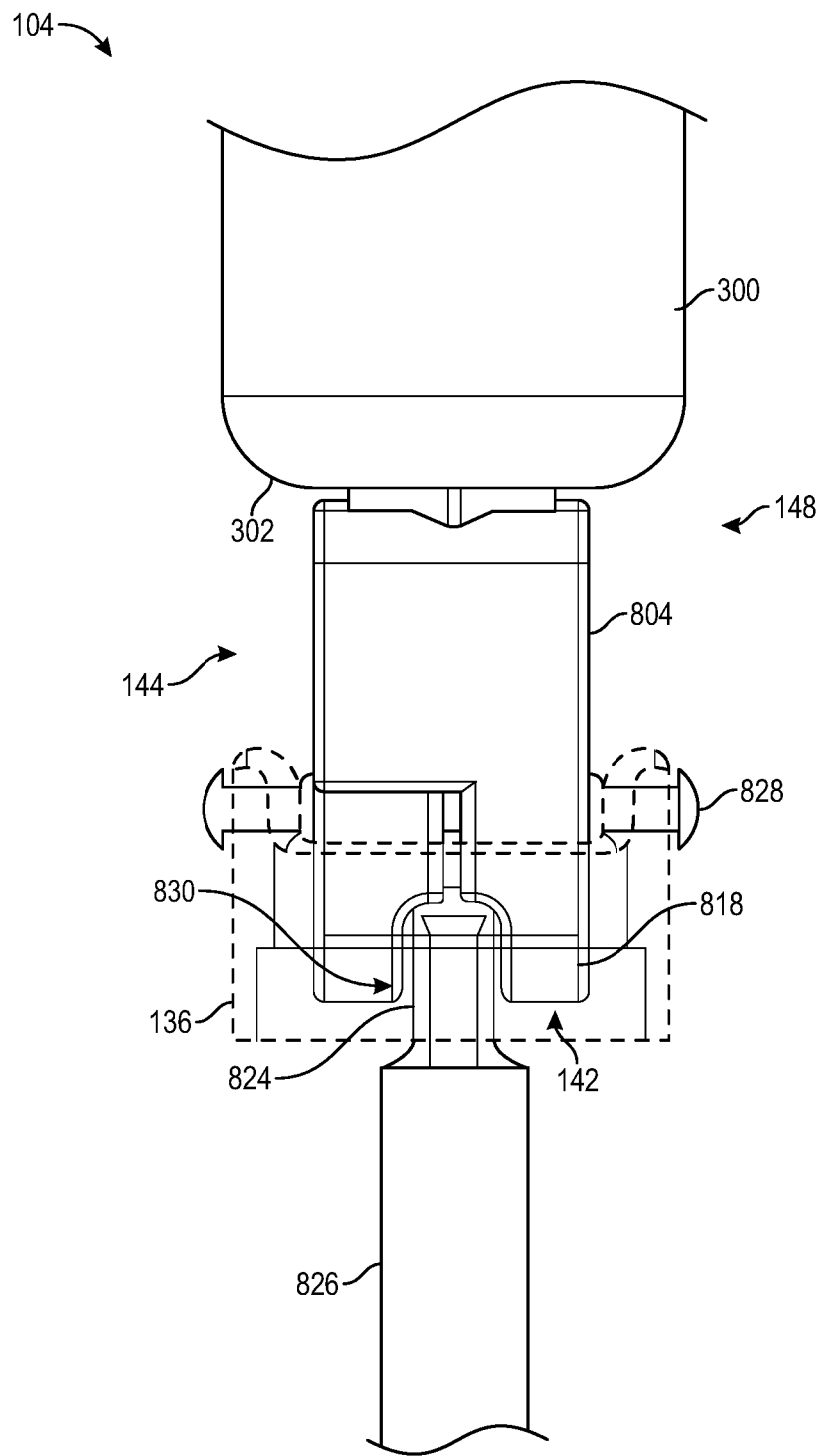
FIG. 45 shows a side view of the hinged grasper of FIG. 44.
Figure 46:
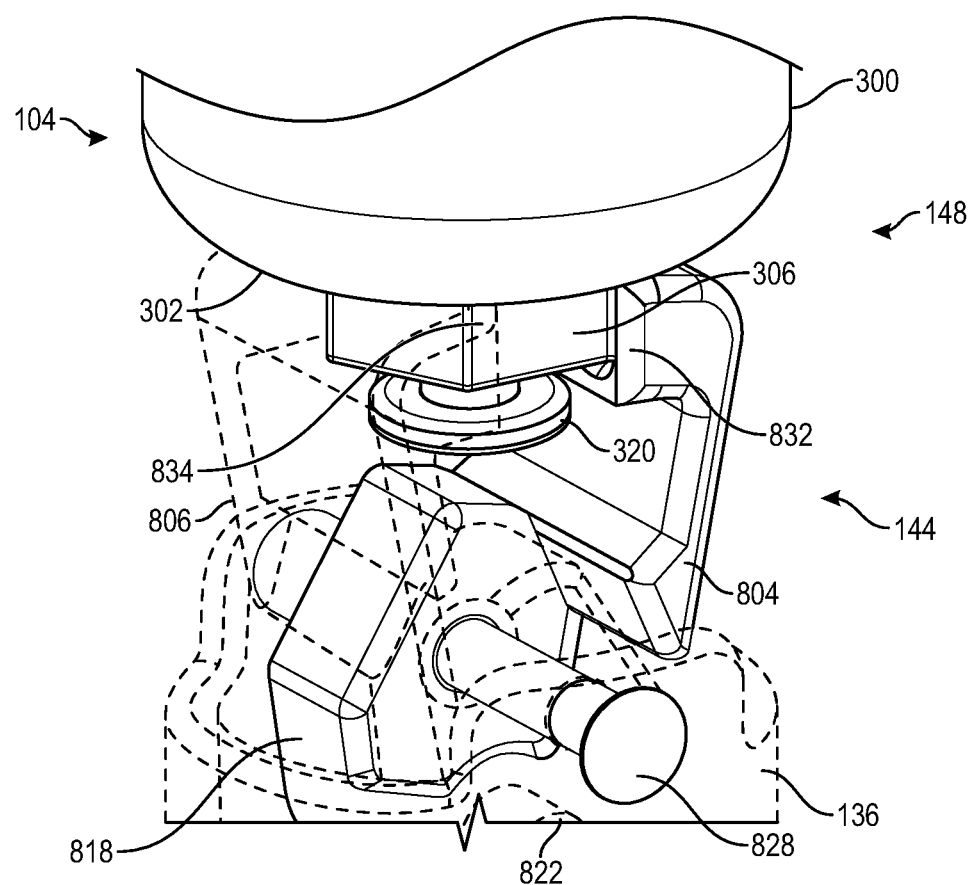
FIG. 46 is a detailed perspective view of the hinged grasper of FIG. 44 shown with the arms of the hinged grasper also transparent.

Similarly, turning to FIGS. 44-46, the first arm 804 and the second arm 806 are displaceable between the engaged and disengaged position with the push-pull actuator 826. In one implementation, the docking projection 148 includes one or more docking surfaces, including edge docking surfaces 306 and/or the like, configured to matingly engage corresponding features of the first arm 804 and the second arm 806, thereby providing torque transmission to the leadless pacemaker 104. The docking surfaces 306 may form a hexagonal shape or other polygonal shape of the docking projection 148. The first arm 804 may include a first docking surface 832, and the second arm 806 may include a second docking surface 834. Each of the first and second docking surfaces 832 and 834 may be planar or other shapes mirroring a shape of the edge docking surfaces 306.

The first docking surface 832 and the second docking surface 834 are adapted to engage one or more of the edge docking surfaces 306 of the docking projection 148. More specifically, to engage the leadless pacemaker 104 in the engaged position, first docking surface 832 and the second docking surface 834 are pressed against the edge docking surfaces 306, thereby gripping the docking projection 148 with the retriever 144. The first arm 804 and the second arm 806 move radially outwardly into the disengaged position and the grasping portions 808 and 810 release the docking projection 148.

In certain medical operations, electrophysiologists, interventional cardiologists, or similar physicians may be required to retrieve foreign objects from the vasculature or heart chambers. Conventionally, such retrievals are accomplished using a device commonly referred to as a cardiovascular snare. A snare of a cardiovascular snare design may consist of a wire formed into one to three loops and an outer tube or shaft that is advanced over the snare such that the snare can be closed about the object being retrieved. Cardiovascular snares generally only work well when the foreign body is relatively simple in shape and capable of maintaining a co-axial orientation with respect to the blood vessel inhabited by the foreign object. When a conventional snare is closed, however, the snare favors a perpendicular orientation between the foreign body and vasculature. Accordingly, if the foreign object is not capable of maintaining a co-axial orientation, the foreign object could interfere with the anatomy and cause injury or get stuck within the vasculature. Certain leadless pacemaker designs, for example, may include a rigid post or similar structure as a retrieval interface. Such a rigid post (as opposed to a flexible cable) may make interfacing or docking such leadless pacemakers to a catheter system more difficult.

In light of the foregoing, embodiments of the present disclosure include a catheter system including a snare assembly having substantially concentric snare loops that extend perpendicular to a central axis of a main catheter shaft. Such an arrangement provides several significant benefits in retrieval operations and may be used to retrieve not only leadless pacemakers, but other foreign objects such as, without limitation, vena cava filters.

Figure 47:
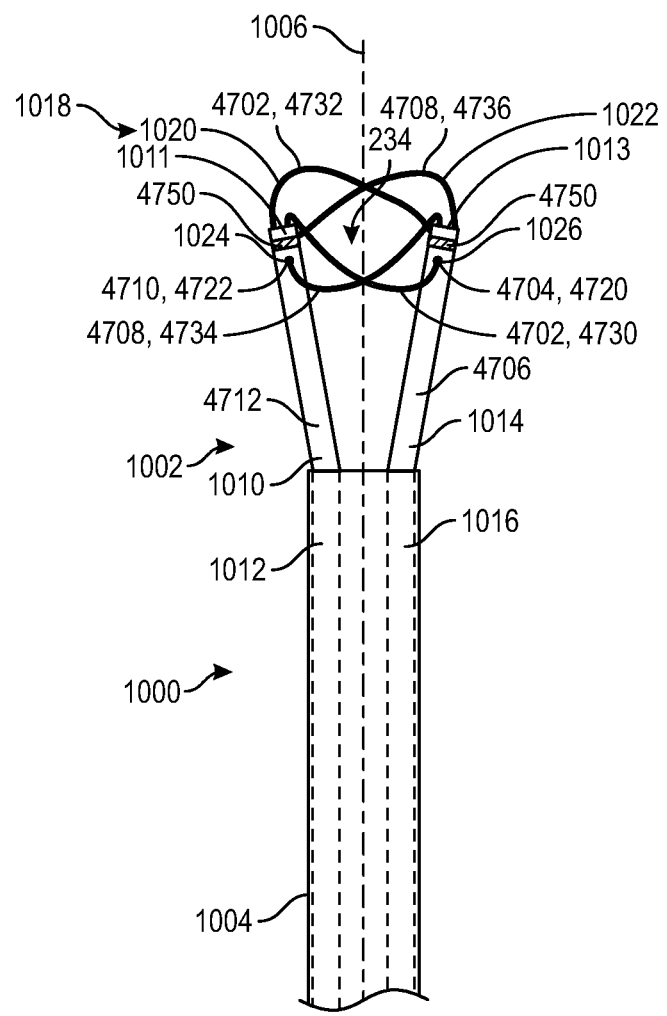
FIG. 47 is a schematic illustration of a distal end of a catheter system including a snare assembly.

FIG. 47 is a schematic illustration of a distal end 1002 of a catheter system 1000 for use with a leadless pacemaker retrieval system and in accordance with the present disclosure. The catheter system 1000 includes a shaft 1004 having a central axis 1006. The shaft 1004 can be hollow, e.g., can have a longitudinal lumen that extends along the central axis 1006 and defines the central axis 1006. The catheter system 1000 can include a first sheath 1010 and a second sheath 1014. The first sheath 1010 can extend distally from the shaft 1004 to a first end 1011. The second sheath 1014 can extend distally from the shaft 1004 to a second end 1013. Accordingly, the first sheath 1010 can be generally disposed at a position radially opposite the second sheath 1014 relative to the central axis 1006.

In an embodiment, the first sheath 1010 and the second sheath 1014 have respective lumens. For example, the first sheath 1010 can include a first lumen 1012 extending longitudinally through the sheath from a respective proximal end (not shown) to the first end 1011, and the second sheath 1014 can have a second lumen 1016 extending longitudinally through the sheath from a respective proximal end (not shown) to the second end 1013. The sheaths 1010, 1014 may run the entire length of the catheter system 1000, or, in certain implementations, may be joined or otherwise coupled into one or more members at a proximal location within the shaft 1004.

The catheter system 1000 further includes a snare assembly 1018 adapted to couple to a retrieval feature of a leadless pacemaker. More particularly, the snare assembly 1018 can have a docking space 234 that can be advanced over the leadless pacemaker to retrieve the leadless pacemaker, e.g., from a target anatomy. For example, the docking space 234 can be between one or more snare legs of the snare assembly 1018, as described below, such that the leadless pacemaker retrieval system can be advanced over the leadless pacemaker to receive the leadless pacemaker within the docking space.

As shown in FIG. 47, the snare assembly 1018 includes several snare legs, e.g., wire or suture segments, extending between the first sheath 1010 and the second sheath 1014. In an embodiment, the snare legs include several first snare legs 4702 extending from the first end 1011 to respective first leg ends 4704. The first leg ends 4704 can connect to the second sheath 1014. For example, the first snare legs 4702 can be individual wire segments that terminate at the first leg ends 4704, and the ends can be adhesively bonded, thermally welded, tied to, clipped to, or otherwise attached to a wall 4706 of the second sheath 1014, e.g., at second end 1013.

Accordingly, the first leg ends 4704 are coupled to the second sheath 1014 to bridge the gap between the first end 1011 and the second end 1013, and to define the docking space 234 between the legs.

The several snare legs can also include several second snare legs 4708, which bridge the gap between the second end 1013 and the first end 1011, and further define the docking space 234 between the legs. The second snare legs 4708 extend from the second end 1013 to respective second leg ends 4710. The second leg ends 4710 can connect to the first sheath 1010. For example, the second snare legs 4708 can be individual wire segments that terminate at the second leg ends 4710, and the ends can be adhesively bonded, thermally welded, tied to, clipped to, or otherwise attached to a wall 4712 of the first sheath 1010, e.g., at first end 1011.

In an embodiment, the first snare legs 4702 are segments of a first snare loop 1020. For example, the first snare loop 1020 can extend from the first sheath 1010 and loop back on itself at a first bight 4720. The first bight 4720 can be a central portion of the looped wire or suture. More particularly, the first bight 4720 can join the first leg ends 4704 such that the first legs 4702 extend continuously along the loop. Similarly, the second snare legs 4708 can be segments of a second snare loop 1022. For example, the second snare loop 1022 can extend from the second sheath 1014 and loop back on itself at a second bight 4722. The second bight 4722 can be a central portion of the looped wire or suture. More particularly, the second bight 4722 can join the second leg ends 4710 such that the second legs 4708 extend continuously along the loop. Accordingly, the first snare loop 1020 and the second snare loop 1022 can extend from a respective source sheath to a respective opposing sheath. The snare loops 1020, 1022 can be substantially concentric with each other to define the docking space 234 for receiving the leadless pacemaker.

The snare legs and/or snare loops can be at least partly disposed within respective lumens of the sheaths. For example, one or more of the first snare legs 4702 can extend through the first lumen 1012 of the first sheath 1010. Similarly, one or more of the second snare legs 4708 can extend through the second lumen 1016 of the second sheath 1014. In certain implementations, one or more legs of the first snare loop 1020 and the second snare loop 1022 are longitudinally translatable relative to the first sheath 1010 and the second sheath 1014 in order to close the first snare loop 1020 and the second snare loop 1022. More particularly, one or more of the first legs 4702 and one or more of the second snare legs 4708 can be retracted into the first sheath 1010 and the second sheath 1014, respectively, to reduce a size of the docking space 234. For example, each of the first snare loop 1020 and the second snare loop 1022 can be pulled into the first sheath 1010 and the second sheath 1014, respectively, to close the snare loops 1020, 1022. In other implementations, the first sheath 1010 and the second sheath 1014 may instead be extended over the first snare loop 1020 and the second snare loop 1022, respectively, to reduce the size of the docking space 234. Retraction of the snare legs and/or snare loops, or otherwise reducing the docking space 234, can tighten the snare assembly 1018 around the leadless pacemaker.

As described above, the catheter system 1000 of the leadless pacemaker retrieval system can have concentric snare loops, e.g., snare loops 1020, 1022, each sheathed by a tubular sheath and/or hollow shaft. To maintain substantial concentricity of the snare loops 1020, 1022, the snare loops 1020, 1022 are coupled to the opposite sheath. So, for example, a tip of the first snare loop 1020 can be coupled to the second sheath 1014 while a tip of the second snare loop 1022 can be coupled to the first sheath 1010. Accordingly, as one of the snare loop 1020, 1022 is closed (e.g., by retraction of the snare loop or extension of the sheath through which the snare loop extends), the snare loop being closed also pulls the opposite sheath, thereby applying a closing force on the opposite sheath and loop. Similarly, as one of the snare loops 1020, 1022 is opened (e.g., by extension of the snare loop or retraction of the sheath through which the snare loop extends), the snare loop being opened also pushes the opposite sheath, thereby applying an opening force on the opposite sheath and loop. The fact that the legs of the snares are linked together at their tips allows for equal forces to be applied on opposite sides of the loops when the legs are retracted or advanced from the sheaths. The equal force distribution can keep the snares concentric during reduction and expansion of docking space 234. In certain implementations, the snare loops 1020, 1022 may be set into a certain shape using heat or may be otherwise preformed into a particular shape. Preshaping the snare loops can further contribute to a repeatable increase or decrease in the docking space 234 area during snare assembly actuation. Accordingly, the snare assembly 1018 provides an engagement system that is easy to engage and disengage, and repeatably opens and closes, avoiding complications during implant and retrieval of, e.g., a leadless pacemaker.

In certain implementations, the catheter system 1000 may be implemented as a retrieval catheter of a broader retrieval system, e.g., a leadless pacemaker retrieval system. Such systems can include one or more handle portions coupled to the snare assembly 1018. The handle portion(s) or similar structure may be used to manipulate and actuate components of the catheter system, as described above with respect to FIG. 2. In certain implementations, for example, the handle may include features or handle portions adapted to relatively translate the first snare loop 1020 relative to the first sheath 1010 and/or the second snare loop 1022 relative to the second sheath 1014. For example, the handle may include a first handle portion that, when manipulated, can extend or retract the first sheath 1010 over the first snare loop 1020. Alternatively, manipulating the first handle portion may translate the first snare loop 1020 to extend from or retract into the first sheath 1010. Accordingly, movement of the first handle portion can cause a first length of the first snare legs 4702 between the first end 1011 and the second sheath 4706 to change. For example, the first handle portion can be coupled to one or more of the first snare legs 4702 to change the first length. In certain implementations, the first handle portion may simultaneously translate the second snare loop 1022 relative to the second sheath 1014. Accordingly, movement of the first handle portion can cause a second length of the second snare legs 4708 between the second end 1013 and the first sheath 1010 to change. In alternative implementations, the handle may include a second handle portion that enables independent manipulation of the second snare loop 1022 or the second sheath 1014 from the first snare loop 1020 and the first sheath 1010. For example, the second handle portion can be coupled to one or more of the second snare legs 4708 to change the second length. Accordingly, the handle portions can cause the first length and the second length to increase or decrease, which results in a reduction or increase of docking space 234. When the docking space is reduced, the snare legs can grasp the leadless pacemaker. As such, the first sheath 1010 and the second sheath 1014 can be retracted into a catheter, e.g., into catheter system 108, to retrieve the leadless pacemaker or other target device.

Figure 48A:
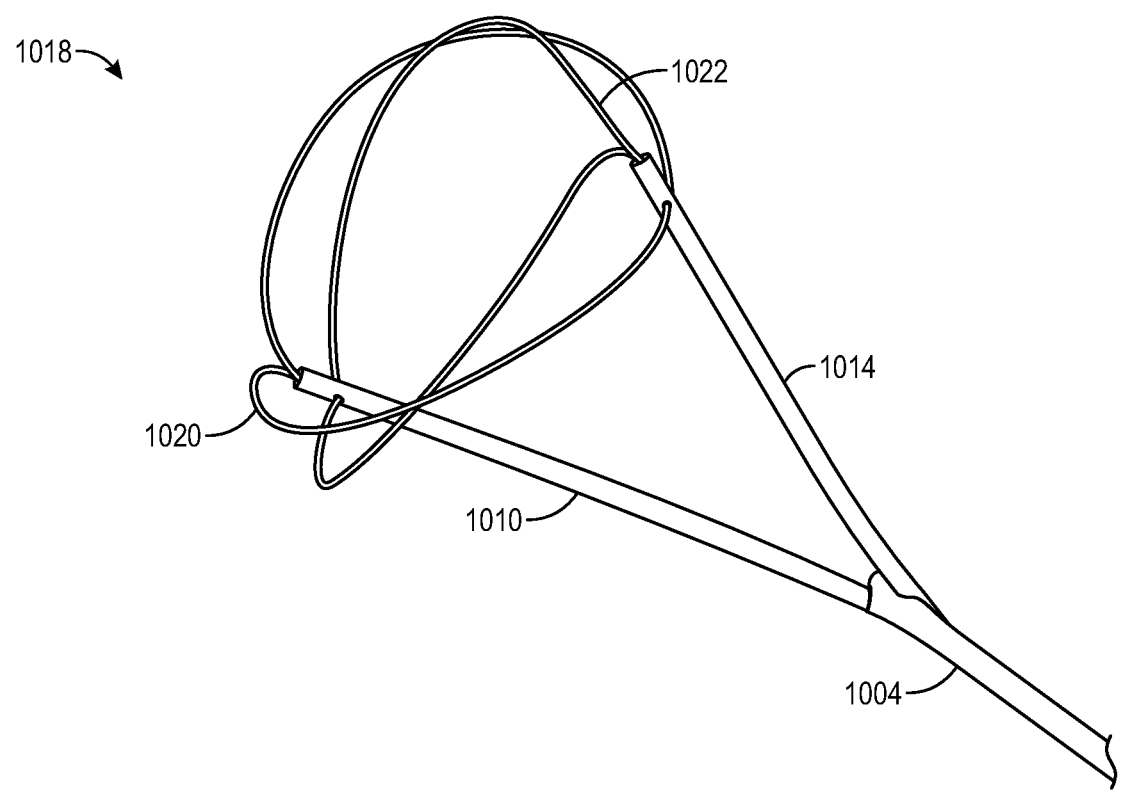
FIGS. 48A and 48B are perspective views of the snare assembly of FIG. 47 in an open and closed configuration, respectively.
Figure 48B:
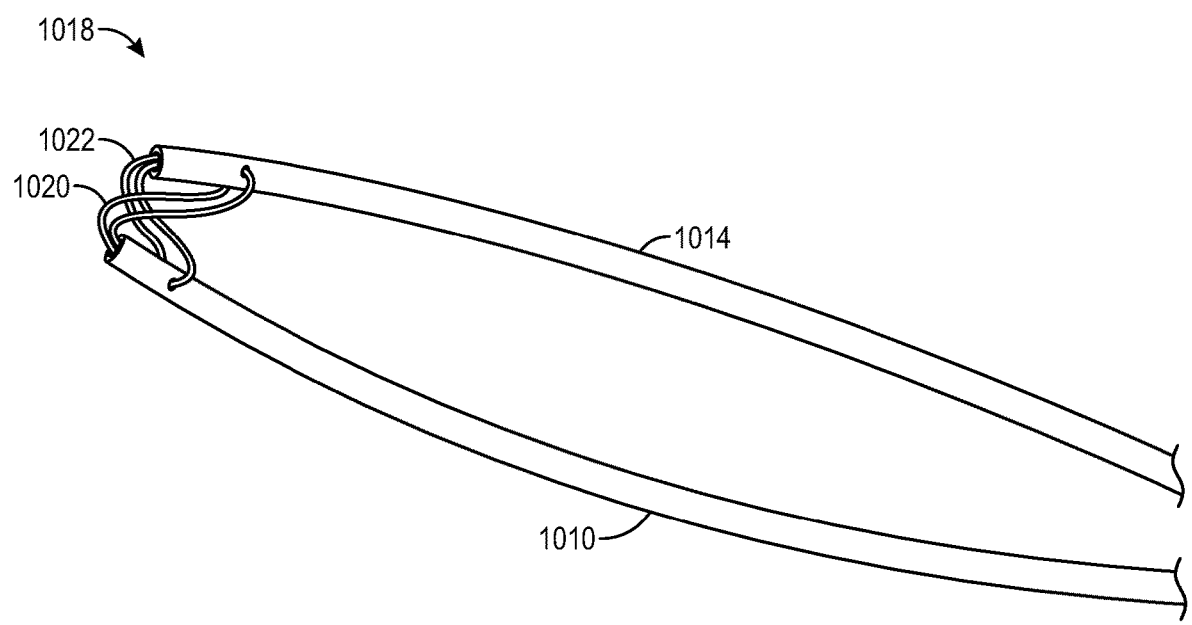

FIGS. 48A and 48B illustrate the snare assembly 1018 in an expanded/open configuration and a constricted/closed configuration, respectively. As previously noted, transitioning between the open and closed configurations can be achieved in various ways including by extending and retracting the sheaths 1010, 1014 over their respective snare loops 1020, 1022. Alternatively, transitioning between the open and closed configurations may be achieved by extending/retracting the snare loops 1020, 1022 into and out of their respective sheaths 1010, 1014.

Coupling of the snare loops 1020, 1022 to the opposite sheath 1014, 1010 can be achieved in various ways. As illustrated in FIGS. 47-48B, for example, the bights 4720, 4722 of respective snare loops can be coupled to respective sheaths. In an embodiment, the first bight 4702 is attached to the second sheath 1014, and the second bight 4722 is attached to the first sheath 1010. The bights can be attached to the sheaths in a variety of manners. For example, the catheter system 1000 can include a passage in one or more of the sheaths. In an embodiment, a lateral passageway 1024 is formed in the wall 4712 of the first sheath 1010 (FIG. 47). Similarly, a lateral passageway 1026 can be formed in the wall 4706 of the second sheath 1014. The passages 4712, 4706 can extend laterally through their respective sheaths. For example, the passages can be drilled, laser cut, punched, or otherwise formed through the sheath walls in a direction orthogonal to the longitudinal axes of the sheaths. Accordingly, the passageways can intersect the inner lumens, 1012, 1016, of the respective sheaths. In an embodiment, first snare loop 1020 extends, e.g., is passed through, the lateral passageway 1026 of the second sheath 1014, and the second snare loop 1022 extends, e.g., is passed through, the lateral passageway 1024 of the first sheath 1010. The portions of the snare loops that are in the passages 1024, 1026 can be the tips of the snare loops 1020, 1022. Accordingly, the first bight 4702 can be within the second lumen 1016, and the second bight 4722 can be within the first lumen 1012.

Although various other arrangements are possible, the passageways 1024, 1026 of FIGS. 47-48B are generally implemented as a pair of opposite holes extending through the sidewalls of the first sheath 1010 and the second sheath 1014. Such holes may be formed using various techniques including, without limitation, laser or mechanical drilling. Accordingly, the bights 4702, 4722 can be attached to sheaths 1014, 1010, respectively, by retention forces applied to the wires by the sidewalls.

Figure 49A:
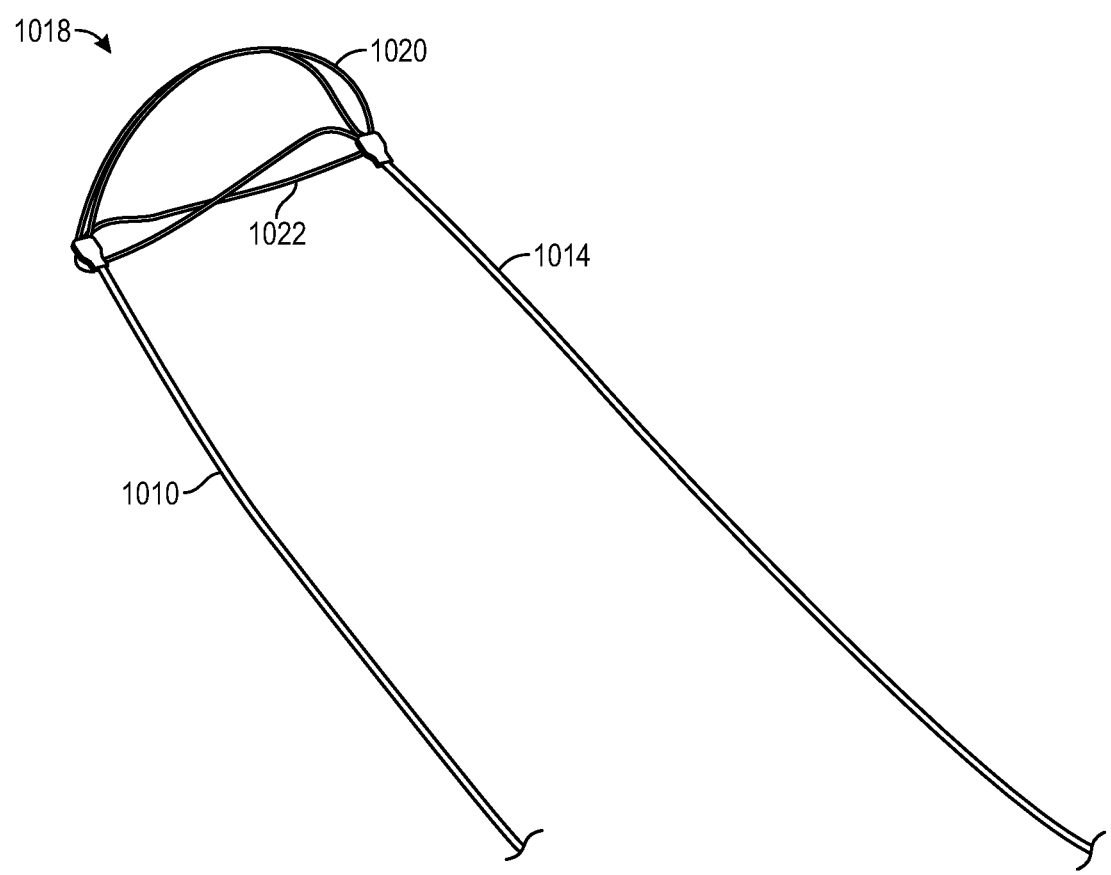
FIGS. 49A and 49B are perspective views of an alternate implementation of snare assembly of FIG. 47 in an open and closed configuration, respectively.
Figure 49B:
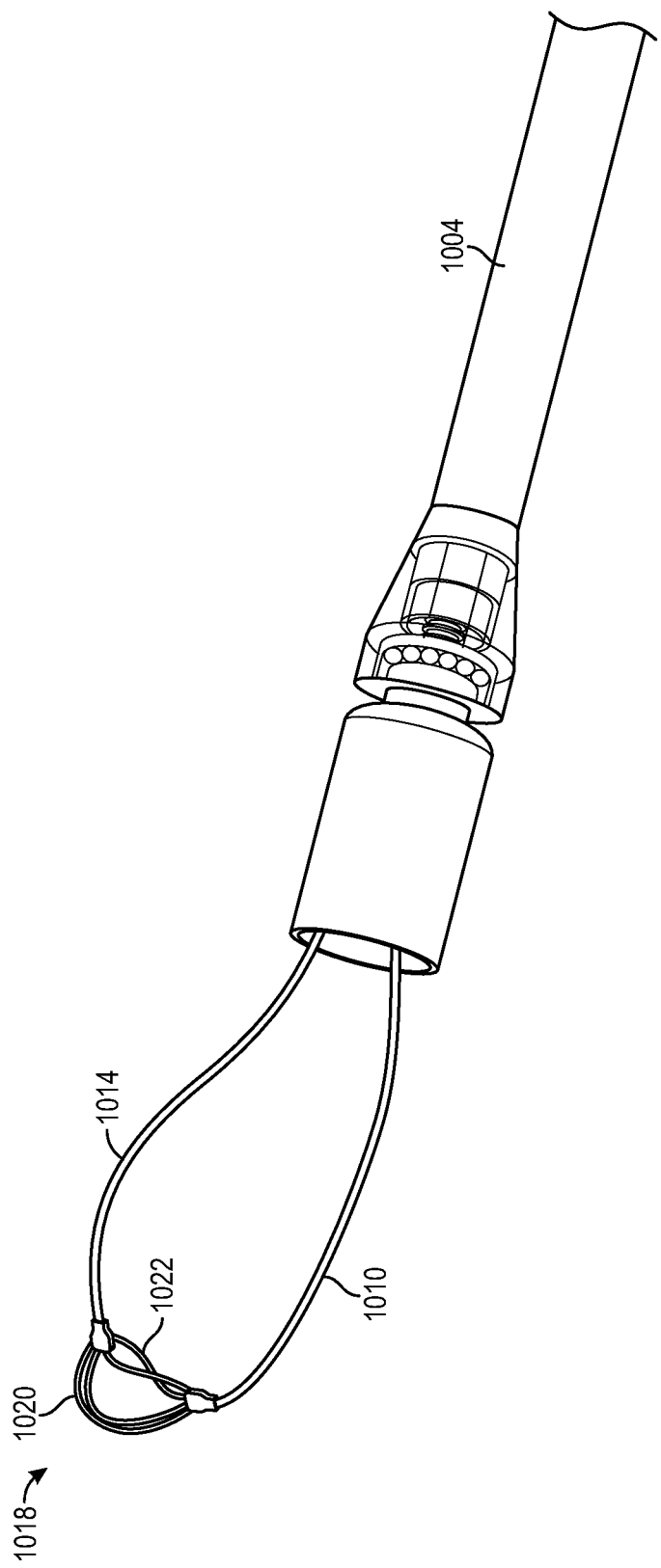

In alternative implementations, the snare legs 4702, 4708 can be attached to corresponding sheaths by a bond. More particularly, a mechanical joint or mechanism can hold the legs, leg ends, and/or snare loops to the walls of the sheaths. In an embodiment, the bond includes one or more small cuffs, clips, or similar features made of metal, plastic, or any other suitable material in order to secure the snare loops 1020, 1022 to the opposite sheaths 1014, 1010, respectively. For example, the clip can attach the first bight 4702 or terminal ends of the first snare legs 4702 to the second sheath 1014. In still other implementations and as illustrated in FIGS. 49A and 49B, the snare loops 1020, 1022 may be coupled to the opposite sheaths 1014, 1010, respectively, using an adhesive. For example, the bond can include an adhesive joint to attach the first bight 4702 or terminal ends of the first snare legs 4702 to the second sheath 1014. Although illustrated in the drawings as being formed from a continuous wire, the snare loops 1020, 1022 may, in certain implementations, be formed from two separate wires. For example, referring again to FIG. 47, each of a first wire, e.g., a first leg 4730, and a second wire, e.g., a second leg 4732, may extend from a source sheath, e.g., first sheath 1010, and be separately coupled to the opposite sheath, e.g., the second sheath 1014, at terminal leg ends 4704. Similarly, each of a second wire, e.g., a third leg 4734, and a second wire, e.g., a second leg 4736, may extend from a source sheath, e.g., second sheath 1014, and be separately coupled to the opposite sheath, e.g., the first sheath 1010, at terminal leg ends 4710. Accordingly, the distal end of each snare loop can be secured to the distal end of an opposite sheath in numerous manners.

The sheaths 1010, 1014 may be formed from one or more suitable materials. For example, in certain implementations, the sheaths 1010, 1014 may be formed, at least in part, from polyether ether ketone (PEEK). The sheaths 1010, 1014 may also be formed, at least in part, from one or more of a metal coil, plastics other than PEEK, or a braided plastic tube made with a material such as a polyether block amide (such as PEBAX®).

In certain implementations, a radiopaque element may also be crimped, swaged, or otherwise coupled to one or both of the sheaths 1010, 1014 such that the radiopaque element may be used to track the sheaths 1010, 1014 using fluoroscopy or a similar method. For example, radiopaque markers 4750 can be on one or more of the first sheath 101 or the second sheath 1014. More particularly, the radiopaque marker(s) 4750 can be on the first end 1011 and/or the second end 1013.

In certain implementations, the sheaths 1010, 1014 have an inner diameter of approximately 0.017 inches or at least twice the diameter of the wire from which the snare loops 1020, 1022 are formed, an outer diameter of approximately 0.019 inches, and, as a result, a wall thickness of at least 0.002 inches. In other implementations, the sheaths 1010, 1014 may have a wall thickness of at least 0.001 inches. In still other implementations, the wall thickness of the sheaths 1010, 1014 is sufficient to provide column and tensile strength to avoid buckling of the sheaths during opening and closing of the snare loops 1020, 1022.

The snare loops 1020, 1022 may also be formed from one or more suitable materials. For example, in one implementation, each of the first snare loop 1020 and the second snare loop 1022 are formed from a flexible, shape-memory alloy, such as nickel-titanium. In certain implementations, a radiopaque marker or wire may be wrapped around or otherwise coupled to one or both of the snare loops 1020, 1022 to provide visibility of the snare loops 1020, 1022 through fluoroscopy, or a similar imaging technique.

In certain implementations, the first snare loop 1020 and the second snare loop 1022 may be formed from a wire having a diameter of approximately 0.008 inches. This diameter may be larger if, as noted above, a radiopaque marker or wire is coupled to or wrapped around the snare loop 1020, 1022. In certain implementations, the snare loops 1020, 1022 may have a wire diameter greater than 0.008 inches, particularly in applications in which improved force distribution or loop resiliency is required to avoid damage to the foreign object (e.g., a pacemaker) being retrieved.

As illustrated in FIG. 48A, the snare loops 1020, 1022 may be configured to expand to have a predetermined effective diameter. For purposes of this disclosure, the term "effective diameter" is used to refer to a diameter of an imaginary circle having an area equal to that enclosed by a snare loop and which may or may not be circular in shape. For example, the effective diameter can be a cross-sectional dimension of the docking space 234 between the snare legs. The effective diameter of the snare loops 1020, 1022 when in the open configuration may vary depending on a given application and, in particular, the shape and dimensions of a foreign object being retrieved. However, in one example implementation, the snare loops 1020, 1022 have an effective diameter from and including 20 millimeters to and including 30 millimeters when in the open configuration. When in the closed configuration, as shown in FIG. 48B, the effective diameter of the snare loops 1020, 1022 is significantly restricted. For example, in one implementation, the snare loops 1020, 1022 may have an effective diameter of approximately 1 millimeter.

The snare loops 1020, 1022 can be linked together. As depicted in FIG. 48A, the two open linked snares 1020 and 1022 present five potential openings for the snare assembly 1018 to engage the leadless pacemaker docking button 320: a main central opening/loop and four smaller satellite openings/loops. The main and satellite openings are between respective snare legs. Advantageously, the openings provide a greater number of angles at which the snare assembly 1018 can successfully engage docking button 320. Also, advantageously the snare assembly 1018 depicted in FIG. 48B, which includes two snares 1020 and 1022, permits a tighter engagement with docking button 320 than otherwise possible using a single snare.

FIGS. 50A-50B illustrate different implementations of a snare loop 1120, such as the first snare loop 1020 or the second snare loop 1022 of FIGS. 46-49B. As shown in FIG. 50A, the snare loops 1120 may be formed by extending a wire 1150 through a sheath 1110, looping the wire 1150 back on itself, and passing the wire back into the sheath 1110. As a result, two wire legs 1154A, 1154B extend through the sheath 1110. For example, leg 1154A can be the first leg 4730 of the first snare loop 1020 described above, and leg 1154B can be the second leg 4732 of the first snare loop 1020. Accordingly, the first leg 4730 and the second leg 4732 can extend through the first lumen 1012 in the first sheath 1010. Similarly, leg 1154A can be the third leg 4734 of the second snare loop 1022 described above, and leg 1154B can be the fourth leg 4736 of the second snare loop 1022. Accordingly, the third leg 4734 and the fourth leg 4736 can extend through the second lumen 1016 in the second sheath 1014. The legs can run the entire length of the sheath or catheter system.

In an embodiment, as shown in FIG. 50B, ends of the snare loop 1120 may be crimped or otherwise coupled together. For example, the second leg 4732 can have a proximal end 5002 that is joined to the first leg 4730. A joint 5004 between the proximal end 5002 and a portion of the first leg 4730 can be a bond, e.g., an adhesive joint or a mechanical clamp. The joint 5004 can be distal to the end 1011 of the sheath 1110. Accordingly, only a single leg 1156, e.g., first leg 4730, may extend through the sheath 1110. Alternatively, the joint 5004 may be proximal to the sheath 1110, e.g., within hollow shaft 1004. Accordingly, both legs 4730, 4732 of the snare loop 1120 may extend through the sheath 1110 to join at the joint 5004 proximal to the sheath 1110. In any case, the leg(s) can run the entire length of the sheath or catheter system.

Figure 51:
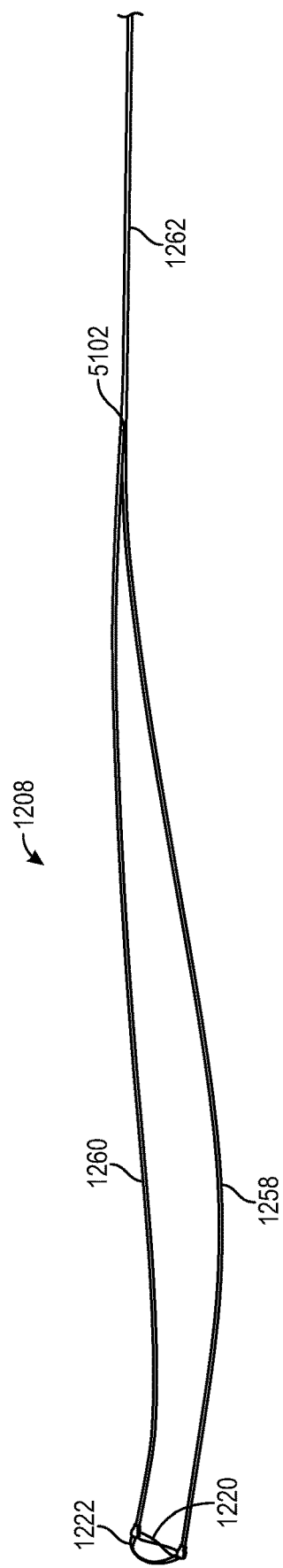
FIG. 51 is a perspective view of a snare assembly in accordance with the present disclosure.

FIG. 51 is another example implementation including a first snare loop 1220 and a second snare loop 1222 of a snare assembly 1208. As shown, each of the first snare loop 1220 and the second snare loop 1222 have respective leg bundles 1258, 1260. The leg bundles can have a single leg or several legs extending proximally through a respective sheath, as described above. The leg bundles 1258, 1260 can be joined at a proximal location. In certain implementations, the leg bundles 1258, 1260 may be joined at a proximal snare segment 1262. Accordingly, one or more of the first snare legs 4702 and one or more of the second snare legs 4708 can be joined at the proximal snare segment 1262. In certain implementations, the proximal snare segment 1262 may include a hypotube or other reinforced structure. Such an arrangement may be desirable when the snare loops 1220, 1222 are implemented with a deflectable catheter because the hypotube 1262 generally has a higher column strength as compared to the wires forming the snare loops 1220, 1222, thereby allowing for better control of the snare loops 1220, 1222. The hypotube or other proximal snare segment 1262 structure can include a distal segment end 5102. In an embodiment, the snare loops are joined at the distal segment end 5102, e.g., of a hypotube, by passing through the distal segment end 5102 into a lumen of the hypotube. In such case, the snare loops can be constrained by the hypotube and thereby joined at the transition point.

Turning back to FIG. 2, the snare assembly 1018 may be employed using catheter system 108, which may include a steerable catheter 116 for deflecting the snare assembly 1018 during a delivery and/or retrieval procedure. Advantageously, in certain embodiments, first snare loop 1020 and second snare loop 1022 are flexible such that they align themselves with the axis of a foreign body, e.g., leadless pacemaker, even when delivered at an acute angle. After this, deflection can be used to align the docking cap 136 with the pacemaker.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A catheter system comprising:
   a shaft;
   a first sheath extending distally from the shaft to a first end, wherein the first sheath includes a first lumen having a first lumen end at the first end;
   a second sheath extending distally from the shaft to a second end, wherein the second sheath includes a second lumen having a second lumen end at the second end; and
   a snare assembly including
   a plurality of first snare legs extending through the first lumen end at the first end to respective first leg ends coupled directly to the second sheath, and
   a plurality of second snare legs extending through the second lumen end at the second end to respective second leg ends coupled directly to the first sheath.

2. The catheter system of claim 1, wherein one or more of the plurality of first snare legs extend through a first proximal portion of the first lumen of the first sheath, and wherein one or more of the plurality of second snare legs extend through a second proximal portion of the second lumen of the second sheath.

3. The catheter system of claim 2, wherein the plurality of first snare legs are segments of a first snare loop extending from the first sheath to a first bight joining the first leg ends, and wherein the plurality of second snare legs are segments of a second snare loop extending from the second sheath to a second bight joining the second leg ends.

4. The catheter system of claim 3, wherein the first bight is attached to the second sheath, and wherein the second bight is attached to the first sheath.

5. The catheter system of claim 4 further comprising a passage extending laterally through a wall of the second sheath, wherein the first snare loop extends through the passage such that the first bight is within the second lumen.

6. The catheter system of claim 2, wherein the plurality of first snare legs include a first leg extending through the first proximal portion of the first lumen, and a second leg having a proximal end joined to the first leg.

7. The catheter system of claim 2, wherein the one or more of the plurality of first snare legs and the one or more of the plurality of second snare legs are joined at a proximal snare segment.

8. The catheter system of claim 7, wherein the proximal snare segment includes a hypotube, and wherein the one or more of the plurality of first snare legs and the one or more of the plurality of second snare legs are joined at a distal segment end of the hypotube.

9. The catheter system of claim 1, wherein the plurality of first snare legs are attached to the second sheath by a bond.

10. The catheter system of claim 9, wherein the bond includes a clip.

11. The catheter system of claim 1 further comprising one or more radiopaque markers on one or more of the first sheath or the second sheath.

12. The catheter system of claim 11, wherein the one or more radiopaque markers are on one or more of the first end or the second end.

13. A leadless pacemaker retrieval system comprising:
a shaft;
a first sheath extending distally from the shaft to a first end, wherein the first sheath includes a first lumen having a first lumen end at the first end;
a second sheath extending distally from the shaft to a second end, wherein the second sheath includes a second lumen having a second lumen end at the second end;
a snare assembly including
a plurality of first snare legs extending through the first lumen end at the first end to respective first leg ends coupled directly to the second sheath, and
a plurality of second snare legs extending through the second lumen end at the second end to respective second leg ends coupled directly to the second sheath; and
one or more handle portions coupled to the snare assembly, wherein movement of the one or more handle portions causes a first length of the plurality of first snare legs between the first end and the second sheath to change.

14. The leadless pacemaker retrieval system of claim 13, wherein the plurality of first snare legs are segments of a first snare loop extending from the first sheath to a first bight joining the first leg ends, and wherein the plurality of second snare legs are segments of a second snare loop extending from the second sheath to a second bight joining the second leg ends.

15. The leadless pacemaker retrieval system of claim 14, wherein the first bight is attached to the second sheath, and wherein the second bight is attached to the first sheath.

16. The leadless pacemaker retrieval system of claim 13, wherein movement of the one or more handle portions causes a second length of the plurality of second snare legs between the second end and the first sheath to change.

17. The leadless pacemaker retrieval system of claim 16, wherein the one or more handle portions includes a first handle portion coupled to one or more of the first snare legs to change the first length, and a second handle portion coupled to the one or more of the second snare legs to change the second length.

18. A method, comprising:
advancing a docking space of a snare assembly of a leadless pacemaker retrieval system over a leadless pacemaker, wherein the snare assembly includes a plurality of first snare legs extending from a first end of a first sheath to respective first leg ends coupled to a second sheath, and a plurality of second snare legs extending from a second end of the second sheath to respective second leg ends coupled to the first sheath, wherein the docking space is between the plurality of first snare legs and the plurality of second snare legs;
reducing the docking space by retracting one or more of the plurality of first snare legs into the first sheath and one or more of the plurality of second snare legs into the second sheath such that the snare assembly tightens around the leadless pacemaker; and
retracting the first sheath and the second sheath into a catheter to retrieve the leadless pacemaker.

19. The method of claim 18, wherein the plurality of first snare legs are segments of a first snare loop extending from the first sheath to a first bight joining the first leg ends, and wherein the plurality of second snare legs are segments of a second snare loop extending from the second sheath to a second bight joining the second leg ends.

20. The catheter system of claim 1, wherein the respective first leg ends are coupled directly to the second sheath distal to the shaft, and wherein the respective second leg ends are coupled directly to the first sheath distal to the shaft.

* * * * *